US012655181B2

(12) United States Patent
Denkovskiene et al.

(10) Patent No.: US 12,655,181 B2
(45) Date of Patent: Jun. 16, 2026

(54) KLEBICINS FOR THE CONTROL OF KLEBSIELLA

(71) Applicant: Nomad Bioscience GmbH, Munich (DE)

(72) Inventors: Erna Denkovskiene, Vilnius (LT); Audrius Misiunas, Vilnius (LT); Aušra Ražanskiene, Vilniaus raj. (LT)

(73) Assignee: Nomad Bioscience GmbH, Munich (DE)

( * ) Notice: Subject to any disclaimer, the term of this patent is extended or adjusted under 35 U.S.C. 154(b) by 119 days.

(21) Appl. No.: 17/615,384

(22) PCT Filed: Jun. 5, 2020

(86) PCT No.: PCT/EP2020/065652
§ 371 (c)(1),
(2) Date: Nov. 30, 2021

(87) PCT Pub. No.: WO2020/245376
PCT Pub. Date: Dec. 10, 2020

(65) Prior Publication Data
US 2022/0227818 A1     Jul. 21, 2022

(51) Int. Cl.
*C07K 14/26*     (2006.01)
*A61K 38/00*     (2006.01)
*A61P 31/04*     (2006.01)

(52) U.S. Cl.
CPC .............. *C07K 14/26* (2013.01); *A61P 31/04* (2018.01); *A61K 38/00* (2013.01)

(58) Field of Classification Search
None
See application file for complete search history.

(56) References Cited

U.S. PATENT DOCUMENTS

2016/0345599 A1* 12/2016 Giritch ..................... A23B 4/20

FOREIGN PATENT DOCUMENTS

| WO | 2014009744 | | 1/2014 | |
| WO | 2016046218 | A1 | 3/2016 | |
| WO | WO-2018075375 | A1 * | 4/2018 | ........... A61K 31/407 |

OTHER PUBLICATIONS

Ghequire et al. "The ColM Family, Polymorphc Toxins Breaching the Bacterial Cell Wall," mBio 9: e02267-17 (Year: 2018).*
GenBank: CTQ17225 (Year: 2015).*
GenBank: CAF2810748.1 (Year: 2021).*
Gu et al. "A fatal outbreak of ST11 carbapenem-resistant hypervirulent Klebsiella pneumoniae in a Chinese hospital: a molecular epidemiological study," Lancet Infect Dis 2018; 18: 37-46 (Year: 2018).*

Prasant Kumar Jena, et al., "Bacteriocin PJ4 Active Enteric Pathogen Produced by Lactobacillus helveticus PJF Isolated from Gut Microflora of Wistar Rat (*Rattus norvegicus*): Partial Purification and Characterization of Bacteriocin", Applied Biochemistry and Biotechnology, Feb. 1, 2013, pp. 2088-2100, vol. 169, No. 7, Springer Science +Business Media, New York, US.
Vidhyasagar Venkatasubramanian, et al., "Bacteriocin activity against various pathogens produced by Pediococcus pentosaceus VJ13 isolated from Idly batter", Biometrical Journal, Jun. 11, 2013, pp. 1497-1502, vol. 27, No. 11, John Wiley & Sons, Ltd.
Kamel Bendjeddou, et al., "Characterization and purification of a bacteriocin from *Lactobacillus paracasei* subsp. *paracasei* BMK2005, an intestinal isolate active against multidrug-resistant pathogens, World Journal of Microbiology and Biotechnology", Dec. 3, 2011, pp. 1543-1552, vol. 28, No. 4, Springer Science+Business Media B.V. 2011.
Zachary S. Elliott, et al., "The Role of fosA in Challenges with Fosfomycin Susceptibility Testing of Multispecies Klebsiella pneumoniae Carbapenemase Producing Clinical Isolates", Journal of Clinical Microbiology, Jul. 24, 2019, pp. 1-8, vol. 57, No. 10.
Database UnitProt [Online] May 8, 2019 (May 8, 2019), "Subname: Full=Lipid Il-degrading bacteriocin {ECO:0000313: EMBL: EAB2325411.1}; XP002792847" retrieved from EBI accession No. A0A3W8ZTQ0.
Database UnitProt [Online] Oct. 25, 2018 (Oct. 25, 2018), "RecName: Full=Channel_Colicin domain-containing protein {ECO:0000259: Pfam: PF01024} XP002794555" retrieved from EBI accession No. A0A237PTB8.
Database UnitProt [Online] Jul. 18, 2018 (Jul. 18, 2018), "RecName: Full=Channel_Colicin domain-containing protein {ECO:0000259: Pfam: PF01024} XP002794556" retrieved from EBI accession No. A0A2U4DYM9.
Database UniProt [Online] Iwase T., et al., "Complete genome sequence of Klebsiella pneumoniae YH43. XP002794557" retrieved from EBI accession No. A0A0M4UN41.
Erna Denkovskiene et al., "Broad and Efficient Control of Klebsiella Pathogens by Peptidoglycan-Degrading and Pore-Forming Bacteriocins Klebicins", Scientific Reports, Oct. 28, 2019, pp. 1-12, vol. 9, No. 1.
International Search Report and Written Opinion of the International searching Authority mailed on Mar. 31, 2020 in PCT/EP2020/065652.
Braun et al., "Isolation, Characterization, and Action of Colicin M", Antimicrobial Agents and Chemotherapy, vol. 5, No. 5, p. 520-533, May 1974.
GenBank Accession EWD35590.1, Feb. 6, 2014, Assembly Name: Kleb_pneu_UCI_33_V1.
GenBank Accession KLF15318.1, May 21, 2015, Definition: hypothetical protein YA26_09955.
GenBank Accession AML36089.1, Sep. 21, 2017, Definition: Colicin-M [Klebsiella aerogenes].
GenBank Accession SAV78255.1, May 19, 2016, Definition: Colicin-A [Klebsiella pneumoniae].
GenBank Accession KZR04287.1, Apr. 25, 2016, Definition: hypothetical protein A3N63_21265 [Klebsiella aerogenes].
GenBank Accession SAP36688.1, May 19, 2016, Definition: Colicin-B [Klebsiella oxytoca].

(Continued)

*Primary Examiner* — Christina Bradley

(74) *Attorney, Agent, or Firm* — Williams Mullen; David M. Saravitz

(57) ABSTRACT

The invention provides a protein having cytotoxic activity against *Klebsiella*, said protein having a lipid Il-cleaving activity or a pore-forming capability in a cell membrane of *Klebsiella*.

3 Claims, 35 Drawing Sheets

Specification includes a Sequence Listing.

(56)           References Cited

OTHER PUBLICATIONS

GenBank Accession BAS34675, Sep. 15, 2015, Definition: colicin pore forming domain-containing protein [Klebsiella pneumoniae].
GenBank Accession KDL88409.1, Jul. 25, 2017, Definition: hypothetical protein AE02_05353 [Klebsiella variicola].

* cited by examiner

Fig.3A

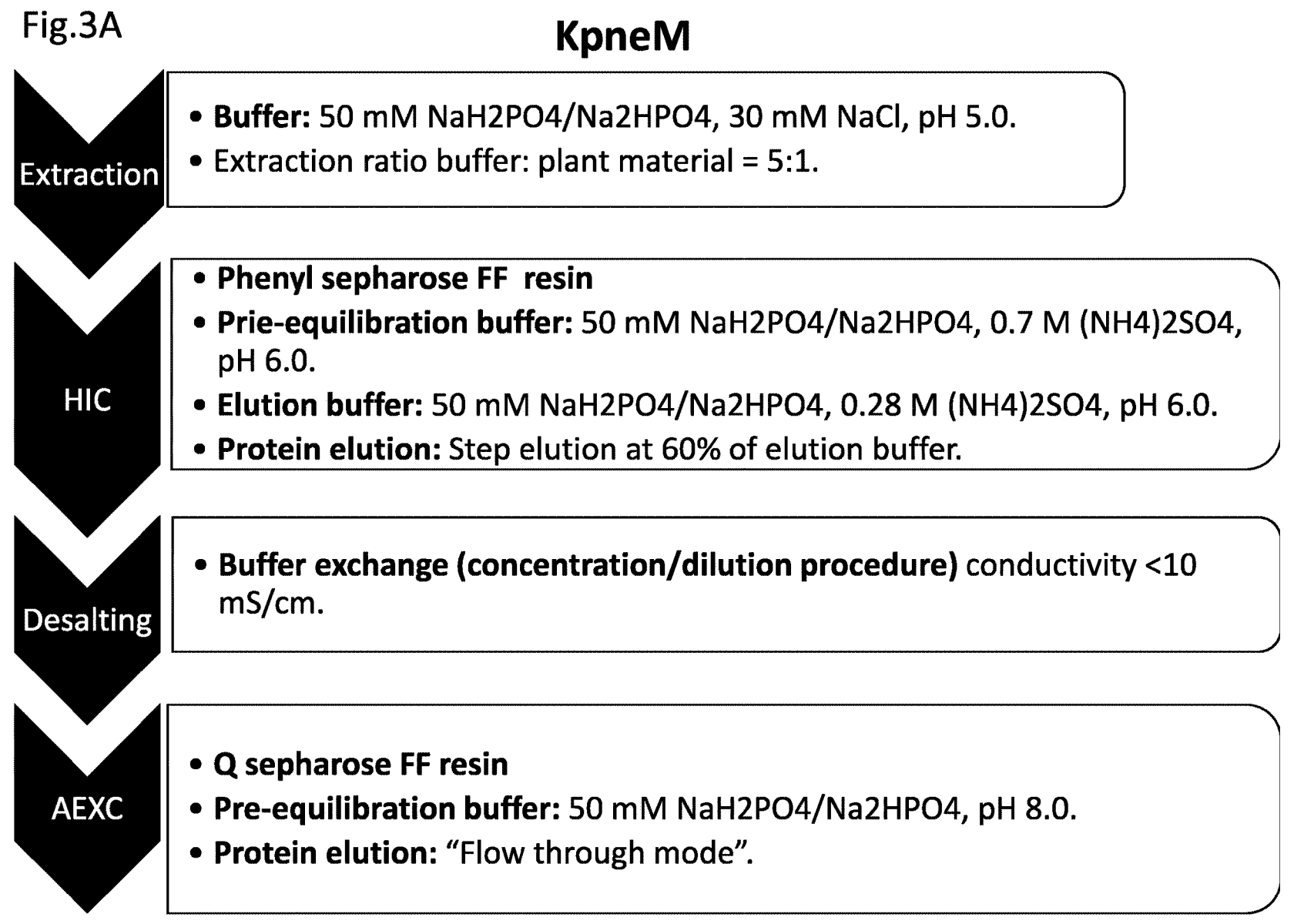

KpneM

Extraction
- Buffer: 50 mM NaH2PO4/Na2HPO4, 30 mM NaCl, pH 5.0.
- Extraction ratio buffer: plant material = 5:1.

HIC
- Phenyl sepharose FF resin
- Prie-equilibration buffer: 50 mM NaH2PO4/Na2HPO4, 0.7 M (NH4)2SO4, pH 6.0.
- Elution buffer: 50 mM NaH2PO4/Na2HPO4, 0.28 M (NH4)2SO4, pH 6.0.
- Protein elution: Step elution at 60% of elution buffer.

Desalting
- Buffer exchange (concentration/dilution procedure) conductivity <10 mS/cm.

AEXC
- Q sepharose FF resin
- Pre-equilibration buffer: 50 mM NaH2PO4/Na2HPO4, pH 8.0.
- Protein elution: "Flow through mode".

Fig.3C

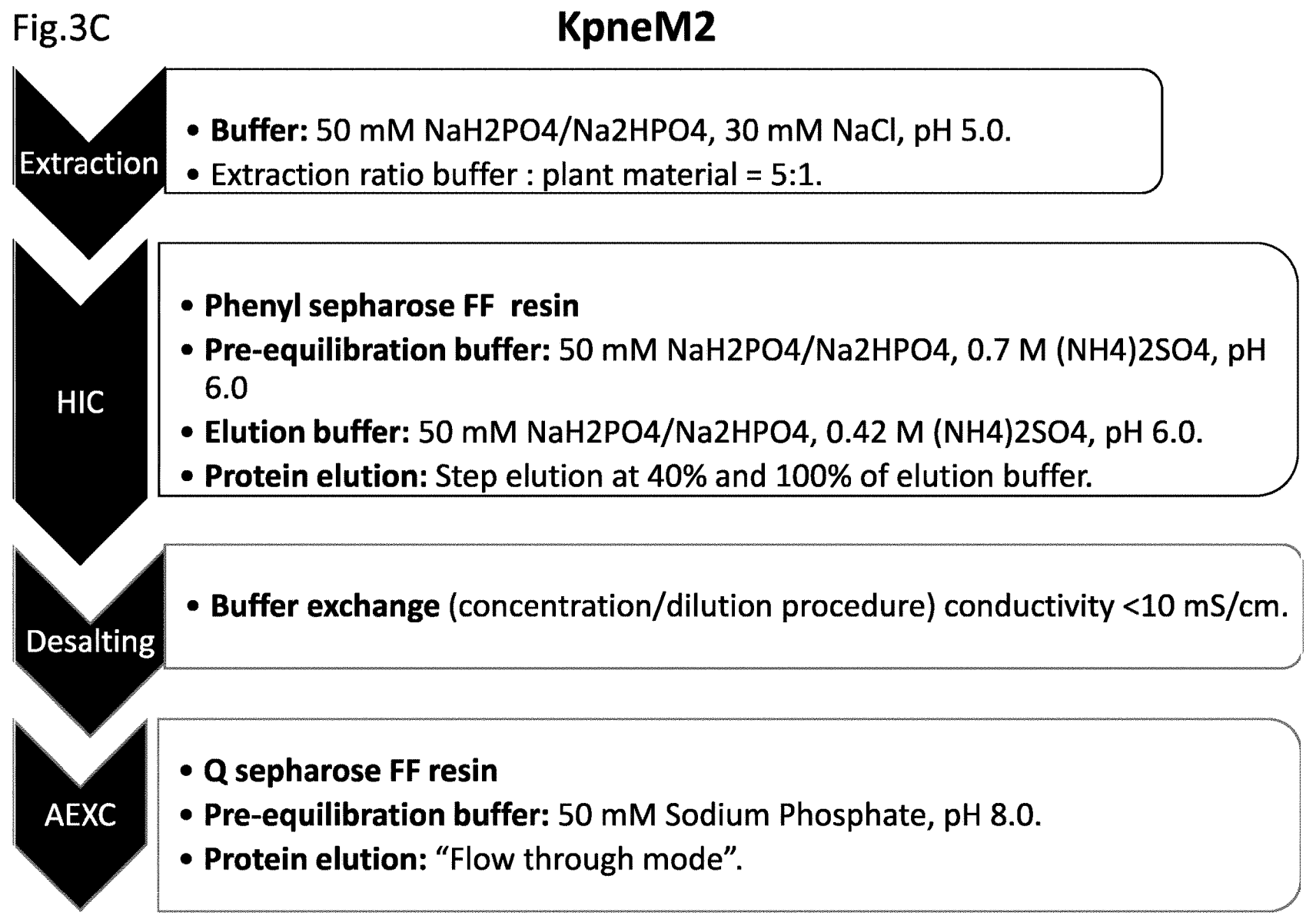

KpneM2

Extraction
- Buffer: 50 mM NaH2PO4/Na2HPO4, 30 mM NaCl, pH 5.0.
- Extraction ratio buffer : plant material = 5:1.

HIC
- Phenyl sepharose FF resin
- Pre-equilibration buffer: 50 mM NaH2PO4/Na2HPO4, 0.7 M (NH4)2SO4, pH 6.0
- Elution buffer: 50 mM NaH2PO4/Na2HPO4, 0.42 M (NH4)2SO4, pH 6.0.
- Protein elution: Step elution at 40% and 100% of elution buffer.

Desalting
- Buffer exchange (concentration/dilution procedure) conductivity <10 mS/cm.

AEXC
- Q sepharose FF resin
- Pre-equilibration buffer: 50 mM Sodium Phosphate, pH 8.0.
- Protein elution: "Flow through mode".

KpneM2

Fig.3E

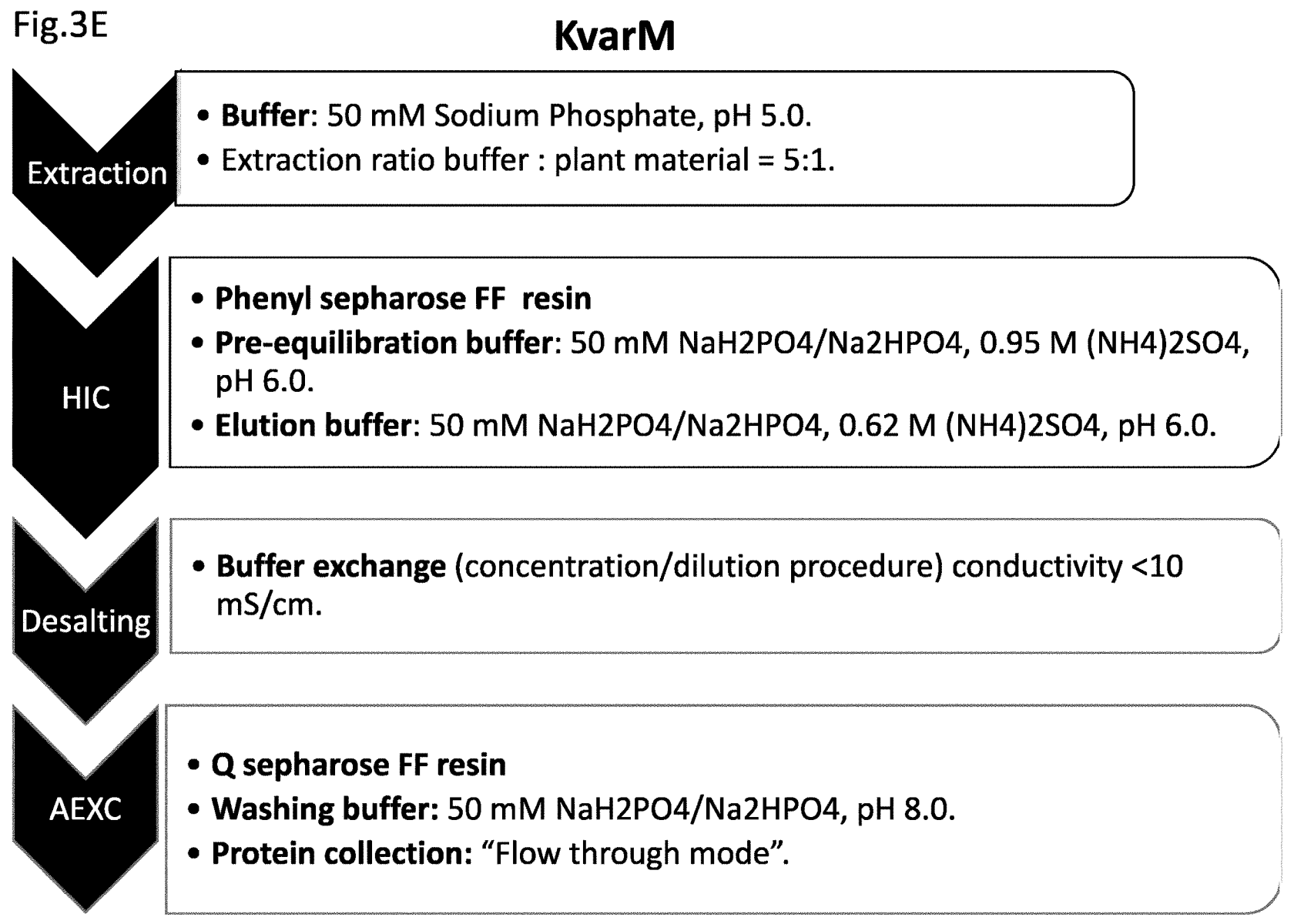

KvarM

Extraction
- Buffer: 50 mM Sodium Phosphate, pH 5.0.
- Extraction ratio buffer : plant material = 5:1.

HIC
- Phenyl sepharose FF resin
- Pre-equilibration buffer: 50 mM $NaH_2PO_4/Na_2HPO_4$, 0.95 M $(NH_4)_2SO_4$, pH 6.0.
- Elution buffer: 50 mM $NaH_2PO_4/Na_2HPO_4$, 0.62 M $(NH_4)_2SO_4$, pH 6.0.

Desalting
- Buffer exchange (concentration/dilution procedure) conductivity <10 mS/cm.

AEXC
- Q sepharose FF resin
- Washing buffer: 50 mM $NaH_2PO_4/Na_2HPO_4$, pH 8.0.
- Protein collection: "Flow through mode".

Fig.3G

KpneA

Extraction
- Buffer: 20 mM NaH2PO4/Na2HPO4, 30 mM NaCl, pH 5.0.
- Extraction ratio buffer: plant material=5:1.

HIC
- Phenyl sepharose FF resin
- Pre-equilibration buffer: 50 mM NaH2PO4/Na2HPO4, 1.50 M (NH4)2SO4, pH 6.0.
- Elution buffer: 50 mM NaH2PO4/Na2HPO4, 0.90 M (NH4)2SO4, pH 6.0

Desalting
- Buffer exchange (concentration/dilution procedure) conductivity <9 mS/cm.

CEXC
- SP sepharose FF resin
- Pre-equilibration buffer: 20 mM NaH2PO4/Na2HPO4, 20 mM Citric acid, pH 4.5.
- Elution buffer: 20 mM NaH2PO4/Na2HPO4, 0.5 NaCl, 20 mM Citric acid, pH 4.5.

KpneA

Fig.3I

KaerA

Extraction
- Buffer: 20 mM NaH2PO4/Na2HPO4, 20 mM Citric acid, pH 5.0.
- Extraction ratio buffer: plant material=5:1.

CEXC
- SP sepharose FF  resin
- Pre-equilibration buffer: 20 mM NaH2PO4/Na2HPO4, 20 mM Citric acid, pH 4.5.
- Elution buffer : 20 mM NaH2PO4/Na2HPO4, 20 mM Citric acid, 0.5 M NaCl, pH 4.5,
- Protein elution: linear gradient elution 0%-50% of elution buffer.

Desalting
- Buffer exchange (concentration/dilution procedure) conductivity <8 mS/cm.

AEXC
- Q sepharose FF resin
- Pre-equilibration buffer: 20 mM NaH2PO4/Na2HPO4, pH 8.0.
- Protein collection: "Flow through mode".

Fig.3K

Kvarla

Extraction
- Buffer: 20 mM NaH2PO4/Na2HPO4, 30 mM NaCl, pH 5.0
- Extraction ratio buffer: plant material=5:1.

HIC
- Phenyl sepharose FF resin.
- Pre-equilibration buffer: 50 mM NaH2PO4/Na2HPO4, 1.35 M (NH4)2SO4, pH 6.0.
- Elution buffer: 50 mM NaH2PO4/Na2HPO4, 0.81 M (NH4)2SO4, pH 6.0.

Desalting
- Buffer exchange (concentration/dilution procedure) conductivity <8 mS/cm.

CEXC
- SP sepharose FF resin
- Pre-equilibration buffer: 20 mM NaH2PO4/Na2HPO4, 20 mM Citric acid, pH 4.5
- Elution buffer: 20 mM NaH2PO4/Na2HPO4, 20 mM Citric acid, 0.5 M NaCl, pH 4.5

Kvarla

KpneM, KpneM2 and Kvarla activity at -20 °C

SEQUENCE LISTING

<160> NUMBER OF SEQ ID NOS: 58

<210> SEQ ID NO 1
<211> LENGTH: 278
<212> TYPE: PRT
<213> ORGANISM: Artificial Sequence
<220> FEATURE:
<223> OTHER INFORMATION: referred to as KpneM (K. pneumoniae EWD35590.1)

<400> SEQUENCE: 1

Met Ser Glu Thr Met Val Val Val Ala Thr Pro Thr Gly Phe Glu Pro
1               5                   10                  15

Ala Gly Tyr Gly Gly Gly Leu Phe Ser Pro Ser Thr Pro Asn His Ser
            20                  25                  30

Pro Ser Gln Gly Gln Ile Phe Leu Gln Val Thr Leu Pro Tyr Tyr Gln
        35                  40                  45

-continued

```
Ser Thr Lys Phe Cys Gln Asp Ser Met Ala Trp Leu Ala Gln Tyr Val
    50                  55                  60

Lys Thr His Gly Ala Gln Asp Pro Leu Thr Ile Gln Val Val Ala Asn
65                  70                  75                  80

Asn Ile Arg Tyr Phe Leu Asn Ala Asp Thr Asn Leu Cys His Asn Pro
                85                  90                  95

Lys Gln Asn Val Trp Glu Ala Phe His Ser Glu Met Thr His Ser Gly
            100                 105                 110

Pro Pro Pro Ala Lys Tyr Asp Tyr His Ser Met Ser Leu Lys Gln Met
            115                 120                 125

Ser Gly Asn Val Val Thr Pro Ala Ala Ala Phe Gly His Tyr Leu Trp
    130                 135                 140

Gly Asn Gly Glu Ala Arg Tyr Val Asn Leu Pro Asp Val Gly Leu Lys
145                 150                 155                 160

Ile Thr Pro Gln Met Ile Pro Glu Leu Met Asn Ile Val Asn Ser Gly
                165                 170                 175

Val Thr Gly His Ile Pro Val Asp Ile Lys Phe Val His Asp Thr Ser
            180                 185                 190

Val Ser Gly Gly Ile Val Pro Ala Ala Tyr Leu Gly His Ile Thr Leu
            195                 200                 205

Arg Thr Glu Gly Thr Leu Asp Ile Gln Ser Gly Gly Ala Trp Thr Tyr
    210                 215                 220

Asn Gly Val Ala Arg Ala Phe Asn Asp Thr Tyr Asp Phe Asn Leu Gly
225                 230                 235                 240

Asp Phe Arg Gly Pro Ile Ala Glu Ser Met Thr Phe Leu Gly Ser Gln
                245                 250                 255

Phe Thr Gly Lys Gln Tyr Glu Ile Ser Met Pro Gly Gln Ile Asn Ile
            260                 265                 270

Ser Gly Ser Gly Arg Arg
            275
```

```
<210> SEQ ID NO 2
<211> LENGTH: 276
<212> TYPE: PRT
<213> ORGANISM: Artificial Sequence
<220> FEATURE:
<223> OTHER INFORMATION: referred to as KvarM (K. variicola CTQ17225.1)

<400> SEQUENCE: 2
```

```
Met Ser Asp Thr Met Ile Val Val Ala Thr Pro Thr Pro Gly Phe Ser
1               5                   10                  15

Tyr Ala Ser Gly Leu Thr Tyr Gly Gly Gly Ala Phe Ala Gly Ala Pro
            20                  25                  30

Ala Asn Gly Pro Ser Glu Gly Gln Ile Phe Phe Gln Thr Val Leu Pro
            35                  40                  45

Ala Tyr Gln Ser Pro Asn Leu Cys Ile Gly Gln Leu Ala Trp Met Thr
    50                  55                  60

Asp Tyr Ile Asn Lys Asn Gly Val Gly Asn Pro Lys Thr Trp Glu Val
65                  70                  75                  80

Ile Ser Gln Asn Val Leu Ile Phe Cys Ser Ala Asp Thr Ala Leu Val
                85                  90                  95

Leu Asn Pro Arg Ile Ala Val Tyr Asp Gly Phe His Lys Thr Lys Trp
            100                 105                 110

Ala Pro Ala Lys Phe Asn Phe Lys Thr Gln Ser Gln Glu Lys Phe Ser
            115                 120                 125
```

-continued

```
Gly Asn Val Thr Thr Pro Ile Ala Ala Phe Gly His Tyr Leu Trp Gly
    130             135             140

Glu Gly Lys Pro Arg Thr Val Asp Leu Ser Ser Val Gly Leu Lys Ile
145             150             155             160

Gln Ala Asn Gln Ile Asp Pro Val Met Ile Ala Val Lys Asn Asn Ala
                165             170             175

Ala Gly Thr Tyr Gln Ile Ser Gly Asn Phe Asn Arg Asn Thr Phe Ile
                180             185             190

Asp Gly Asp Ile Pro Gly Leu Tyr Leu Gly Asn Ile Thr Met Lys Thr
                195             200             205

Glu Gly Thr Leu Lys Ile Asp Ala Lys Gly Asn Trp Asn Tyr Asn Gly
    210             215             220

Val Val Arg Ala Phe Asn Asp Thr Tyr Asp Ala Asn Pro Ser Thr His
225             230             235             240

Arg Ser Lys Ser Ala Glu Asp Leu Thr Thr Leu Leu Arg Leu Thr Gln
                245             250             255

Gly Thr Pro Tyr Glu Ile Arg Ile Pro Gly Glu Leu Lys Val Ser Gly
                260             265             270

Ser Gly Lys Lys
            275
```

<210> SEQ ID NO 3
<211> LENGTH: 272
<212> TYPE: PRT
<213> ORGANISM: Artificial Sequence
<220> FEATURE:
<223> OTHER INFORMATION: referred to as KpneM2 (Klebsiella sp.
      WP_047066220)

<400> SEQUENCE: 3

```
Met Ser Glu Thr Leu Val Val Val Ala Pro Ala Pro Ser Ala Pro Ser
1               5               10              15

Met Thr Tyr Gly Gly Gly Leu Ile Tyr Ser Ser Ile Pro Ser Gly Pro
                20              25              30

Asn Glu Gly Gln Ile Phe Phe Gln Thr Val Leu Pro Ala Tyr Ser Ser
            35              40              45

Pro Asn Phe Cys Thr Asp Arg Leu Arg Trp Met Val Lys Phe Ile Asn
    50              55              60

Glu Asn Gly Val Gly Asn Pro Asp Thr Trp Lys Thr Leu Ala Asp Val
65              70              75              80

Ile Arg Tyr Tyr Ala Ser Ala Asp Thr Ala Ile Ser Lys Asn Pro Lys
                85              90              95

Thr Asn Pro Tyr Asp Ala Trp His Lys Cys Pro Trp Pro Pro Ala Ser
                100             105             110

Phe Asp Val Lys Thr Met Ser Val Glu Lys Phe Ser Gly Ser Val Asn
                115             120             125

Thr Pro Ile Val Ala Phe Gly His Tyr Leu Trp Gly Glu Gly Lys Pro
    130             135             140

Arg Ser Val Asp Leu Ser Thr Val Gly Leu Lys Val Gln Ala Asn Gln
145             150             155             160

Ile Asp Pro Val Met Ile Ala Val Lys Ser Tyr Gly Ala Gly Thr Tyr
                165             170             175

Gln Ile Asn Gly Asn Phe Asn Arg Asn Thr Phe Asp Asp Gly Val Ile
                180             185             190

Pro Gly Leu Tyr Leu Gly Asn Ile Thr Leu Lys Thr Glu Gly Thr Leu
    195             200             205
```

```
Lys Ile Glu Lys Asn Gly Ser Trp Asn Tyr Asn Gly Val Ile Arg Ala
    210             215             220
```

```
Phe Asn Asp Thr Tyr Asp Ala Asn Pro Ser Asn His Arg Ser Gln Ala
225             230             235             240
```

```
Ala Glu Asp Leu Thr Thr Leu Leu Arg Ile Thr Gln Gly Thr Pro Tyr
            245             250             255
```

```
Glu Ile Arg Ile Pro Gly Glu Ile Lys Val Ser Gly Ser Gly Lys Lys
            260             265             270
```

<210> SEQ ID NO 4
<211> LENGTH: 266
<212> TYPE: PRT
<213> ORGANISM: Artificial Sequence
<220> FEATURE:
<223> OTHER INFORMATION: referred to as KaerM (K. aerogenes
      WP_015367360.1)

<400> SEQUENCE: 4

```
Met Thr Asp Thr Leu Thr Val Thr Ala Thr Ile Pro Asn Gly Ser Ser
1               5               10              15
```

```
Phe Asn Phe Gln Phe Glu Gly Met Gly Asn Tyr Tyr Ala Ala Gly Ser
            20              25              30
```

```
Ser Thr Trp Asp Asp Pro Ala Met Ala Asp Ala Ala His Leu Tyr Asn
        35              40              45
```

```
Ala Ile Gln Ser Met Glu Asp Gly Ser Phe Thr Lys Ala Leu Phe Ala
    50              55              60
```

```
Asp Trp Leu Gln Phe Asn Ala Lys Gly Arg Glu Asn Ile Pro Met Ile
65              70              75              80
```

```
Asn Ala Arg Phe Ala Thr Met Glu Thr Met Arg Phe Asn Asp Pro Gly
            85              90              95
```

```
Lys Ala Tyr Phe Gln Phe Ala Gln Tyr Asn Glu Tyr Glu Gly His Thr
            100             105             110
```

```
Pro Gly Asn Asn Phe Thr Ser Gly Ala Phe Ala Pro Phe Leu Gly Leu
            115             120             125
```

```
Trp His Tyr Ile Ser Gly Asn Gly Val Glu Thr Ser Leu Asp Ile Thr
    130             135             140
```

```
Thr Ile Gly Leu Thr Phe Asn Gln Ser Asn Leu Thr Pro Val Asn Asp
145             150             155             160
```

```
Ala Leu Lys Ser Gln Pro Pro Gly Asn Tyr Pro Ile Ser Ser Asn Phe
            165             170             175
```

```
Gly Lys Ser Val Ala Glu Asp Asn Leu Tyr Val Ala Ala Leu Leu Gly
            180             185             190
```

```
Arg Ile Ser Met Lys Thr Glu Gly Thr Leu Ser Ile Gly Glu Ser Gly
            195             200             205
```

```
Glu Trp Ser Tyr Asn Gly Val Val Arg Ala Tyr Asn Asp Thr Tyr Asp
    210             215             220
```

```
Ala Asn Phe Asp Pro Ser Arg Gly Val Ile Ala Gln Ala Ser Thr Thr
225             230             235             240
```

```
Val Leu Ser Trp Phe Asn Gly Lys Pro Tyr Pro Ile Ala Leu Pro Gly
            245             250             255
```

```
Glu Ile Pro Val Gln Leu Ser Gly His Arg
            260             265
```

<210> SEQ ID NO 5
<211> LENGTH: 377
<212> TYPE: PRT

<213> ORGANISM: Artificial Sequence
<220> FEATURE:
<223> OTHER INFORMATION: referred to as KpneA (K. pneumoniae SAV78255.1)

<400> SEQUENCE: 5

```
Met Pro Glu Glu Thr Leu Thr Val Val Gly Gly Gly Asn Asn Ser Cys
1               5                   10                  15

Asn Val Ser Trp Gly Gly Gly Asn Gly Asn Asn Gly Gly Ala Gly Tyr
            20                  25                  30

Ser Gly Lys Tyr Gly Gly Thr Ser Tyr Glu Gly Ala Thr Ser Met Leu
        35                  40                  45

Lys Leu Asn Asp Arg Val Leu Ile Gln Leu Tyr Leu Cys Asn Pro Leu
    50                  55                  60

Asn Pro Asp Tyr Ile Gly Ala Pro Trp Gly Ser Asp Lys Asp Ala Glu
65                  70                  75                  80

Ser Ile Ile Arg Ala Asn Arg Asp Lys Pro Gly Lys Phe Lys Ala Asn
                85                  90                  95

Ile Gln Asn Trp Lys Thr Ser Gly Thr Gly Ser Leu Gly Ser Pro Val
            100                 105                 110

Val Gly Lys Ser Tyr Ser Ser Gly Asp Val Asp Thr Tyr Ser Val Ser
        115                 120                 125

Phe Gly Lys Glu Lys Tyr Asn Val Leu Tyr Asn Arg Lys Lys Asp Ser
    130                 135                 140

Phe Thr Thr Ala Tyr Val Asp Gly Gly Ala Asn Lys Pro Glu His Ser
145                 150                 155                 160

Met Lys Asp Gln Ala Ile Ala Val Val Lys Leu Tyr Leu Leu Asn Glu
                165                 170                 175

Ser Gln Ala Ser Val Ile Asp Thr Thr Ser Gly Ile Ile Thr Asp Ser
            180                 185                 190

Gly Lys Thr Leu Ser Gly Lys Leu Gly Asp Lys Tyr Asn Thr Leu Ala
        195                 200                 205

Arg Glu Ala Ala Asp Asn Ile Lys Asn Phe Gln Gly Lys Lys Leu Arg
    210                 215                 220

Ser Phe Asn Asp Ala Met Ala Ser Ile Asn Glu Leu Ala Asn Asn Pro
225                 230                 235                 240

Lys Met Lys Leu Ser Gln Ala Asp Lys Thr Val Val Ser Asn Ala Leu
                245                 250                 255

Lys Gln Met Asp Leu Ser Ala Leu Ala Asp Arg Phe Lys Gly Leu Glu
            260                 265                 270

Lys Ala Phe Thr Trp Gly Asp Arg Leu Leu Lys Ala Glu Lys Ile Arg
        275                 280                 285

Asp Gly Val Val Thr Gly Val Thr Thr Gly Asp Trp Gln Lys Leu Ala
    290                 295                 300

Phe Glu Val Glu Ala Met Tyr Leu Ser Gly Val Ala Gly Ala Val Ala
305                 310                 315                 320

Leu Gly Ile Thr Thr Ala Met Ile Ser Thr Val Ala Val Ala Leu Ser
                325                 330                 335

Leu Pro Ser Val Ala Val Ser Ala Leu Thr Val Val Ala Val Ile Gly
            340                 345                 350

Ile Ser Ile Leu Thr Ser Tyr Ile Asp Ala Asp Lys Ala Lys Ala Leu
        355                 360                 365

Asn Asn Ala Val Leu Gly Leu Phe Lys
    370                 375
```

```
<210> SEQ ID NO 6
<211> LENGTH: 379
<212> TYPE: PRT
<213> ORGANISM: Artificial Sequence
<220> FEATURE:
<223> OTHER INFORMATION: referred to as KaerA (K. aerogenes
      WP_063414841.1)

<400> SEQUENCE: 6

Met Ala Asn Glu Asp Ser Met Thr Val Asn Gly Asn Ala Gly Ser Gly
1               5                   10                  15

Val His Trp Gly Gly Gly Ser Gly Asn Gly Asn Asn Gly Gly Ala Gly
                20                  25                  30

Ser Asn Gly Gly Ala Asn Val Ala Leu Gly Gly Thr Met Glu Val Glu
            35                  40                  45

Leu Gly Asn Gly Phe Thr Met Ile Val Asp Gly Thr His Pro Ile Asn
    50                  55                  60

Pro Gly Ile Gly Gly Ala Pro Trp Ser Asp Asp Lys Ser Asn Lys Ser
65                  70                  75                  80

Ala Val Asp Ala Leu Asn Ala Asn Lys Ser Lys Pro Ala Lys Phe Lys
                85                  90                  95

Ala Asn Ile Gln Asn Tyr Lys Ser Gly Thr Gln Gly Ser Leu Asn Ser
            100                 105                 110

Pro Ala Val Asn Lys Ser Ser Ser Ser Gly Asp Val Asp Thr Tyr Ala
            115                 120                 125

Val Ser Phe Gly Lys Glu Lys Tyr Asn Val Met Tyr Asn Arg Lys Lys
    130                 135                 140

Asp Ser Phe Thr Ser Gly Tyr Val Asp Gly Gly Ala Thr Lys Pro Glu
145                 150                 155                 160

His Ser Met Lys Asp Gln Ala Ile Ala Val Val Gln Leu Tyr Leu Leu
                165                 170                 175

Asn Glu Lys Glu Lys Asp Val Ile Thr Thr Ala Ala Glu Ile Ile Ser
            180                 185                 190

Ser Ser Gly Glu Thr Ile Ser Gly Lys Leu Gly Glu Lys Tyr Lys Gly
            195                 200                 205

Leu Ala Gln Gly Val Ala Asn Asp Ile Arg Asn Phe Gln Gly Lys Lys
    210                 215                 220

Ile Arg Ser Phe Lys Asp Ala Met Ser Ser Leu Glu Gln Phe Thr Lys
225                 230                 235                 240

Asn Pro Asn Met Lys Leu Asn Gln Ala Asp Lys Ala Ala Leu Val Asn
                245                 250                 255

Ala Leu Asn Gln Val Asn Leu Ser Thr Leu Ala Asp Arg Phe Lys Gly
            260                 265                 270

Leu Glu Arg Ala Phe Thr Trp Ala Asp Arg Leu Leu Lys Ala Gln Lys
            275                 280                 285

Ile Lys Asp Gly Val Val Thr Gly Val Thr Thr Gly Asn Trp Gln Pro
    290                 295                 300

Leu Ala Leu Glu Val Glu Ala Met Tyr Leu Ser Gly Val Ala Gly Ser
305                 310                 315                 320

Val Ala Leu Gly Ile Val Thr Gly Met Ile Ser Gly Leu Ala Ala Leu
                325                 330                 335

Ile Ser Ile Pro Ala Leu Ala Val Thr Ala Leu Thr Val Thr Ala Val
            340                 345                 350

Ile Gly Ile Ala Ile Ala Thr Ser Tyr Ile Asn Ala Asp Thr Ala Lys
            355                 360                 365
```

-continued

```
Ala Leu Asn Asn Ala Val Ala Asp Leu Phe Lys
    370             375

<210> SEQ ID NO 7
<211> LENGTH: 452
<212> TYPE: PRT
<213> ORGANISM: Artificial Sequence
<220> FEATURE:
<223> OTHER INFORMATION: referred to as Koxy (K. oxytoca WP_024273778)

<400> SEQUENCE: 7

Met Ala Gly Phe Ser Tyr Gly Gly Phe Gly Asp Gly Thr Thr Trp Ser
1               5                   10                  15

Lys Glu Arg Gly Thr Gly Pro Leu Pro Gly Gly Gly Ser Ser Gly Asn
            20                  25                  30

Ser Gly Asn His Ser Asn Thr Thr Pro Ala Glu Gln Lys Gln Ile Asn
        35                  40                  45

Ala Ile Arg Ala Asp Lys Asn Val Arg Ala Arg Leu Ser Asn Leu Ile
    50                  55                  60

Lys Ala Ala Arg Lys Leu Asn Pro Ser Val Lys Ile Thr Val His Ala
65                  70                  75                  80

Ile Ser Pro Glu Gly Thr Met Ala Ile Ser Met Glu Gly Leu Thr Ala
                85                  90                  95

Thr Gln Ala Arg Gln Ala Gly Leu Thr Gly Leu Val Met Gly Ile Thr
            100                 105                 110

Val Pro Gly Tyr Ile Gly Ser Val Gly Asp Phe Glu Thr Gly His Lys
            115                 120                 125

Tyr Asn Leu Lys Asn Pro Glu Lys Leu Asn Ser Ile Gly Val Gly Thr
        130                 135                 140

Pro Leu Asp Gly Phe Asn Gly Gly Glu Asn Ile Asp Thr Thr Pro Lys
145                 150                 155                 160

Lys Tyr Arg Asn Trp Arg Ala Thr Asp Glu Lys Ser Phe Tyr Tyr Val
            165                 170                 175

Gly Thr Thr Val Pro Met Arg Leu Leu His His Leu Thr Val Ser Arg
            180                 185                 190

Asn Lys Glu Thr Asp Thr Tyr Thr Met Tyr Phe Lys Ala Lys Asp Ile
        195                 200                 205

Lys Ala Leu Tyr Lys Ile Glu Val Lys Asn Gly Asp Leu Asp Asn Met
    210                 215                 220

Lys Leu Thr Thr Leu Ala Gln Gly His Pro Leu Phe Thr Ala Glu Phe
225                 230                 235                 240

Ala Lys Asp Ile Val Arg Asn Phe Ala Ser Val Lys Asn Glu Ser Asp
                245                 250                 255

Lys Glu Val Leu Asp Lys Thr Ser Gly Val Ile Ile Ser Val Gly Asp
            260                 265                 270

Lys Ala Gly Ala Leu Leu Gly Glu Lys Tyr Lys Ala Leu Ser Arg Glu
            275                 280                 285

Val Ala Ser Asn Ile Gln Asn Phe Gln Gly Lys Gln Ile Arg Thr Tyr
    290                 295                 300

Asp Gln Ala Met Ala Ser Met Asn Lys Leu Met Thr Asn Pro Asn Met
305                 310                 315                 320

Lys Ile Lys Ala Ala Asp Lys Thr Ala Val Ile Asn Ala Trp Lys Ala
                325                 330                 335

Phe Asn Val Glu Asp Met Gly Asn Lys Phe Thr Ala Leu Gly Arg Ala
            340                 345                 350
```

Phe Lys Val Ala Asp Tyr Val Thr Lys Gly Asn Asn Val Arg Glu Lys
            355                 360                 365

Ser Ile Thr Gly Tyr Glu Thr Gly Asn Trp Gly Pro Leu Met Arg Glu
    370                 375                 380

Val Glu Ser Trp Thr Val Ser Gly Leu Thr Ser Ser Val Ala Leu Ala
385                 390                 395                 400

Val Phe Ser Ala Thr Leu Gly Ala Met Leu Val Ala Ala Gly Val Ser
            405                 410                 415

Thr Ala Val Val Gly Ile Ile Gly Ile Ile Ile Ala Gly Leu Ile Gly
            420                 425                 430

Ala Leu Ile Asp Asp Lys Phe Ile Asp Lys Leu Asn Asn Glu Ile Ile
            435                 440                 445

Arg Pro Ala Tyr
    450

<210> SEQ ID NO 8
<211> LENGTH: 466
<212> TYPE: PRT
<213> ORGANISM: Artificial Sequence
<220> FEATURE:
<223> OTHER INFORMATION: referred to as KpneIa (K. pneumoniae BAS34675)

<400> SEQUENCE: 8

Met Pro Gly Phe Asn Tyr Gly Gly Lys Gly Asp Gly Thr Asn Trp Ser
1               5                   10                  15

Ser Glu Arg Gly Thr Gly Pro Glu Pro Gly Gly Gly Ser Arg Gly Asn
            20                  25                  30

Gly Gly Asp Arg Asp Asn Ser Arg Gly Gly Ala Gly Asn Arg Gly Asn
            35                  40                  45

Trp Ala Gly Ser Gly Pro Leu Ser Ala Ala Leu Ile Asn Asp Ser Ile
    50                  55                  60

Ala Glu Ala Leu Glu Lys Gln Leu Pro Arg Asn Thr Val Glu Ala Thr
65                  70                  75                  80

Ser Thr Pro Ala Tyr Lys Lys Met Arg Ala Ala Phe Asp Ala Leu Pro
            85                  90                  95

Leu Asp Lys Gln Pro Glu Ala Arg Ala Gln Ile Thr Lys Ala Trp Gln
            100                 105                 110

Ser Ala His Asp Ala Met Pro Asp Lys Thr Thr Thr Glu Asn Val
            115                 120                 125

Gly Gly Gly Lys Asn Gly His Asn Val Thr Arg Ser Thr Pro Asn Trp
    130                 135                 140

Leu Lys Glu Lys Met Lys Gly Leu Asn Gln Gln Val Asn Asn Asp Leu
145                 150                 155                 160

Ser Gly Ala Leu Ala Gln His Gln Lys Ala Glu Ala Asp Ala Arg Ala
            165                 170                 175

Lys Ala Glu Ala Ala Ala Lys Ala Lys Ala Glu Ala Glu Ala Lys Ala
            180                 185                 190

Lys Ala Glu Ala Glu Ala Lys Ala Lys Ala Lys Ala Glu Ala Ala Ala
            195                 200                 205

Lys Ala Lys Ala Glu Ala Glu Ala Lys Ala Lys Ala Glu Ala Glu Ala
    210                 215                 220

Lys Ala Lys Ala Glu Ala Ala Ala Lys Ala Lys Ala Glu Ala Glu Ala
225                 230                 235                 240

Lys Ala Lys Ala Glu Ala Glu Ala Lys Ala Lys Ala Glu Ala Ala Ala
            245                 250                 255

```
Lys Ala Lys Ala Glu Ala Glu Ala Lys Ala Lys Ala Glu Ala Glu Ala
        260                 265                 270

Lys Ala Lys Ala Glu Ala Glu Ala Lys Ala Lys Ala Glu Ala Asp Ala
        275                 280                 285

Val Lys Asp Ala Val Lys Phe Thr Ala Asp Phe Tyr Lys Glu Val Phe
    290                 295                 300

Ser Val Tyr Gly Glu Lys Ala Glu Gln Leu Ala Asn Leu Leu Ala Thr
305                 310                 315                 320

Gln Ala Lys Gly Lys Asn Ile Arg Asn Ile Asp Asp Ala Leu Lys Ala
                325                 330                 335

Tyr Glu Lys His Lys Thr Asn Ile Asn Lys Lys Ile Asn Ala Gln Asp
            340                 345                 350

Arg Ala Ala Ile Ala Lys Ala Leu Glu Ser Val Asp Val Lys Glu Ala
            355                 360                 365

Ala Lys Asn Phe Ala Lys Phe Ser Lys Gly Leu Gly Tyr Val Gly Pro
        370                 375                 380

Thr Met Asp Val Val Asp Leu Val Leu Glu Leu Arg Lys Ala Ile Lys
385                 390                 395                 400

Glu Asp Asn Trp Arg Ser Phe Phe Val Lys Ile Glu Ala Ile Ala Ile
                405                 410                 415

Ser Phe Gly Ala Thr Gln Leu Ala Ala Leu Ala Phe Ala Ser Leu Leu
            420                 425                 430

Gly Ala Pro Val Gly Leu Leu Gly Tyr Ala Leu Ile Met Ala Gly Ile
            435                 440                 445

Gly Ala Leu Val Ser Asp Asp Val Val Asp Ala Ala Asn Lys Ile Ile
        450                 455                 460

Gly Ile
465
```

```
<210> SEQ ID NO 9
<211> LENGTH: 414
<212> TYPE: PRT
<213> ORGANISM: Artificial Sequence
<220> FEATURE:
<223> OTHER INFORMATION: referred to as KvarIa (K. variicola KDL88409)

<400> SEQUENCE: 9

Met Pro Gly Phe Asn Tyr Gly Gly Lys Gly Asp Gly Thr Asn Trp Ser
1               5                   10                  15

Ser Glu Arg Gly Thr Gly Pro Glu Pro Gly Gly Gly Ser Arg Gly Asn
                20                  25                  30

Gly Gly Asp Arg Asp Asn Ser Arg Gly Gly Ala Gly Asn Arg Gly Asn
            35                  40                  45

Trp Ala Gly Ser Gly Pro Leu Ser Ala Ala Leu Ile Asn Asp Ser Ile
    50                  55                  60

Ala Glu Ala Leu Glu Lys Gln Leu Pro Arg Asn Thr Val Glu Ala Thr
65                  70                  75                  80

Ser Thr Pro Ala Tyr Lys Lys Met Arg Ala Ala Phe Asp Ala Leu Pro
                85                  90                  95

Leu Asp Lys Gln Pro Glu Ala Arg Ala Gln Ile Thr Lys Ala Trp Gln
            100                 105                 110

Ser Ala His Asp Ala Met Pro Asp Arg Thr Thr Thr Glu Asn Val
        115                 120                 125

Gly Gly Gly Lys Asn Gly His Asn Val Thr Arg Ser Thr Pro Asn Trp
        130                 135                 140
```

```
Leu Lys Glu Lys Met Lys Gly Leu Asn Gln Gln Val Asn Asn Asp Leu
145                 150                 155                 160

Ser Gly Ala Leu Ala Gln His Gln Lys Ala Glu Ala Asp Ala Arg Ala
                165                 170                 175

Lys Ala Glu Ala Ala Ala Lys Ala Lys Ala Ala Ala Lys Ala Lys Ala
                180                 185                 190

Glu Ala Glu Ala Lys Ala Lys Ala Glu Ala Glu Ala Lys Ala Lys Ala
                195                 200                 205

Glu Ala Ala Ala Lys Ala Lys Ala Glu Ala Glu Ala Lys Ala Lys Ala
        210                 215                 220

Glu Ala Glu Ala Lys Ala Lys Ala Glu Ala Asp Ala Val Lys Asp Ala
225                 230                 235                 240

Val Lys Phe Thr Ala Asp Phe Tyr Lys Glu Val Phe Ser Val Tyr Gly
                245                 250                 255

Glu Lys Ala Glu Gln Leu Ala Asn Leu Leu Ala Thr Gln Ala Lys Gly
                260                 265                 270

Lys Asn Ile Arg Asn Ile Asp Asp Ala Leu Lys Ala Tyr Glu Lys His
                275                 280                 285

Lys Thr Asn Ile Asn Lys Lys Ile Asn Ala Gln Asp Arg Ala Ala Ile
        290                 295                 300

Ala Lys Ala Leu Glu Ser Val Asp Val Lys Glu Ala Ala Lys Asn Phe
305                 310                 315                 320

Ala Lys Phe Ser Lys Gly Leu Gly Tyr Val Gly Pro Thr Met Asp Val
                325                 330                 335

Val Asp Leu Val Leu Glu Leu Arg Lys Ala Ile Lys Glu Asp Asn Trp
                340                 345                 350

Arg Thr Phe Phe Val Lys Ile Glu Ala Ile Ala Ile Ser Phe Gly Ala
                355                 360                 365

Thr Gln Leu Ala Ala Leu Ala Phe Ala Ser Leu Leu Gly Ala Pro Val
        370                 375                 380

Gly Leu Leu Gly Tyr Ala Leu Ile Met Ala Gly Ile Gly Ala Leu Val
385                 390                 395                 400

Ser Asp Asp Val Val Asp Ala Ala Asn Lys Ile Ile Gly Ile
                405                 410
```

```
<210> SEQ ID NO 10
<211> LENGTH: 34
<212> TYPE: DNA
<213> ORGANISM: Artificial Sequence
<220> FEATURE:
<223> OTHER INFORMATION: Primer ExbB Eco88I fwd

<400> SEQUENCE: 10
aaactcgggt tgatgaacct gttttttatac gtct                              34

<210> SEQ ID NO 11
<211> LENGTH: 33
<212> TYPE: DNA
<213> ORGANISM: Artificial Sequence
<220> FEATURE:
<223> OTHER INFORMATION: Primer ExbB Eco81I rev

<400> SEQUENCE: 11
aaacctgagg tcaacctacc cgtaatttct gcg                               33

<210> SEQ ID NO 12
<211> LENGTH: 34
<212> TYPE: DNA
```

-continued

```
<213> ORGANISM: Artificial Sequence
<220> FEATURE:
<223> OTHER INFORMATION: Primer ExbB Eco88I fwd

<400> SEQUENCE: 12
aaactcgggt tgatgaacct gttttttatac gtct                                  34

<210> SEQ ID NO 13
<211> LENGTH: 31
<212> TYPE: DNA
<213> ORGANISM: Artificial Sequence
<220> FEATURE:
<223> OTHER INFORMATION: Primer ExbD Eco81I rev

<400> SEQUENCE: 13
aaacctgagg ttatttggct ttgacggtct c                                      31

<210> SEQ ID NO 14
<211> LENGTH: 32
<212> TYPE: DNA
<213> ORGANISM: Artificial Sequence
<220> FEATURE:
<223> OTHER INFORMATION: Primer FhuA Eco81I fwd

<400> SEQUENCE: 14
aaacctcagg tttaagccct aagaccagac cc                                     32

<210> SEQ ID NO 15
<211> LENGTH: 32
<212> TYPE: DNA
<213> ORGANISM: Artificial Sequence
<220> FEATURE:
<223> OTHER INFORMATION: Primer FhuA Eco 81I rev

<400> SEQUENCE: 15
aaacctgagg ttagaaacgg aaggtggcgg tg                                     32

<210> SEQ ID NO 16
<211> LENGTH: 31
<212> TYPE: DNA
<213> ORGANISM: Artificial Sequence
<220> FEATURE:
<223> OTHER INFORMATION: Primer FimB Eco88I fwd

<400> SEQUENCE: 16
aaactcgggg ctcccgtagc aaataaaaac g                                      31

<210> SEQ ID NO 17
<211> LENGTH: 31
<212> TYPE: DNA
<213> ORGANISM: Artificial Sequence
<220> FEATURE:
<223> OTHER INFORMATION: Primer FimB Eco81I rev

<400> SEQUENCE: 17
aaacctgagg ttactgaagc agcgacaggc g                                      31

<210> SEQ ID NO 18
<211> LENGTH: 31
<212> TYPE: DNA
<213> ORGANISM: Artificial Sequence
<220> FEATURE:
<223> OTHER INFORMATION: Primer OmpC Eco88I fwd

<400> SEQUENCE: 18
aaactcgggc ttgtggctga acgactcatc a                                      31
```

```
<210> SEQ ID NO 19
<211> LENGTH: 32
<212> TYPE: DNA
<213> ORGANISM: Artificial Sequence
<220> FEATURE:
<223> OTHER INFORMATION: Primer OmpC Eco81I rev

<400> SEQUENCE: 19
aaacctgagg ttagaactgg taaaccaggc cc                                              32

<210> SEQ ID NO 20
<211> LENGTH: 36
<212> TYPE: DNA
<213> ORGANISM: Artificial Sequence
<220> FEATURE:
<223> OTHER INFORMATION: Primer TonB PsyI fwd

<400> SEQUENCE: 20
aaagaccggg tcggcaaagc tccttatcaa taaaca                                         36

<210> SEQ ID NO 21
<211> LENGTH: 31
<212> TYPE: DNA
<213> ORGANISM: Artificial Sequence
<220> FEATURE:
<223> OTHER INFORMATION: Primer TonB BseSI rev

<400> SEQUENCE: 21
aaagtgccct cagttaatct cgacgccgtt g                                              31

<210> SEQ ID NO 22
<211> LENGTH: 274
<212> TYPE: PRT
<213> ORGANISM: Artificial Sequence
<220> FEATURE:
<223> OTHER INFORMATION: Consensus M (KpneM2, KvarM, KpneM, KaerM)
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (12)..(19)
<223> OTHER INFORMATION: Xaa can be any naturally occurring amino acid
<220> FEATURE:
<221> NAME/KEY: misc_feature
<222> LOCATION: (28)..(30)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (55)..(55)
<223> OTHER INFORMATION: Xaa can be any naturally occurring amino acid
<220> FEATURE:
<221> NAME/KEY: misc_feature
<222> LOCATION: (57)..(57)
<223> OTHER INFORMATION: Xaa can be any naturally occurring amino acid
<220> FEATURE:
<221> NAME/KEY: misc_feature
<222> LOCATION: (67)..(67)
<223> OTHER INFORMATION: Xaa can be any naturally occurring amino acid
<220> FEATURE:
<221> NAME/KEY: misc_feature
<222> LOCATION: (74)..(74)
```

-continued

```
<223> OTHER INFORMATION: Xaa can be any naturally occurring amino acid
<220> FEATURE:
<221> NAME/KEY: misc_feature
<222> LOCATION: (81)..(81)
<223> OTHER INFORMATION: Xaa can be any naturally occurring amino acid
<220> FEATURE:
<221> NAME/KEY: misc_feature
<222> LOCATION: (94)..(95)
<223> OTHER INFORMATION: Xaa can be any naturally occurring amino acid
<220> FEATURE:
<221> NAME/KEY: misc_feature
<222> LOCATION: (99)..(100)
<223> OTHER INFORMATION: Xaa can be any naturally occurring amino acid
<220> FEATURE:
<221> NAME/KEY: misc_feature
<222> LOCATION: (108)..(109)
<223> OTHER INFORMATION: Xaa can be any naturally occurring amino acid
<220> FEATURE:
<221> NAME/KEY: misc_feature
<222> LOCATION: (115)..(115)
<223> OTHER INFORMATION: Xaa can be any naturally occurring amino acid
<220> FEATURE:
<221> NAME/KEY: misc_feature
<222> LOCATION: (117)..(118)
<223> OTHER INFORMATION: Xaa can be any naturally occurring amino acid
<220> FEATURE:
<221> NAME/KEY: misc_feature
<222> LOCATION: (122)..(122)
<223> OTHER INFORMATION: Xaa can be any naturally occurring amino acid
<220> FEATURE:
<221> NAME/KEY: misc_feature
<222> LOCATION: (130)..(130)
<223> OTHER INFORMATION: Xaa can be any naturally occurring amino acid
<220> FEATURE:
<221> NAME/KEY: misc_feature
<222> LOCATION: (143)..(143)
<223> OTHER INFORMATION: Xaa can be any naturally occurring amino acid
<220> FEATURE:
<221> NAME/KEY: misc_feature
<222> LOCATION: (173)..(174)
<223> OTHER INFORMATION: Xaa can be any naturally occurring amino acid
<220> FEATURE:
<221> NAME/KEY: misc_feature
<222> LOCATION: (179)..(179)
<223> OTHER INFORMATION: Xaa can be any naturally occurring amino acid
<220> FEATURE:
<221> NAME/KEY: misc_feature
<222> LOCATION: (190)..(190)
<223> OTHER INFORMATION: Xaa can be any naturally occurring amino acid
<220> FEATURE:
<221> NAME/KEY: misc_feature
<222> LOCATION: (193)..(193)
<223> OTHER INFORMATION: Xaa can be any naturally occurring amino acid
<220> FEATURE:
<221> NAME/KEY: misc_feature
<222> LOCATION: (196)..(197)
<223> OTHER INFORMATION: Xaa can be any naturally occurring amino acid
<220> FEATURE:
<221> NAME/KEY: misc_feature
<222> LOCATION: (204)..(204)
<223> OTHER INFORMATION: Xaa can be any naturally occurring amino acid
<220> FEATURE:
<221> NAME/KEY: misc_feature
<222> LOCATION: (213)..(215)
<223> OTHER INFORMATION: Xaa can be any naturally occurring amino acid
<220> FEATURE:
<221> NAME/KEY: misc_feature
<222> LOCATION: (217)..(217)
<223> OTHER INFORMATION: Xaa can be any naturally occurring amino acid
<220> FEATURE:
<221> NAME/KEY: misc_feature
<222> LOCATION: (237)..(237)
<223> OTHER INFORMATION: Xaa can be any naturally occurring amino acid
<220> FEATURE:
<221> NAME/KEY: misc_feature
<222> LOCATION: (240)..(241)
<223> OTHER INFORMATION: Xaa can be any naturally occurring amino acid
<220> FEATURE:
<221> NAME/KEY: misc_feature
```

```
<222> LOCATION: (251)..(253)
<223> OTHER INFORMATION: Xaa can be any naturally occurring amino acid
<220> FEATURE:
<221> NAME/KEY: misc_feature
<222> LOCATION: (256)..(256)
<223> OTHER INFORMATION: Xaa can be any naturally occurring amino acid
<220> FEATURE:
<221> NAME/KEY: misc_feature
<222> LOCATION: (274)..(274)
<223> OTHER INFORMATION: Xaa can be any naturally occurring amino acid

<400> SEQUENCE: 22

Met Ser Xaa Thr Xaa Val Val Val Ala Thr Pro Xaa Xaa Xaa Xaa Xaa
1               5                   10                  15

Xaa Xaa Xaa Thr Tyr Gly Gly Gly Leu Phe Tyr Xaa Xaa Xaa Pro Xaa
            20                  25                  30

Gly Pro Ser Glu Gly Gln Ile Phe Phe Gln Thr Val Leu Pro Ala Tyr
        35                  40                  45

Gln Ser Pro Asn Phe Cys Xaa Asp Xaa Leu Ala Trp Met Ala Asp Tyr
    50                  55                  60

Ile Asn Xaa Asn Gly Val Gly Asn Pro Xaa Thr Trp Glu Val Ile Ala
65                  70                  75                  80

Xaa Asn Ile Arg Tyr Phe Ala Ser Ala Asp Thr Ala Leu Xaa Xaa Asn
                85                  90                  95

Pro Lys Xaa Xaa Val Tyr Asp Ala Phe His Lys Xaa Xaa Trp Pro Pro
            100                 105                 110

Ala Lys Xaa Asp Xaa Xaa Thr Met Ser Xaa Glu Lys Phe Ser Gly Asn
        115                 120                 125

Val Xaa Thr Pro Ile Ala Ala Phe Gly His Tyr Leu Trp Gly Xaa Gly
    130                 135                 140

Lys Pro Arg Ser Val Asp Leu Ser Thr Val Gly Leu Lys Ile Gln Ala
145                 150                 155                 160

Asn Gln Ile Asp Pro Val Met Ile Ala Val Lys Ser Xaa Xaa Ala Gly
                165                 170                 175

Thr Tyr Xaa Ile Ser Gly Asn Phe Asn Arg Asn Thr Phe Xaa Asp Gly
        180                 185                 190

Xaa Ile Pro Xaa Xaa Tyr Leu Gly Asn Ile Thr Xaa Lys Thr Glu Gly
        195                 200                 205

Thr Leu Lys Ile Xaa Xaa Xaa Gly Xaa Trp Asn Tyr Asn Gly Val Val
    210                 215                 220

Arg Ala Phe Asn Asp Thr Tyr Asp Ala Asn Pro Ser Xaa His Arg Xaa
225                 230                 235                 240

Xaa Ile Ala Glu Asp Leu Thr Thr Leu Leu Xaa Xaa Xaa Gln Gly Xaa
                245                 250                 255

Pro Tyr Glu Ile Arg Ile Pro Gly Glu Ile Lys Val Ser Gly Ser Gly
            260                 265                 270

Lys Xaa

<210> SEQ ID NO 23
<211> LENGTH: 382
<212> TYPE: PRT
<213> ORGANISM: Artificial Sequence
<220> FEATURE:
<223> OTHER INFORMATION: Consensus A (KaerA, KpneA)
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
```

```
<222> LOCATION: (5)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (14)..(17)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (23)..(24)
<223> OTHER INFORMATION: Xaa can be any naturally occurring amino acid
<220> FEATURE:
<221> NAME/KEY: misc_feature
<222> LOCATION: (34)..(35)
<223> OTHER INFORMATION: Xaa can be any naturally occurring amino acid
<220> FEATURE:
<221> NAME/KEY: misc_feature
<222> LOCATION: (37)..(38)
<223> OTHER INFORMATION: Xaa can be any naturally occurring amino acid
<220> FEATURE:
<221> NAME/KEY: misc_feature
<222> LOCATION: (40)..(44)
<223> OTHER INFORMATION: Xaa can be any naturally occurring amino acid
<220> FEATURE:
<221> NAME/KEY: misc_feature
<222> LOCATION: (46)..(46)
<223> OTHER INFORMATION: Xaa can be any naturally occurring amino acid
<220> FEATURE:
<221> NAME/KEY: misc_feature
<222> LOCATION: (48)..(51)
<223> OTHER INFORMATION: Xaa can be any naturally occurring amino acid
<220> FEATURE:
<221> NAME/KEY: misc_feature
<222> LOCATION: (53)..(53)
<223> OTHER INFORMATION: Xaa can be any naturally occurring amino acid
<220> FEATURE:
<221> NAME/KEY: misc_feature
<222> LOCATION: (55)..(64)
<223> OTHER INFORMATION: Xaa can be any naturally occurring amino acid
<220> FEATURE:
<221> NAME/KEY: VARIANT
<222> LOCATION: (66)..(66)
<223> OTHER INFORMATION: Leu or Ile
<220> FEATURE:
<221> NAME/KEY: misc_feature
<222> LOCATION: (69)..(71)
<223> OTHER INFORMATION: Xaa can be any naturally occurring amino acid
<220> FEATURE:
<221> NAME/KEY: misc_feature
<222> LOCATION: (76)..(79)
<223> OTHER INFORMATION: Xaa can be any naturally occurring amino acid
<220> FEATURE:
<221> NAME/KEY: misc_feature
<222> LOCATION: (83)..(83)
<223> OTHER INFORMATION: Xaa can be any naturally occurring amino acid
<220> FEATURE:
<221> NAME/KEY: misc_feature
<222> LOCATION: (85)..(87)
<223> OTHER INFORMATION: Xaa can be any naturally occurring amino acid
<220> FEATURE:
<221> NAME/KEY: VARIANT
<222> LOCATION: (88)..(88)
<223> OTHER INFORMATION: Leu or Ile
<220> FEATURE:
<221> NAME/KEY: misc_feature
<222> LOCATION: (89)..(89)
<223> OTHER INFORMATION: Xaa can be any naturally occurring amino acid
<220> FEATURE:
```

-continued

```
<221> NAME/KEY: misc_feature
<222> LOCATION: (92)..(93)
<223> OTHER INFORMATION: Xaa can be any naturally occurring amino acid
<220> FEATURE:
<221> NAME/KEY: misc_feature
<222> LOCATION: (96)..(96)
<223> OTHER INFORMATION: Xaa can be any naturally occurring amino acid
<220> FEATURE:
<221> NAME/KEY: misc_feature
<222> LOCATION: (105)..(105)
<223> OTHER INFORMATION: Xaa can be any naturally occurring amino acid
<220> FEATURE:
<221> NAME/KEY: misc_feature
<222> LOCATION: (107)..(110)
<223> OTHER INFORMATION: Xaa can be any naturally occurring amino acid
<220> FEATURE:
<221> NAME/KEY: misc_feature
<222> LOCATION: (114)..(114)
<223> OTHER INFORMATION: Xaa can be any naturally occurring amino acid
<220> FEATURE:
<221> NAME/KEY: misc_feature
<222> LOCATION: (117)..(117)
<223> OTHER INFORMATION: Xaa can be any naturally occurring amino acid
<220> FEATURE:
<221> NAME/KEY: misc_feature
<222> LOCATION: (119)..(119)
<223> OTHER INFORMATION: Xaa can be any naturally occurring amino acid
<220> FEATURE:
<221> NAME/KEY: misc_feature
<222> LOCATION: (122)..(122)
<223> OTHER INFORMATION: Xaa can be any naturally occurring amino acid
<220> FEATURE:
<221> NAME/KEY: misc_feature
<222> LOCATION: (131)..(131)
<223> OTHER INFORMATION: Xaa can be any naturally occurring amino acid
<220> FEATURE:
<221> NAME/KEY: misc_feature
<222> LOCATION: (142)..(142)
<223> OTHER INFORMATION: Xaa can be any naturally occurring amino acid
<220> FEATURE:
<221> NAME/KEY: misc_feature
<222> LOCATION: (152)..(153)
<223> OTHER INFORMATION: Xaa can be any naturally occurring amino acid
<220> FEATURE:
<221> NAME/KEY: misc_feature
<222> LOCATION: (160)..(160)
<223> OTHER INFORMATION: Xaa can be any naturally occurring amino acid
<220> FEATURE:
<221> NAME/KEY: misc_feature
<222> LOCATION: (175)..(175)
<223> OTHER INFORMATION: Xaa can be any naturally occurring amino acid
<220> FEATURE:
<221> NAME/KEY: misc_feature
<222> LOCATION: (182)..(182)
<223> OTHER INFORMATION: Xaa can be any naturally occurring amino acid
<220> FEATURE:
<221> NAME/KEY: misc_feature
<222> LOCATION: (184)..(185)
<223> OTHER INFORMATION: Xaa can be any naturally occurring amino acid
<220> FEATURE:
<221> NAME/KEY: misc_feature
<222> LOCATION: (188)..(188)
<223> OTHER INFORMATION: Xaa can be any naturally occurring amino acid
<220> FEATURE:
<221> NAME/KEY: misc_feature
<222> LOCATION: (190)..(192)
<223> OTHER INFORMATION: Xaa can be any naturally occurring amino acid
<220> FEATURE:
<221> NAME/KEY: misc_feature
<222> LOCATION: (195)..(196)
<223> OTHER INFORMATION: Xaa can be any naturally occurring amino acid
<220> FEATURE:
<221> NAME/KEY: misc_feature
<222> LOCATION: (199)..(199)
<223> OTHER INFORMATION: Xaa can be any naturally occurring amino acid
<220> FEATURE:
<221> NAME/KEY: VARIANT
<222> LOCATION: (201)..(201)
<223> OTHER INFORMATION: Leu or Ile
```

-continued

```
<220> FEATURE:
<221> NAME/KEY: misc_feature
<222> LOCATION: (207)..(207)
<223> OTHER INFORMATION: Xaa can be any naturally occurring amino acid
<220> FEATURE:
<221> NAME/KEY: misc_feature
<222> LOCATION: (210)..(211)
<223> OTHER INFORMATION: Xaa can be any naturally occurring amino acid
<220> FEATURE:
<221> NAME/KEY: misc_feature
<222> LOCATION: (214)..(216)
<223> OTHER INFORMATION: Xaa can be any naturally occurring amino acid
<220> FEATURE:
<221> NAME/KEY: misc_feature
<222> LOCATION: (221)..(221)
<223> OTHER INFORMATION: Xaa can be any naturally occurring amino acid
<220> FEATURE:
<221> NAME/KEY: VARIANT
<222> LOCATION: (228)..(228)
<223> OTHER INFORMATION: Leu or Ile
<220> FEATURE:
<221> NAME/KEY: misc_feature
<222> LOCATION: (232)..(232)
<223> OTHER INFORMATION: Xaa can be any naturally occurring amino acid
<220> FEATURE:
<221> NAME/KEY: misc_feature
<222> LOCATION: (236)..(236)
<223> OTHER INFORMATION: Xaa can be any naturally occurring amino acid
<220> FEATURE:
<221> NAME/KEY: VARIANT
<222> LOCATION: (238)..(238)
<223> OTHER INFORMATION: Leu or Ile
<220> FEATURE:
<221> NAME/KEY: misc_feature
<222> LOCATION: (239)..(239)
<223> OTHER INFORMATION: Xaa can be any naturally occurring amino acid
<220> FEATURE:
<221> NAME/KEY: misc_feature
<222> LOCATION: (241)..(243)
<223> OTHER INFORMATION: Xaa can be any naturally occurring amino acid
<220> FEATURE:
<221> NAME/KEY: misc_feature
<222> LOCATION: (246)..(246)
<223> OTHER INFORMATION: Xaa can be any naturally occurring amino acid
<220> FEATURE:
<221> NAME/KEY: misc_feature
<222> LOCATION: (250)..(250)
<223> OTHER INFORMATION: Xaa can be any naturally occurring amino acid
<220> FEATURE:
<221> NAME/KEY: misc_feature
<222> LOCATION: (255)..(258)
<223> OTHER INFORMATION: Xaa can be any naturally occurring amino acid
<220> FEATURE:
<221> NAME/KEY: misc_feature
<222> LOCATION: (262)..(262)
<223> OTHER INFORMATION: Xaa can be any naturally occurring amino acid
<220> FEATURE:
<221> NAME/KEY: misc_feature
<222> LOCATION: (264)..(264)
<223> OTHER INFORMATION: Xaa can be any naturally occurring amino acid
<220> FEATURE:
<221> NAME/KEY: misc_feature
<222> LOCATION: (268)..(268)
<223> OTHER INFORMATION: Xaa can be any naturally occurring amino acid
<220> FEATURE:
<221> NAME/KEY: misc_feature
<222> LOCATION: (278)..(278)
<223> OTHER INFORMATION: Xaa can be any naturally occurring amino acid
<220> FEATURE:
<221> NAME/KEY: misc_feature
<222> LOCATION: (283)..(283)
<223> OTHER INFORMATION: Xaa can be any naturally occurring amino acid
<220> FEATURE:
<221> NAME/KEY: misc_feature
<222> LOCATION: (293)..(293)
<223> OTHER INFORMATION: Xaa can be any naturally occurring amino acid
<220> FEATURE:
<221> NAME/KEY: misc_feature
<222> LOCATION: (307)..(307)
```

```
<223> OTHER INFORMATION: Xaa can be any naturally occurring amino acid
<220> FEATURE:
<221> NAME/KEY: misc_feature
<222> LOCATION: (310)..(310)
<223> OTHER INFORMATION: Xaa can be any naturally occurring amino acid
<220> FEATURE:
<221> NAME/KEY: misc_feature
<222> LOCATION: (323)..(323)
<223> OTHER INFORMATION: Xaa can be any naturally occurring amino acid
<220> FEATURE:
<221> NAME/KEY: misc_feature
<222> LOCATION: (329)..(329)
<223> OTHER INFORMATION: Xaa can be any naturally occurring amino acid
<220> FEATURE:
<221> NAME/KEY: misc_feature
<222> LOCATION: (331)..(331)
<223> OTHER INFORMATION: Xaa can be any naturally occurring amino acid
<220> FEATURE:
<221> NAME/KEY: misc_feature
<222> LOCATION: (335)..(336)
<223> OTHER INFORMATION: Xaa can be any naturally occurring amino acid
<220> FEATURE:
<221> NAME/KEY: misc_feature
<222> LOCATION: (338)..(339)
<223> OTHER INFORMATION: Xaa can be any naturally occurring amino acid
<220> FEATURE:
<221> NAME/KEY: VARIANT
<222> LOCATION: (340)..(340)
<223> OTHER INFORMATION: Leu or Ile
<220> FEATURE:
<221> NAME/KEY: VARIANT
<222> LOCATION: (342)..(342)
<223> OTHER INFORMATION: Leu or Ile
<220> FEATURE:
<221> NAME/KEY: misc_feature
<222> LOCATION: (344)..(345)
<223> OTHER INFORMATION: Xaa can be any naturally occurring amino acid
<220> FEATURE:
<221> NAME/KEY: misc_feature
<222> LOCATION: (348)..(348)
<223> OTHER INFORMATION: Xaa can be any naturally occurring amino acid
<220> FEATURE:
<221> NAME/KEY: misc_feature
<222> LOCATION: (353)..(353)
<223> OTHER INFORMATION: Xaa can be any naturally occurring amino acid
<220> FEATURE:
<221> NAME/KEY: misc_feature
<222> LOCATION: (359)..(359)
<223> OTHER INFORMATION: Xaa can be any naturally occurring amino acid
<220> FEATURE:
<221> NAME/KEY: misc_feature
<222> LOCATION: (361)..(361)
<223> OTHER INFORMATION: Xaa can be any naturally occurring amino acid
<220> FEATURE:
<221> NAME/KEY: misc_feature
<222> LOCATION: (369)..(369)
<223> OTHER INFORMATION: Xaa can be any naturally occurring amino acid
<220> FEATURE:
<221> NAME/KEY: misc_feature
<222> LOCATION: (378)..(379)
<223> OTHER INFORMATION: Xaa can be any naturally occurring amino acid

<400> SEQUENCE: 23

Met Xaa Xaa Glu Xaa Xaa Xaa Xaa Val Xaa Gly Xaa Asn Xaa Xaa Xaa
1               5                   10                  15

Xaa Val Xaa Trp Gly Gly Xaa Xaa Gly Asn Gly Asn Asn Gly Gly Ala
            20                  25                  30

Gly Xaa Xaa Gly Xaa Xaa Gly Xaa Xaa Xaa Xaa Xaa Gly Xaa Thr Xaa
        35                  40                  45

Xaa Xaa Xaa Leu Xaa Asx Xaa Xaa Xaa Xaa Xaa Xaa Xaa Xaa Xaa Xaa
    50                  55                  60

Pro Xaa Asn Pro Xaa Xaa Xaa Gly Ala Pro Trp Xaa Xaa Xaa Xaa Ser
65                  70                  75                  80
```

```
Asx Lys Xaa Ala Xaa Xaa Xaa Xaa Ala Asn Xaa Xaa Lys Pro Xaa
            85                  90              95

Lys Phe Lys Ala Asn Ile Gln Asn Xaa Lys Xaa Xaa Xaa Gly Ser
            100             105             110

Leu Xaa Ser Pro Xaa Val Xaa Lys Ser Xaa Ser Ser Gly Asp Val Asp
        115             120             125

Thr Tyr Xaa Val Ser Phe Gly Lys Glu Lys Tyr Asn Val Xaa Tyr Asn
    130             135             140

Arg Lys Lys Asp Ser Phe Thr Xaa Xaa Tyr Val Asp Gly Gly Ala Xaa
145             150             155             160

Lys Pro Glu His Ser Met Lys Asp Gln Ala Ile Ala Val Val Xaa Leu
            165             170             175

Tyr Leu Leu Asn Glu Xaa Glx Xaa Xaa Val Ile Xaa Thr Xaa Xaa Xaa
            180             185             190

Ile Ile Xaa Xaa Ser Gly Xaa Thr Xaa Ser Gly Lys Leu Gly Xaa Lys
            195             200             205

Tyr Xaa Xaa Leu Ala Xaa Xaa Xaa Ala Asx Asx Ile Xaa Asn Phe Gln
    210             215             220

Gly Lys Lys Xaa Arg Ser Phe Xaa Asp Ala Met Xaa Ser Xaa Xaa Glx
225             230             235             240

Xaa Xaa Xaa Asn Pro Xaa Met Lys Leu Xaa Gln Ala Asp Lys Xaa Xaa
            245             250             255

Xaa Xaa Asn Ala Leu Xaa Gln Xaa Asx Leu Ser Xaa Leu Ala Asp Arg
            260             265             270

Phe Lys Gly Leu Glu Xaa Ala Phe Thr Trp Xaa Asp Arg Leu Leu Lys
            275             280             285

Ala Glx Lys Ile Xaa Asp Gly Val Val Thr Gly Val Thr Thr Gly Asx
    290             295             300

Trp Gln Xaa Leu Ala Xaa Glu Val Glu Ala Met Tyr Leu Ser Gly Val
305             310             315             320

Ala Gly Xaa Val Ala Leu Gly Ile Xaa Thr Xaa Met Ile Ser Xaa Xaa
            325             330             335

Ala Xaa Xaa Xaa Ser Xaa Pro Xaa Xaa Ala Val Xaa Ala Leu Thr Val
            340             345             350

Xaa Ala Val Ile Gly Ile Xaa Ile Xaa Thr Ser Tyr Ile Asx Ala Asp
            355             360             365

Xaa Ala Lys Ala Leu Asn Asn Ala Val Xaa Xaa Leu Phe Lys
            370             375             380
```

```
<210> SEQ ID NO 24
<211> LENGTH: 466
<212> TYPE: PRT
<213> ORGANISM: Artificial Sequence
<220> FEATURE:
<223> OTHER INFORMATION: Consensus Ia (KpneIa, KvarIa)
<220> FEATURE:
<221> NAME/KEY: misc_feature
<222> LOCATION: (121)..(121)
<223> OTHER INFORMATION: Xaa can be any naturally occurring amino acid
<220> FEATURE:
<221> NAME/KEY: misc_feature
<222> LOCATION: (186)..(237)
<223> OTHER INFORMATION: Xaa can be any naturally occurring amino acid
<220> FEATURE:
<221> NAME/KEY: misc_feature
<222> LOCATION: (239)..(239)
<223> OTHER INFORMATION: Xaa can be any naturally occurring amino acid
<220> FEATURE:
<221> NAME/KEY: misc_feature
<222> LOCATION: (255)..(255)
```

```
<223> OTHER INFORMATION: Xaa can be any naturally occurring amino acid
<220> FEATURE:
<221> NAME/KEY: misc_feature
<222> LOCATION: (263)..(263)
<223> OTHER INFORMATION: Xaa can be any naturally occurring amino acid
<220> FEATURE:
<221> NAME/KEY: misc_feature
<222> LOCATION: (406)..(406)
<223> OTHER INFORMATION: Xaa can be any naturally occurring amino acid

<400> SEQUENCE: 24

Met Pro Gly Phe Asn Tyr Gly Gly Lys Gly Asp Gly Thr Asn Trp Ser
1               5                   10                  15

Ser Glu Arg Gly Thr Gly Pro Glu Pro Gly Gly Gly Ser Arg Gly Asn
            20                  25                  30

Gly Gly Asp Arg Asp Asn Ser Arg Gly Gly Ala Gly Asn Arg Gly Asn
        35                  40                  45

Trp Ala Gly Ser Gly Pro Leu Ser Ala Ala Leu Ile Asn Asp Ser Ile
    50                  55                  60

Ala Glu Ala Leu Glu Lys Gln Leu Pro Arg Asn Thr Val Glu Ala Thr
65                  70                  75                  80

Ser Thr Pro Ala Tyr Lys Lys Met Arg Ala Ala Phe Asp Ala Leu Pro
                85                  90                  95

Leu Asp Lys Gln Pro Glu Ala Arg Ala Gln Ile Thr Lys Ala Trp Gln
            100                 105                 110

Ser Ala His Asp Ala Met Pro Asp Xaa Thr Thr Thr Thr Glu Asn Val
            115                 120                 125

Gly Gly Gly Lys Asn Gly His Asn Val Thr Arg Ser Thr Pro Asn Trp
        130                 135                 140

Leu Lys Glu Lys Met Lys Gly Leu Asn Gln Gln Val Asn Asn Asp Leu
145                 150                 155                 160

Ser Gly Ala Leu Ala Gln His Gln Lys Ala Glu Ala Asp Ala Arg Ala
                165                 170                 175

Lys Ala Glu Ala Ala Ala Lys Ala Lys Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
            195                 200                 205

Xaa Xaa Xaa Xaa Xaa Xaa Xaa Xaa Xaa Xaa Xaa Xaa Xaa Xaa Xaa Xaa
        210                 215                 220

Xaa Xaa Xaa Xaa Xaa Xaa Xaa Xaa Xaa Xaa Xaa Xaa Ala Xaa Ala
225                 230                 235                 240

Lys Ala Lys Ala Glu Ala Glu Ala Lys Ala Lys Ala Glu Ala Xaa Ala
            245                 250                 255

Lys Ala Lys Ala Glu Ala Xaa Ala Lys Ala Lys Ala Glu Ala Glu Ala
            260                 265                 270

Lys Ala Lys Ala Glu Ala Glu Ala Lys Ala Lys Ala Glu Ala Asp Ala
        275                 280                 285

Val Lys Asp Ala Val Lys Phe Thr Ala Asp Phe Tyr Lys Glu Val Phe
    290                 295                 300

Ser Val Tyr Gly Glu Lys Ala Glu Gln Leu Ala Asn Leu Leu Ala Thr
305                 310                 315                 320

Gln Ala Lys Gly Lys Asn Ile Arg Asn Ile Asp Asp Ala Leu Lys Ala
                325                 330                 335

Tyr Glu Lys His Lys Thr Asn Ile Asn Lys Lys Ile Asn Ala Gln Asp
            340                 345                 350

Arg Ala Ala Ile Ala Lys Ala Leu Glu Ser Val Asp Val Lys Glu Ala
```

-continued

```
                 355              360              365

Ala Lys Asn Phe Ala Lys Phe Ser Lys Gly Leu Gly Tyr Val Gly Pro
     370              375              380

Thr Met Asp Val Val Asp Leu Val Leu Glu Leu Arg Lys Ala Ile Lys
385              390              395              400

Glu Asp Asn Trp Arg Xaa Phe Phe Val Lys Ile Glu Ala Ile Ala Ile
                405              410              415

Ser Phe Gly Ala Thr Gln Leu Ala Ala Leu Ala Phe Ala Ser Leu Leu
         420              425              430

Gly Ala Pro Val Gly Leu Leu Gly Tyr Ala Leu Ile Met Ala Gly Ile
         435              440              445

Gly Ala Leu Val Ser Asp Asp Val Val Asp Ala Ala Asn Lys Ile Ile
     450              455              460

Gly Ile
465

<210> SEQ ID NO 25
<211> LENGTH: 5
<212> TYPE: PRT
<213> ORGANISM: Artificial Sequence
<220> FEATURE:
<223> OTHER INFORMATION: conserved sequence stretch in SEQ ID NO: 22

<400> SEQUENCE: 25

Thr Glu Gly Thr Leu
1               5

<210> SEQ ID NO 26
<211> LENGTH: 4
<212> TYPE: PRT
<213> ORGANISM: Artificial Sequence
<220> FEATURE:
<223> OTHER INFORMATION: conserved sequence stretch in SEQ ID NO: 22

<400> SEQUENCE: 26

Tyr Asn Gly Val
1

<210> SEQ ID NO 27
<211> LENGTH: 8
<212> TYPE: PRT
<213> ORGANISM: Artificial Sequence
<220> FEATURE:
<223> OTHER INFORMATION: conserved sequence stretch in SEQ ID NO: 22

<400> SEQUENCE: 27

Arg Ala Phe Asn Asp Thr Tyr Asp
1               5

<210> SEQ ID NO 28
<211> LENGTH: 9
<212> TYPE: PRT
<213> ORGANISM: Artificial Sequence
<220> FEATURE:
<223> OTHER INFORMATION: conserved sequence stretch in SEQ ID NO: 23

<400> SEQUENCE: 28

Gly Asn Gly Asn Asn Gly Gly Ala Gly
1               5

<210> SEQ ID NO 29
<211> LENGTH: 4
<212> TYPE: PRT
```

-continued

```
<213> ORGANISM: Artificial Sequence
<220> FEATURE:
<223> OTHER INFORMATION: conserved sequence stretch in SEQ ID NO: 23

<400> SEQUENCE: 29

Gly Ala Pro Trp
1

<210> SEQ ID NO 30
<211> LENGTH: 8
<212> TYPE: PRT
<213> ORGANISM: Artificial Sequence
<220> FEATURE:
<223> OTHER INFORMATION: conserved sequence stretch in SEQ ID NO: 23

<400> SEQUENCE: 30

Lys Phe Lys Ala Asn Ile Gln Asn
1               5

<210> SEQ ID NO 31
<211> LENGTH: 8
<212> TYPE: PRT
<213> ORGANISM: Artificial Sequence
<220> FEATURE:
<223> OTHER INFORMATION: conserved sequence stretch in SEQ ID NO: 23

<400> SEQUENCE: 31

Ser Ser Gly Asp Val Asp Thr Tyr
1               5

<210> SEQ ID NO 32
<211> LENGTH: 10
<212> TYPE: PRT
<213> ORGANISM: Artificial Sequence
<220> FEATURE:
<223> OTHER INFORMATION: conserved sequence stretch in SEQ ID NO: 23

<400> SEQUENCE: 32

Val Ser Phe Gly Lys Glu Lys Tyr Asn Val
1               5                   10

<210> SEQ ID NO 33
<211> LENGTH: 9
<212> TYPE: PRT
<213> ORGANISM: Artificial Sequence
<220> FEATURE:
<223> OTHER INFORMATION: conserved sequence stretch in SEQ ID NO: 23

<400> SEQUENCE: 33

Tyr Asn Arg Lys Lys Asp Ser Phe Thr
1               5

<210> SEQ ID NO 34
<211> LENGTH: 6
<212> TYPE: PRT
<213> ORGANISM: Artificial Sequence
<220> FEATURE:
<223> OTHER INFORMATION: conserved sequence stretch in SEQ ID NO: 23

<400> SEQUENCE: 34

Tyr Val Asp Gly Gly Ala
1               5

<210> SEQ ID NO 35
<211> LENGTH: 14
<212> TYPE: PRT
<213> ORGANISM: Artificial Sequence
```

```
<220> FEATURE:
<223> OTHER INFORMATION: conserved sequence stretch in SEQ ID NO: 23

<400> SEQUENCE: 35

Lys Pro Glu His Ser Met Lys Asp Gln Ala Ile Ala Val Val
1               5                   10

<210> SEQ ID NO 36
<211> LENGTH: 6
<212> TYPE: PRT
<213> ORGANISM: Artificial Sequence
<220> FEATURE:
<223> OTHER INFORMATION: conserved sequence stretch in SEQ ID NO: 23

<400> SEQUENCE: 36

Leu Tyr Leu Leu Asn Glu
1               5

<210> SEQ ID NO 37
<211> LENGTH: 5
<212> TYPE: PRT
<213> ORGANISM: Artificial Sequence
<220> FEATURE:
<223> OTHER INFORMATION: conserved sequence stretch in SEQ ID NO: 23

<400> SEQUENCE: 37

Ser Gly Lys Leu Gly
1               5

<210> SEQ ID NO 38
<211> LENGTH: 6
<212> TYPE: PRT
<213> ORGANISM: Artificial Sequence
<220> FEATURE:
<223> OTHER INFORMATION: conserved sequence stretch in SEQ ID NO: 23

<400> SEQUENCE: 38

Asn Phe Gln Gly Lys Lys
1               5

<210> SEQ ID NO 39
<211> LENGTH: 4
<212> TYPE: PRT
<213> ORGANISM: Artificial Sequence
<220> FEATURE:
<223> OTHER INFORMATION: conserved sequence stretch in SEQ ID NO: 23

<400> SEQUENCE: 39

Gln Ala Asp Lys
1

<210> SEQ ID NO 40
<211> LENGTH: 8
<212> TYPE: PRT
<213> ORGANISM: Artificial Sequence
<220> FEATURE:
<223> OTHER INFORMATION: conserved sequence stretch in SEQ ID NO: 23

<400> SEQUENCE: 40

Leu Ala Asp Arg Phe Lys Gly Leu
1               5

<210> SEQ ID NO 41
<211> LENGTH: 4
<212> TYPE: PRT
<213> ORGANISM: Artificial Sequence
<220> FEATURE:
```

-continued

<223> OTHER INFORMATION: conserved sequence stretch in SEQ ID NO: 23

<400> SEQUENCE: 41

Ala Phe Thr Trp
1

<210> SEQ ID NO 42
<211> LENGTH: 6
<212> TYPE: PRT
<213> ORGANISM: Artificial Sequence
<220> FEATURE:
<223> OTHER INFORMATION: conserved sequence stretch in SEQ ID NO: 23

<400> SEQUENCE: 42

Asp Arg Leu Leu Lys Ala
1               5

<210> SEQ ID NO 43
<211> LENGTH: 10
<212> TYPE: PRT
<213> ORGANISM: Artificial Sequence
<220> FEATURE:
<223> OTHER INFORMATION: conserved sequence stretch in SEQ ID NO: 23

<400> SEQUENCE: 43

Asp Gly Val Val Thr Gly Val Thr Thr Gly
1               5                   10

<210> SEQ ID NO 44
<211> LENGTH: 12
<212> TYPE: PRT
<213> ORGANISM: Artificial Sequence
<220> FEATURE:
<223> OTHER INFORMATION: conserved sequence stretch in SEQ ID NO: 23

<400> SEQUENCE: 44

Glu Val Glu Ala Met Tyr Leu Ser Gly Val Ala Gly
1               5                   10

<210> SEQ ID NO 45
<211> LENGTH: 5
<212> TYPE: PRT
<213> ORGANISM: Artificial Sequence
<220> FEATURE:
<223> OTHER INFORMATION: conserved sequence stretch in SEQ ID NO: 23

<400> SEQUENCE: 45

Val Ala Leu Gly Ile
1               5

<210> SEQ ID NO 46
<211> LENGTH: 4
<212> TYPE: PRT
<213> ORGANISM: Artificial Sequence
<220> FEATURE:
<223> OTHER INFORMATION: conserved sequence stretch in SEQ ID NO: 23

<400> SEQUENCE: 46

Ala Leu Thr Val
1

<210> SEQ ID NO 47
<211> LENGTH: 5
<212> TYPE: PRT
<213> ORGANISM: Artificial Sequence
<220> FEATURE:
<223> OTHER INFORMATION: conserved sequence stretch in SEQ ID NO: 23

```
<400> SEQUENCE: 47

Ala Val Ile Gly Ile
1               5

<210> SEQ ID NO 48
<211> LENGTH: 4
<212> TYPE: PRT
<213> ORGANISM: Artificial Sequence
<220> FEATURE:
<223> OTHER INFORMATION: conserved sequence stretch in SEQ ID NO: 23

<400> SEQUENCE: 48

Thr Ser Tyr Ile
1

<210> SEQ ID NO 49
<211> LENGTH: 8
<212> TYPE: PRT
<213> ORGANISM: Artificial Sequence
<220> FEATURE:
<223> OTHER INFORMATION: conserved sequence stretch in SEQ ID NO: 23

<400> SEQUENCE: 49

Ala Lys Ala Leu Asn Asn Ala Val
1               5

<210> SEQ ID NO 50
<211> LENGTH: 120
<212> TYPE: PRT
<213> ORGANISM: Artificial Sequence
<220> FEATURE:
<223> OTHER INFORMATION: conserved sequence stretch in SEQ ID NO: 24

<400> SEQUENCE: 50

Met Pro Gly Phe Asn Tyr Gly Gly Lys Gly Asp Gly Thr Asn Trp Ser
1               5                   10                  15

Ser Glu Arg Gly Thr Gly Pro Glu Pro Gly Gly Gly Ser Arg Gly Asn
            20                  25                  30

Gly Gly Asp Arg Asp Asn Ser Arg Gly Gly Ala Gly Asn Arg Gly Asn
        35                  40                  45

Trp Ala Gly Ser Gly Pro Leu Ser Ala Ala Leu Ile Asn Asp Ser Ile
    50                  55                  60

Ala Glu Ala Leu Glu Lys Gln Leu Pro Arg Asn Thr Val Glu Ala Thr
65                  70                  75                  80

Ser Thr Pro Ala Tyr Lys Lys Met Arg Ala Ala Phe Asp Ala Leu Pro
                85                  90                  95

Leu Asp Lys Gln Pro Glu Ala Arg Ala Gln Ile Thr Lys Ala Trp Gln
            100                 105                 110

Ser Ala His Asp Ala Met Pro Asp
        115                 120

<210> SEQ ID NO 51
<211> LENGTH: 64
<212> TYPE: PRT
<213> ORGANISM: Artificial Sequence
<220> FEATURE:
<223> OTHER INFORMATION: conserved sequence stretch in SEQ ID NO: 24

<400> SEQUENCE: 51

Thr Thr Thr Thr Glu Asn Val Gly Gly Gly Lys Asn Gly His Asn Val
1               5                   10                  15
```

```
Thr Arg Ser Thr Pro Asn Trp Leu Lys Glu Lys Met Lys Gly Leu Asn
              20              25              30

Gln Gln Val Asn Asn Asp Leu Ser Gly Ala Leu Ala Gln His Gln Lys
          35              40              45

Ala Glu Ala Asp Ala Arg Ala Lys Ala Glu Ala Ala Ala Lys Ala Lys
      50              55              60

<210> SEQ ID NO 52
<211> LENGTH: 15
<212> TYPE: PRT
<213> ORGANISM: Artificial Sequence
<220> FEATURE:
<223> OTHER INFORMATION: conserved sequence stretch in SEQ ID NO: 24

<400> SEQUENCE: 52

Ala Lys Ala Lys Ala Glu Ala Glu Ala Lys Ala Lys Ala Glu Ala
1               5               10              15

<210> SEQ ID NO 53
<211> LENGTH: 7
<212> TYPE: PRT
<213> ORGANISM: Artificial Sequence
<220> FEATURE:
<223> OTHER INFORMATION: conserved sequence stretch in SEQ ID NO: 24

<400> SEQUENCE: 53

Ala Lys Ala Lys Ala Glu Ala
1               5

<210> SEQ ID NO 54
<211> LENGTH: 142
<212> TYPE: PRT
<213> ORGANISM: Artificial Sequence
<220> FEATURE:
<223> OTHER INFORMATION: conserved sequence stretch in SEQ ID NO: 24

<400> SEQUENCE: 54

Ala Lys Ala Lys Ala Glu Ala Glu Ala Lys Ala Lys Ala Glu Ala Glu
1               5               10              15

Ala Lys Ala Lys Ala Glu Ala Asp Ala Val Lys Asp Ala Val Lys Phe
              20              25              30

Thr Ala Asp Phe Tyr Lys Glu Val Phe Ser Val Tyr Gly Glu Lys Ala
          35              40              45

Glu Gln Leu Ala Asn Leu Leu Ala Thr Gln Ala Lys Gly Lys Asn Ile
      50              55              60

Arg Asn Ile Asp Asp Ala Leu Lys Ala Tyr Glu Lys His Lys Thr Asn
65              70              75              80

Ile Asn Lys Lys Ile Asn Ala Gln Asp Arg Ala Ala Ile Ala Lys Ala
              85              90              95

Leu Glu Ser Val Asp Val Lys Glu Ala Ala Lys Asn Phe Ala Lys Phe
          100             105             110

Ser Lys Gly Leu Gly Tyr Val Gly Pro Thr Met Asp Val Val Asp Leu
          115             120             125

Val Leu Glu Leu Arg Lys Ala Ile Lys Glu Asp Asn Trp Arg
      130             135             140

<210> SEQ ID NO 55
<211> LENGTH: 60
<212> TYPE: PRT
<213> ORGANISM: Artificial Sequence
<220> FEATURE:
<223> OTHER INFORMATION: conserved sequence stretch in SEQ ID NO: 24
```

-continued

```
<400> SEQUENCE: 55

Phe Phe Val Lys Ile Glu Ala Ile Ala Ile Ser Phe Gly Ala Thr Gln
1               5                   10                  15

Leu Ala Ala Leu Ala Phe Ala Ser Leu Leu Gly Ala Pro Val Gly Leu
            20                  25                  30

Leu Gly Tyr Ala Leu Ile Met Ala Gly Ile Gly Ala Leu Val Ser Asp
        35                  40                  45

Asp Val Val Asp Ala Ala Asn Lys Ile Ile Gly Ile
    50                  55                  60

<210> SEQ ID NO 56
<211> LENGTH: 23
<212> TYPE: DNA
<213> ORGANISM: Artificial Sequence
<220> FEATURE:
<223> OTHER INFORMATION: khe gene amplification forward primer

<400> SEQUENCE: 56
gatgaaacga cctgattgca ttc                                          23

<210> SEQ ID NO 57
<211> LENGTH: 18
<212> TYPE: DNA
<213> ORGANISM: Artificial Sequence
<220> FEATURE:
<223> OTHER INFORMATION: khe gene amplification reverse primer

<400> SEQUENCE: 57
ccgggctgtc gggataag                                                18

<210> SEQ ID NO 58
<211> LENGTH: 19
<212> TYPE: DNA
<213> ORGANISM: Artificial Sequence
<220> FEATURE:
<223> OTHER INFORMATION: khe gene amplification probe sequence

<400> SEQUENCE: 58
cgcgaactgg aagggcccg                                               19
```

KLEBICINS FOR THE CONTROL OF KLEBSIELLA

CROSS-REFERENCE TO RELATED APPLICATIONS

This application is the U.S. National Stage of International Application PCT/EP2020/065652, filed Jun. 5, 2020, which designates the U.S. and was published by the International Bureau in English on Dec. 10, 2020, and which claims the benefit of European Patent Application No. 19 178 676.3, filed Jun. 6, 2019; both of which are hereby incorporated herein in their entirety by reference.

FIELD OF THE INVENTION

The present invention provides proteins having cytotoxic activity against Klebsiella. The invention also provides compositions, including pharmaceutical compositions, comprising one or more of said proteins. The invention further provides a protein having cytotoxic activity against Klebsiella, and a composition comprising the protein, for use in therapy. Also provided is a protein, or composition comprising the protein, for use in a method of treating infection of a subject with Klebsiella. Further provided is an oral enteric formulation for delivering the protein or composition to the small or large intestine. Further provided is an pulmonary formulation for delivering the protein or composition to the lungs. Also provided is a method of preventing or reducing infection or contamination of an object with Klebsiella, a method of treating infection with Klebsiella of a subject or patient in need thereof, and a process of producing a composition comprising the protein. The invention also provides a process of producing a composition the protein of the invention. The invention further provides a nucleic acid molecule encoding a protein having cytotoxic activity against Klebsiella; a plant, plant tissue or plant cell comprising the protein; and a plant, plant tissue or plant comprising the nucleic acid molecule.

BACKGROUND OF THE INVENTION

Klebsiellae are nonmotile, rod-shaped, gram-negative bacteria, encased by the polysaccharide capsule providing resistance against many host defense mechanisms. Klebsiellae are opportunistic pathogens found in the environment and in mammalian mucosal surfaces. Three species in the genus Klebsiella are commonly associated with illness in humans: K. pneumoniae, K. oxytoca, and K. granulomatis. Recently it was discovered that two more Klebsiella species, K. variicola and K. quasipneumoniae also can cause deadly infections (Long et al. 2017).

The principal pathogenic reservoirs of infection are the gastrointestinal tract of patients and the hands of hospital personnel. Outside hospitals, infection with Klebsiella typically occurs in the lungs. The illness typically affects middle-aged and older men with debilitating diseases such as alcoholism, diabetes, or chronic bronchopulmonary disease (Chan et al., 2009). This patient population is believed to have impaired respiratory host defenses. The organisms gain access after the host aspirates colonizing oropharyngeal microbes into the lower respiratory tract (Hirsche et al., 2005).

In recent years, Klebsiellae have become important pathogens in nosocomial infections. Common sites of nosocomial infections include the urinary tract, lower respiratory tract, biliary tract, and surgical wound sites. The spectrum of clinical syndromes includes pneumonia, bacteremia, thrombophlebitis, urinary tract infection (UTI), cholecystitis, diarrhea, upper respiratory tract infection, wound infection, osteomyelitis, and meningitis (Miftode et al., 2008). The presence of invasive devices, contamination of respiratory support equipment, use of urinary catheters, and use of antibiotics are factors that increase the likelihood of nosocomial infection with Klebsiella species (Weisenberg et al., 2009).

K. pneumoniae is one of the six pathogens causing hospital ESKAPE (Enterococcus faecium, Staphylococcus aureus, Klebsiella pneumoniae, Acinetobacter baumannii, Pseudomonas aeruginosa, Enterobacter) infections, which readily develop resistance to antibiotics. In 2016, an outbreak of nosocomial pneumonia was reported in China, where five surgical patients died from infection with hypervirulent carbapenem resistant K. pneumoniae (CRPK) ST11 strain (Gu et al, 2017). Such strain can be named as "superbug" as it is hypervirulent and hyper-resistant to antibiotics. ST11 CR-HvKP strains are infecting relatively healthy people with normal immunity. These are mucoid strains, sticking to all surfaces in Intensive Care Units. Colistin, which is a last resort antibiotic against carbapenem resistant enterobacteriae, has little effect against such strains. For the time being, ceftazidime/avibactam can be used to treat such infections, but the resistance to these antibiotics can be acquired also very soon.

Ever increasing pathogen drug resistance is a global problem and the development of a new generation of antimicrobial substances is urgently needed. Bacteria, competing with each other for ecological niches, produce toxic proteins, called bacteriocins. Bacteriocins usually kill only closely related bacteria, belonging to the same species or genera. Their mechanisms of action are diverse, including pore-formation, DNase and RNase activities, inhibition of protein synthesis or DNA replication, etc. The bacteriocins produced by Gram-positive bacteria are usually called bacteriocins of a determined class depending on their properties, while bacteriocins produced by Gram-negative strains are divided into the colicin-type bacteriocins (high molecular mass, 25-80,000 Da) or microcins (low molecular mass, <10,000 Da) (Lagos et al, 2009).

Antimicrobial peptides are not only produced by bacteria, but also all kinds of organisms when confronted with bacterial infection. Antimicrobial peptides are used in medicine as peptide antibiotics: colistin (polymyxin from Paenibacillus polymyxa), vancomycin (from Amycolatopsis orientalis). However, such antibiotics are mostly used for topical applications or as last resort drugs. Another problem with peptides is inefficient and costly purification from natural sources. It can be overcome by chemical synthesis, however, it is also expensive. Production of recombinant peptides in heterologous hosts is also difficult because of toxicity to host cells (Li, 2011).

There are no registered colicin-like antibiotics to date. However, there are studies in scientific literature where colicin-like bacteriocins are used as potential antimicrobials against Gram-negative pathogens. Most studied are colicins, several research groups are working with pyocins (Grinter et al., 2013; Ghequire, de Mot, 2014). For the time being, bacteriocins from Klebsiella have received very little attention and only few studies are published (James et al, 1987; Riley et al, 2001; Chavan et al, 2005) that belong to the nuclease class. Detailed studies of expression, purification and activity tests of klebicins are lacking.

Departing from the prior art, it is an object of the invention to provide an agent that is active against Kleb-

*siella*. Is also an object of the invention to provide an agent or composition that can be used to treat *Klebsiella* infections of a subject, notably infections by antibiotic-resistant *Klebsiella*. It is a further object to provide a method of preventing or reducing contamination of an object such as food with one or more *Klebsiella* species.

SUMMARY OF THE INVENTION

The inventors have found novel bacteriocins that are active against *Klebsiella*. Thus, the invention provides the following.

1) A protein having cytotoxic activity against *Klebsiella*, said protein preferably having a lipid II-cleaving activity or a pore-forming capability in a cell membrane of *Klebsiella* cells.

2) The protein according to item 1, comprising or consisting of a first amino acid sequence segment and a second amino acid sequence segment, wherein the first amino acid sequence segment is capable of binding to components of *Klebsiella* cells and the second amino acid sequence segment has a lipid II-cleaving activity or a pore-forming capability in a cell membrane of *Klebsiella* cells.

3) A protein having cytotoxic activity against *Klebsiella*, said protein comprising or consisting of a first amino acid sequence segment and a second amino acid sequence segment, wherein the first segment is preferably the N-terminal segment of said protein and the second segment is the C-terminal segment of said protein.

4) The protein according to any one of items 2 or 3, (A) wherein the first segment comprises or consists of the amino acid sequence of (A-i) from amino acid residue 1 to 128 of SEQ ID NO: 1 (KpneM), (A-ii) from amino acid residue 1 to 127 of SEQ ID NO: 2 (KvarM), (A-iii) from amino acid residue 1 to 123 of SEQ ID NO: 3 (KpneM2), (A-iv) from amino acid residue 1 to 118 of SEQ ID NO: 4 (KaerM), (A-v) from amino acid residue 1 to 170 of SEQ ID NO: 5 (KpneA), (A-vi) from amino acid residue 1 to 172 of SEQ ID NO: 6 (KaerA), (A-vii) from amino acid residue 1 to 255 of SEQ ID NO: 7 (Koxy), (A-viii) from amino acid residue 1 to 288 of SEQ ID NO: 8 (Kpnela), or (A-ix) from amino acid residue 1 to 236 of SEQ ID NO: 9 (Kvarla);

or (B) wherein the first segment comprises an amino acid sequence (B-i) having at least 70% sequence identity to the amino acid sequence from amino acid residue 1 to 128 of SEQ ID NO: 1, (B-ii) having at least 70% sequence identity to the amino acid sequence from amino acid residue 1 to 127 of SEQ ID NO: 2, (B-iii) having at least 70% sequence identity to the amino acid sequence from amino acid residue 1 to 123 of SEQ ID NO: 3, (B-iv) having at least 70% sequence identity to the amino acid sequence from amino acid residue 1 to 118 of SEQ ID NO: 4, (B-v) having at least 70% sequence identity to the amino acid sequence from amino acid residue 1 to 170 of SEQ ID NO: 5, (B-vi) having at least 70% sequence identity to the amino acid sequence from amino acid residue 1 to 172 of SEQ ID NO: 6, (B-vii) having at least 70% sequence identity to the amino acid sequence from amino acid residue 1 to 255 of SEQ ID NO: 7, (B-viii) having at least 70% sequence identity to the amino acid sequence from amino acid residue 1 to 288 of SEQ ID NO: 8, or (B-ix) having at least 70% sequence identity to the amino acid sequence from amino acid residue 1 to 236 of SEQ ID NO: 9;

or (C) wherein the first segment comprises an amino acid sequence (C-i) having from 1 to 40 amino acid substitutions, additions, insertions and/or deletions compared to the amino acid sequence of from amino acid residue 1 to 128 SEQ ID NO: 1, (C-ii) having from 1 to 40 amino acid substitutions, additions, insertions and/or deletions compared to the amino acid sequence of from amino acid residue 1 to 127 SEQ ID NO: 2, (C-iii) having from 1 to 40 amino acid substitutions, additions, insertions and/or deletions compared to the amino acid sequence of from amino acid residue 1 to 123 of SEQ ID NO: 3, (C-iv) having from 1 to 40 amino acid substitutions, additions, insertions and/or deletions compared to the amino acid sequence of from amino acid residue 1 to 118 of SEQ ID NO: 4, (C-v) having from 1 to 40 amino acid substitutions, additions, insertions and/or deletions compared to the amino acid sequence of from amino acid residue 1 to 170 SEQ ID NO: 5, (C-vi) having from 1 to 40 amino acid substitutions, additions, insertions and/or deletions compared to the amino acid sequence of from amino acid residue 1 to 172 of SEQ ID NO: 6, (C-vii) having from 1 to 40 amino acid substitutions, additions, insertions and/or deletions compared to the amino acid sequence of from amino acid residue 1 to 255 SEQ ID NO: 7, (C-viii) having from 1 to 40 amino acid substitutions, additions, insertions and/or deletions compared to the amino acid sequence of from amino acid residue 1 to 288 SEQ ID NO: 8, or (C-ix) having from 1 to 40 amino acid substitutions, additions, insertions and/or deletions compared to the amino acid sequence of from amino acid residue 1 to 236 SEQ ID NO: 9.

5) The protein according to any one of items 2 or 3, (A) wherein the amino acid sequence of the first segment is the amino acid sequence of (A-i) from amino acid residue 1 to 128 of SEQ ID NO: 1 (KpneM), (A-ii) from amino acid residue 1 to 127 of SEQ ID NO: 2 (KvarM), (A-iii) from amino acid residue 1 to 123 of SEQ ID NO: 3 (KpneM2), (A-iv) from amino acid residue 1 to 118 of SEQ ID NO: 4 (KaerM), (A-v) from amino acid residue 1 to 170 of SEQ ID NO: 5 (KpneA), (A-vi) from amino acid residue 1 to 172 of SEQ ID NO: 6 (KaerA), (A-vii) from amino acid residue 1 to 255 of SEQ ID NO: 7 (Koxy), (A-viii) from amino acid residue 1 to 288 of SEQ ID NO: 8 (Kpnela), or (A-ix) from amino acid residue 1 to 236 of SEQ ID NO: 9 (Kvarla);

or (B) wherein the amino acid sequence of the first segment has (B-i) at least 70% sequence identity to the amino acid sequence from amino acid residue 1 to 128 of SEQ ID NO: 1, (B-ii) at least 70% sequence identity to the amino acid sequence from amino acid residue 1 to 127 of SEQ ID NO: 2, (B-iii) at least 70% sequence identity to the amino acid sequence from amino acid residue 1 to 123 of SEQ ID NO: 3, (B-iv) at least 70% sequence identity to the amino acid sequence from amino acid residue 1 to 118 of SEQ ID NO: 4, (B-v) at least 70% sequence identity to the amino acid sequence from amino acid residue 1 to 170 of SEQ ID NO: 5, (B-vi) at least 70% sequence identity to the amino acid sequence from amino acid residue 1 to 172 of SEQ ID NO: 6, (B-vii) at least 70% sequence identity to the amino acid sequence from amino acid residue 1 to 255 of SEQ ID NO: 7, (B-viii) at least 70% sequence identity to the amino acid sequence from amino acid residue 1 to 288 of SEQ ID NO: 8, or (B-ix) at least 70% sequence identity to the amino acid sequence from amino acid residue 1 to 236 of SEQ ID NO: 9;

or (C) wherein the amino acid sequence of the first segment has (C-i) from 1 to 40 amino acid substitutions, additions, insertions and/or deletions compared to the amino acid sequence of from amino acid residue 1 to 128 of SEQ ID NO: 1, (C-ii) from 1 to 40 amino acid substitutions, additions, insertions and/or deletions compared to the amino acid sequence of from amino acid residue 1 to 127 of SEQ ID NO: 2, (C-iii) from 1 to 40 amino acid substitutions, additions, insertions and/or deletions compared to the amino acid sequence of from amino acid residue 1 to 123 of SEQ ID NO: 3, (C-iv) from 1 to 40 amino acid substitutions, additions, insertions and/or deletions compared to the amino acid sequence of from amino acid residue 1 to 118 of SEQ ID NO: 4, (C-v) from 1 to 40 amino acid substitutions, additions, insertions and/or deletions compared to the amino acid sequence of from amino acid residue 1 to 170 of SEQ ID NO: 5, (C-vi) from 1 to 40 amino acid substitutions, additions, insertions and/or deletions compared to the amino acid sequence of from amino acid residue 1 to 172 of SEQ ID NO: 6, (C-vii) from 1 to 40 amino acid substitutions, additions, insertions and/or deletions compared to the amino acid sequence of from amino acid residue 1 to 255 of SEQ ID NO: 7, (C-viii) from 1 to 40 amino acid substitutions, additions, insertions and/or deletions compared to the amino acid sequence of from amino acid residue 1 to 288 of SEQ ID NO: 8, or (C-ix) from 1 to 40 amino acid substitutions, additions, insertions and/or deletions compared to the amino acid sequence of from amino acid residue 1 to 236 of SEQ ID NO: 9.

6) The protein according to item 4 or 5, wherein in item (B) any one of the sequence identities is at least 75%, preferably at least 80%, more preferably at least 85%, even more preferably at least 90%, even more preferably at least 95%, and most preferably at least 97%; and/or wherein in item (C) the number of said amino acid substitutions, additions, insertions and/or deletions is from 1 to 30, preferably from 1 to 20, more preferably from 1 to 10, and most preferably at least 1 to 5 compared to any one of said amino acid sequences.

7) The protein according to any one of items 2 to 6, (D) wherein the second segment comprises or consists of the amino acid sequence of (D-i) from amino acid residue 129 to 278 of SEQ ID NO: 1 (KpneM), (D-ii) from amino acid residue 128 to 276 of SEQ ID NO: 2 (KvarM), (D-iii) from amino acid residue 124 to 272 of SEQ ID NO: 3 (KpneM2), (D-iv) from amino acid residue 119 to 266 of SEQ ID NO: 4 (KaerM), (D-v) from amino acid residue 171 to 377 of SEQ ID NO: 5 (KpneA), (D-vi) from amino acid residue 173 to 379 of SEQ ID NO: 6 (KaerA), (D-vii) from amino acid residue 256 to 452 of SEQ ID NO: 7 (Koxy), (D-viii) from amino acid residue 289 to 466 of SEQ ID NO: 8 (Kpnela), or (D-ix) from amino acid residue 237 to 414 of SEQ ID NO: 9 (Kvarla);

or (E) wherein the second segment comprises an amino acid sequence (E-i) having at least 70% sequence identity to the amino acid sequence from amino acid residue 129 to 278 of SEQ ID NO: 1, (E-ii) having at least 70% sequence identity to the amino acid sequence from amino acid residue 128 to 276 of SEQ ID NO: 2, (E-iii) having at least 70% sequence identity to the amino acid sequence from amino acid residue 124 to 272 of SEQ ID NO: 3, (E-iv) having at least 70% sequence identity to the amino acid sequence from amino acid residue 119 to 266 of SEQ ID NO: 4, (E-v) having at least 70% sequence identity to the amino acid sequence from amino acid residue 171 to 377 of SEQ ID NO: 5, (E-vi) having at least 70% sequence identity to the amino acid sequence from amino acid residue 173 to 379 of SEQ ID NO: 6, (E-vii) having at least 70% sequence identity to the amino acid sequence from amino acid residue 256 to 452 of SEQ ID NO: 7, (E-viii) having at least 70% sequence identity to the amino acid sequence from amino acid residue 289 to 466 of SEQ ID NO: 8, or (E-ix) having at least 70% sequence identity to the amino acid sequence from amino acid residue 237 to 414 of SEQ ID NO: 9;

or (F) wherein the second segment comprises an amino acid sequence (F-i) having from 1 to 30 amino acid substitutions, additions, insertions and/or deletions compared to the amino acid sequence of from amino acid residue 129 to 278 of SEQ ID NO: 1, (F-ii) having from 1 to 30 amino acid substitutions, additions, insertions or deletions compared to the amino acid sequence of from amino acid residue 128 to 276 of SEQ ID NO: 2, (F-iii) having from 1 to 30 amino acid substitutions, additions, insertions and/or deletions compared to the amino acid sequence of from amino acid residue 124 to 272 of SEQ ID NO: 3, (F-iv) having from 1 to 30 amino acid substitutions, additions, insertions and/or deletions compared to the amino acid sequence of from amino acid residue 119 to 266 of SEQ ID NO: 4, (F-v) having from 1 to 35 amino acid substitutions, additions, insertions and/or deletions compared to the amino acid sequence of from amino acid residue 171 to 377 of SEQ ID NO: 5, (F-vi) having from 1 to 35 amino acid substitutions, additions, insertions and/or deletions compared to the amino acid sequence of from amino acid residue 173 to 379 of SEQ ID NO: 6, (F-vii) having from 1 to 35 amino acid substitutions, additions, insertions and/or deletions compared to the amino acid sequence of from amino acid residue 256 to 452 of SEQ ID NO: 7, (F-viii) having from 1 to 35 amino acid substitutions, additions, insertions and/or deletions compared to the amino acid sequence of from amino acid residue 289 to 466 of SEQ ID NO: 8, (F-ix) having from 1 to 35 amino acid substitutions, additions, insertions and/or deletions compared to the amino acid sequence of from amino acid residue 237 to 414 of SEQ ID NO: 9.

8) The protein according to any one of items 2 to 7, (D) wherein the amino acid sequence of the second segment comprises or consists of the amino acid sequence of (D-i) from amino acid residue 129 to 278 of SEQ ID NO: 1 (KpneM), (D-ii) from amino acid residue 128 to 276 of SEQ ID NO: 2 (KvarM), (D-iii) from amino acid residue 124 to 272 of SEQ ID NO: 3 (KpneM2), (D-iv) from amino acid residue 119 to 266 of SEQ ID NO: 4 (KaerM), (D-v) from amino acid residue 171 to 377 of SEQ ID NO: 5 (KpneA), (D-vi) from amino acid residue 173 to 379 of SEQ ID NO: 6 (KaerA), (D-vii) from amino acid residue 256 to 452 of SEQ ID NO: 7 (Koxy), (D-viii) from amino acid residue 289 to 466 of SEQ ID NO: 8 (Kpnela), or (D-ix) from amino acid residue 237 to 414 of SEQ ID NO: 9 (Kvarla)

or (E) the amino acid sequence of the second segment has (E-i) at least 80% sequence identity to the amino acid sequence from amino acid residue 129 to 278 of SEQ ID NO: 1, (E-ii) at least 80% sequence identity to the amino acid sequence from amino acid residue 128 to 276 of SEQ ID NO: 2, (E-iii) at least 80% sequence identity to the amino acid sequence from amino acid residue 124 to 272 of SEQ ID NO: 3, (E-iv) at least 80% sequence identity to the amino acid sequence from amino acid residue 119 to 266 of SEQ ID NO: 4, (E-v) at least 80% sequence identity to the amino acid sequence from amino acid residue 171 to 377 of SEQ ID NO: 5, (E-vi) at least 80% sequence identity to the amino acid sequence from amino acid residue 173 to 379 of SEQ ID NO: 6, (E-vii) at least 80% sequence identity to the amino acid sequence from amino acid residue 256 to 452 of SEQ ID NO: 7, (E-viii) at least 80% sequence identity to the amino acid sequence from amino acid residue 289 to 466 of SEQ ID NO: 8, or (E-ix) at least 80% sequence identity to the amino acid sequence from amino acid residue 237 to 414 of SEQ ID NO: 9, or (F) wherein the amino acid sequence of the second segment has (F-i) from 1 to 30 amino acid substitutions, additions, insertions and/or deletions compared to the amino acid sequence of from amino acid residue 129 to 278 SEQ ID NO: 1, (F-ii) from 1 to 30 amino acid substitutions, additions, insertions and/or deletions compared to the amino acid sequence of from amino acid residue 128 to 276 SEQ ID NO: 2, (F-iii) from 1 to 30 amino acid substitutions, additions, insertions and/or deletions compared to the amino acid sequence of from amino acid residue 124 to 272 of SEQ ID NO: 3, (F-iv) from 1 to 30 amino acid substitutions, additions, insertions and/or deletions compared to the amino acid sequence of from amino acid residue 119 to 266 of SEQ ID NO: 4, (F-v) from 1 to 35 amino acid substitutions, additions, insertions and/or deletions compared to the amino acid sequence of from amino acid residue 171 to 377 SEQ ID NO: 5, (F-vi) from 1 to 35 amino acid substitutions, additions, insertions and/or deletions compared to the amino acid sequence of from amino acid residue 173 to 379 of SEQ ID NO: 6, (E-vii) from 1 to 35 amino acid substitutions, additions, insertions and/or deletions compared to the amino acid sequence of from amino acid residue 256 to 452 SEQ ID NO: 7, (F-viii) from 1 to 35 amino acid substitutions, additions, insertions and/or deletions compared to the amino acid sequence of from amino acid residue 289 to 466 SEQ ID NO: 8, or (F-ix) from 1 to 35 amino acid substitutions, additions, insertions and/or deletions compared to the amino acid sequence of from amino acid residue 237 to 414 SEQ ID NO: 9.

9) The protein according to any one of item 7 or 8, wherein said first segment is any one of items A-i to A-iv, B-i to B-iv, or C-i to C-iv and said second segment is any one of items D-i to D-iv, E-i to E-iv, or F-i to F-iv.

10) The protein according to item 9, wherein said first segment is any one or more of items A-i to A-iv and said second segment is any one of items D-i to D-iv, respectively; or said first segment is any one of items B-i to B-iv and said second segment is any one of items E-i to E-iv, respectively; or said first segment is any one of C-i to C-iv and said second segment is any one of items F-i to F-iv, respectively.

11) The protein according to any one of item 7 or 8, wherein said first segment is any one of items A-v to A-ix, B-v to B-ix, or C-v to C-ix and said second segment is any one of items D-v to D-ix, E-v to E-ix, or F-v to F-ix.

12) The protein according to item 11, wherein said first segment is any one of items A-v to A-ix and said second segment is any one of items D-v to D-ix, respectively; or said first segment is any one of items B-v to B-ix and said second segment is any one of items E-v to E-ix, respectively; or said first segment is any one of items C-v to C-ix and said second segment is any one of items F-v to F-ix, respectively.

13) The protein according to item 11 or 12, wherein said first segment is any one of items A-v to A-vi, B-v to B-vi, or C-v to C-vi and said second segment is any one of items D-v to D-vi, E-v to E-vi, or F-v to F-vi, respectively; and/or wherein said first segment is any one of items A-viii to A-ix, B-viii to B-ix, or C-viii to C-ix and said second segment is any one of items D-viii to D-ix, E-viii to E-ix, or F-viii to F-ix, respectively.

14) The protein according to any one of item 4 to 13, wherein the cytotoxic activity of said protein is such that said protein and a comparative protein of the amino acid sequence of the SEQ ID NO: 1 produces spots free of viable bacteria of sensitive *Klebsiella quasipneumoniae* subsp. *similipneumoniae* SB30 (DSM 28212) at least of the same diameter 16 hours after spotting 20 microliters of each of a solution of said protein and of the comparative protein onto a lawn of the sensitive *Klebsiella* strain on an agar plate and subsequent incubation of the agar plate at 37° C., wherein the concentration of said protein in the solution is at most 5 times that of the solution of the respective comparative protein.

15) The protein according to any one of items 1 to 14, comprising or consisting of an amino acid sequence comprising or consisting of (a) the amino acid sequence of
  (a-i) SEQ ID NO: 1 (KpneM),
  (a-ii) SEQ ID NO: 2 (KvarM),
  (a-iii) SEQ ID NO: 3 (KpneM2),
  (a-iv) SEQ ID NO: 4 (KaerM),
  (a-v) SEQ ID NO: 5 (KpneA),
  (a-vi) SEQ ID NO: 6 (KaerA),
  (a-vii) SEQ ID NO: 7 (Koxy),
  (a-viii) SEQ ID NO: 8 (Kpnela), or
  (a-ix) SEQ ID NO: 9 (Kvarla);

or
(b) an amino acid sequence
  (b-i) having at least 70% sequence identity to the amino acid sequence of SEQ ID NO: 1,
  (b-ii) having at least 70% sequence identity to the amino acid sequence of SEQ ID NO: 2,
  (b-iii) having at least 70% sequence identity to the amino acid sequence of SEQ ID NO: 3,
  (b-iv) having at least 70% sequence identity to the amino acid sequence of SEQ ID NO: 4,
  (b-v) having at least 70% sequence identity to the amino acid sequence of SEQ ID NO: 5,
  (b-vi) having at least 70% sequence identity to the amino acid sequence of SEQ ID NO: 6,
  (b-vii) having at least 70% sequence identity to the amino acid sequence of SEQ ID NO: 7,
  (b-viii) having at least 70% sequence identity to the amino acid sequence of SEQ ID NO: 8, or
  (b-ix) having at least 70% sequence identity to the amino acid sequence of SEQ ID NO: 9;
or
(c) an amino acid sequence
  (c-i) having from 1 to 80 amino acid substitutions, additions, insertions and/or deletions compared to the amino acid sequence of SEQ ID NO: 1,
  (c-ii) having from 1 to 80 amino acid substitutions, additions, insertions and/or deletions compared to the amino acid sequence of SEQ ID NO: 2,
  (c-iii) having from 1 to 80 amino acid substitutions, additions, insertions and/or deletions compared to the amino acid sequence of SEQ ID NO: 3,
  (c-iv) having from 1 to 80 amino acid substitutions, additions, insertions and/or deletions compared to the amino acid sequence of SEQ ID NO: 4,
  (c-v) having from 1 to 110 amino acid substitutions, additions, insertions and/or deletions compared to the amino acid sequence of SEQ ID NO: 5,
  (c-vi) having from 1 to 110 amino acid substitutions, additions, insertions and/or deletions compared to the amino acid sequence of SEQ ID NO: 6,
  (c-vii) having from 1 to 130 amino acid substitutions, additions, insertions and/or deletions compared to the amino acid sequence of SEQ ID NO: 7,
  (c-viii) having from 1 to 130 amino acid substitutions, additions, insertions and/or deletions compared to the amino acid sequence of SEQ ID NO: 8, or
  (c-ix) having from 1 to 120 amino acid substitutions, additions, insertions and/or deletions compared to the amino acid sequence of SEQ ID NO: 9.

16) The protein according to item 1 or 15, wherein
(a) the amino acid sequence of said protein is that of
  (a-i) SEQ ID NO: 1 (KpneM),
  (a-ii) SEQ ID NO: 2 (KvarM),
  (a-iii) SEQ ID NO: 3 (KpneM2),
  (a-iv) SEQ ID NO: 4 (KaerM),
  (a-v) SEQ ID NO: 5 (KpneA),
  (a-vi) SEQ ID NO: 6 (KaerA),
  (a-vii) of SEQ ID NO: 7 (Koxy),
  (a-viii) of SEQ ID NO: 8 (Kpnela), or
  (a-ix) SEQ ID NO: 9 (Kvarla);
or
(b) the amino acid sequence of said protein has
  (b-i) at least 70% sequence identity to the amino acid sequence of SEQ ID NO: 1,
  (b-ii) at least 70% sequence identity to the amino acid sequence of SEQ ID NO: 2, (b-iii) at least 70% sequence identity to the amino acid sequence of SEQ ID NO: 3, (b-iv) at least 70% sequence identity to the amino acid sequence of SEQ ID NO: 4, (b-v) at least 70% sequence identity to the amino acid sequence of SEQ ID NO: 5, (b-vi) at least 70% sequence identity to the amino acid sequence of SEQ ID NO: 6, (b-vii) at least 70% sequence identity to the amino acid sequence of SEQ ID NO: 7, (b-viii) at least 70% sequence identity to the amino acid sequence of SEQ ID NO: 8, or (b-ix) at least 70% sequence identity to the amino acid sequence of SEQ ID NO: 9;

or (c) the amino acid sequence of said protein has (c-i) from 1 to 80 amino acid substitutions, additions, insertions and/or deletions compared to the amino acid sequence of SEQ ID NO: 1, (c-ii) from 1 to 80 amino acid substitutions, additions, insertions and/or deletions compared to the amino acid sequence of SEQ ID NO: 2, (c-iii) from 1 to 80 amino acid substitutions, additions, insertions and/or deletions compared to the amino acid sequence of SEQ ID NO: 3, (c-iv) from 1 to 80 amino acid substitutions, additions, insertions and/or deletions compared to the amino acid sequence of SEQ ID NO: 4, (c-v) from 1 to 110 amino acid substitutions, additions, insertions and/or deletions compared to the amino acid sequence of SEQ ID NO: 5, (c-vi) from 1 to 110 amino acid substitutions, additions, insertions and/or deletions compared to the amino acid sequence of SEQ ID NO: 6, (c-vii) from 1 to 130 amino acid substitutions, additions, insertions and/or deletions compared to the amino acid sequence of SEQ ID NO: 7, (c-viii) from 1 to 130 amino acid substitutions, additions, insertions and/or deletions compared to the amino acid sequence of SEQ ID NO: 8, or (c-ix) from 1 to 120 amino acid substitutions, additions, insertions and/or deletions compared to the amino acid sequence of SEQ ID NO: 9.

17) The protein according to any one of items 15 or 16, wherein in item (b) any one of the sequence identities is at least 75%, preferably at least 80%, more preferably at least 85%, even more preferably at least 90%, even more preferably at least 95%, and most preferably at least 97%; and/or wherein in item (c) the number of said amino acid substitutions, additions, insertions and/or deletions is from 1 to 30, preferably from 1 to 20, more preferably from 1 to 10, and most preferably at least 1 to 5 compared to any one of said amino acid sequences.

18) The protein according to any one of item 15, 16, or 17, wherein the cytotoxic activity of said protein of any one of items (b-i) to (b-ix) or (c-i) to (c-ix) is such that said protein and a comparative protein of the amino acid sequence of the SEQ ID NO of said item (b-i) to (b-ix) or (c-i) to (c-ix), respectively, produce spots free of viable bacteria of sensitive *Klebsiella quasipneumoniae* subsp. *similipneumoniae* SB30 (DSM 28212) at least of the same diameter 16 hours after spotting 20 microliters of each of a solution of said protein and of the comparative protein onto a lawn of the sensitive *Klebsiella* strain on an agar plate and subsequent incubation of the agar plate at 37° C., wherein the concentration of said protein in the solution is at most 5 times that of the solution of the respective comparative protein.

19) The protein according to any one of items 1 to 17, wherein said protein has a cell wall biosynthesis-inhibiting activity, whereby the protein is capable of degrading undecaprenyl phosphate-linked peptidoglycan precursors.

20) The protein according to any one of items 2 to 17, wherein the first segment comprises a translocation and a receptor-binding domain.

21) The protein according to any one of items 1 to 20, having bactericidal or bacteriostatic activity against *Klebsiella pneumoniae, Klebsiella oxytoca, Klebsiella granulomatis, Klebsiella quasipneumoniae, Klebsiella aerogenes,* and/or *Klebsiella variicola.*

22) A protein having cytotoxic activity against *Klebsiella,* optionally a protein according to any one of items 1 to 21, said protein comprising an amino acid sequence selected from the group consisting of SEQ ID NO: 22 to 24, wherein each X stands for any one of the 20 standard amino acid residues or for an absent amino acid residue and J stands for either L (leucine) or I (isoleucine).

23) The protein according to any one of items 1 to 22, wherein said protein is any one defined with respect to SEQ ID NOs: 1-4, 7, 8 or 22 as a reference sequence, preferable any one defined with respect to SEQ ID NOs: 1-4 or 22 as a reference sequence.

24) The protein according to item 1 or 23, wherein the cytotoxic activity of said protein is such that said protein and a comparative protein of the amino acid sequence of SEQ ID NO: 1 produce spots free of viable bacteria of sensitive *Klebsiella quasipneumoniae* subsp. *similipneumoniae* SB30 (DSM 28212) at least of the same diameter 16 hours after spotting 20 microliters of each of a solution of said protein and of the comparative protein onto a lawn of the sensitive *Klebsiella* strain on an agar plate and subsequent incubation of the agar plate at 37° C., wherein the concentration of the protein in the solution is at most 5 times that of the solution of the comparative protein.

25) A composition comprising one or more proteins as defined in any one of items 1 to 24.

26) The composition according to item 25, wherein the cytotoxic activity of said composition is such that said composition and a comparative composition containing the comparative protein of the amino acid sequence of SEQ ID NO: 1 produce spots free of viable bacteria of sensitive *Klebsiella quasipneumoniae* subsp. *similipneumoniae* SB30 (DSM 28212) at least of the same diameter 16 hours after spotting 20 microliters of each of a solution of said composition and a comparative solution of the comparative composition onto a lawn of the sensitive *Klebsiella* strain on an agar plate and subsequent incubation of the agar plate at 37° C., wherein the protein concentration in the solution of said composition is at most 5 times that of the protein concentration in the comparative solution.

27) The composition according to item 25 or 26, further comprising at least one colicin and/or at least one salmocin.

28) The composition according to any one of items 25 to 27, wherein the composition is a pharmaceutical composition.

29) The composition according to any one of items 25 to 28, wherein said composition is a plant material or extract thereof, wherein the plant material is a material from a plant having expressed said one or more proteins, preferably an edible plant having expressed said one or more proteins.

30) The composition according to item 29, wherein said plant material is a material from a plant selected from the group consisting spinach, chard, beetroot, carrot, sugar beet, leafy beet, amaranth, *Nicotiana*, preferably *Nicotiana benthamiana*, and/or said plant material is one or more leaves, roots, tubers, or seeds, or a crushed, milled or comminuted product of said leaves, roots, tubers, or seeds.

31) The composition according to any one of items 25 to 30, wherein said composition is an aqueous solution containing said protein in dispersed form, preferably in dissolved form.

32) The protein or composition according to any one of items 1 to 31 for use in therapy, preferably for use in a method of treating infection of a subject with *Klebsiella*, such as *Klebsiella pneumoniae*, *Klebsiella oxytoca*, *Klebsiella quasipneumoniae*, *Klebsiella aerogenes*, and/or *Klebsiella variicola*.

33) The protein for the use according to item 32, wherein said *Klebsiella* is antibiotic-resistant such as carbapenem-resistant.

34) The protein for the use according to item 32 or 33, wherein said protein is any one defined with respect to SEQ ID NOs: 1-4, 7, 8 or 22 as a reference sequence, preferable any one defined with respect to SEQ ID NOs: 1-4 or 22 as a reference sequence.

35) A method of preventing or reducing infection or contamination of an object with one or more *Klebsiella* species, comprising contacting said object with a protein as defined in any one of items 1 to 24 or a composition as defined in any one of items 25 to 31.

36) A method of treating infection with *Klebsiella* of a subject in need thereof, comprising administering to said subject a protein as defined in any one of items 1 to 24 or a composition as defined in any one of items 25 to 31.

37) The method according to item 35 or 36, wherein said *Klebsiella* includes *Klebsiella pneumoniae*, *Klebsiella oxytoca*, *Klebsiella quasipneumoniae*, *Klebsiella aerogenes*, and/or *Klebsiella variicola*.

38) A process of producing a composition comprising a protein as defined in any one of items 1 to 24, said process comprising the following steps:
   (i) expressing said protein in a plant, preferably an edible plant or *Nicotiana*,
   (ii) harvesting plant material containing expressed protein from said plant,
   (iii) extracting said protein from said plant material using an aqueous buffer to obtain a composition containing said protein,
   (iv) optionally removing undesired contaminants from said composition.

39) The composition according to any one of items 25 to 31, wherein said one or more proteins is/are formulated for oral delivery to the small or large intestine.

40) Oral formulation comprising the protein according to any one of items 1 to 24 or the composition according to any one of items 25 to 31, said formulation being capable of protecting the protein from gastric conditions and capable of releasing the protein in the small or large intestine.

41) A nucleic acid molecule encoding the protein as defined in any one of items 1 to 24.

42) A nucleic acid molecule or nucleic acid construct encoding the protein as defined in any one of items 1 to 24, preferably the protein as defined in any one of items 15 to 23, said nucleic acid molecule or nucleic acid construct comprising a transcription promoter that is preferably active in plant cells and a nucleotide sequence encoding said protein for expressing said nucleotide sequence in cells, preferably in plant cells, under the control of said promoter.

43) A nucleic acid molecule or nucleic acid construct encoding the protein as defined in any one of items 1 to 24, preferably the protein as defined in any one of items 15 to 23, said nucleic acid molecule or nucleic acid construct is or encodes a viral (DNA or RNA) replicon comprising a nucleotide sequence encoding said protein for expressing said nucleotide sequence in cells, preferably in plant cells; said replicon may contain a subgenomic promoter for expressing said nucleotide sequence in plant cells or cells of a plant under the control of said subgenomic promoter.

44) A plant, plant tissue, or plant cell, comprising a protein as defined in any one of items 1 to 24.

45) A plant, plant tissue, or plant cell, comprising a nucleic acid molecule or nucleic acid construct as defined in item 42 or 43.

US 12,655,181 B2

15

FIG. 3 illustrates the purification of klebicins from *Nicotiana benthamiana* leaf biomass. A, C, E, G, I, K—purification schemes of KpneM (A), KpneM2 (C), KvarM (E), KpneA (G), KaerA (I) and Kvarla (K). B, D, F, H, J, L—SDS-PAGE analysis of protein samples taken from different KpneM (B), KpneM2 (D), KvarM (F), KpneA (H), KaerA (J) and Kvarla (L) purification steps. Solutions containing 5 μg of protein were resolved in 12% SDS-PAGE gel for Coomassie staining. B—lane 1 and 7—PageRuler™ Prestained protein ladder, lane 2—crude extract, lane 3—total soluble proteins loaded on Phenyl sepharose, lane 4—flow through Phenyl sepharose, lane 5—KpneM eluate (after Phenyl sepharose), lane 6—impurities eluate (after Phenyl sepharose), lane 8—proteins loaded on Q sepharose, lane 9—KpneM flow through Q sepharose, lane 10—impurities eluate (after Q sepharose); D—lane 1 and 6—PageRuler™ Prestained protein ladder, lane 2—total soluble proteins loaded on Phenyl sepharose, lane 3—flow through Phenyl sepharose, lane 4—KpneM2 eluate (after Phenyl sepharose), lane 5—impurities eluate (after Phenyl sepharose), lane 7—proteins loaded on Q sepharose, lane 8—KpneM2 flow through Q sepharose, lane 9—impurities eluate (after Q sepharose); F—lane 1 and 7—PageRuler™ Prestained protein ladder, lane 2—crude extract, lane 3—total soluble proteins loaded on Phenyl sepharose, lane 4—flow through Phenyl sepharose, lane 5—KvarM eluate (after Phenyl sepharose), lane 6—impurities eluate (after Phenyl sepharose), lane 8—proteins loaded on Q sepharose, lane 9—KvarM flow through Q sepharose, lane 10—impurities eluate (after Q sepharose); H—lane 1 and 7—PageRuler™ Prestained protein ladder, lane 2—crude extract, lane 3—total soluble proteins loaded on Phenyl sepharose, lane 4—flow through Phenyl sepharose, lane 5—KpneA eluate (after Phenyl sepharose), lane 6—impurities eluate (after Phenyl sepharose), lane 8—proteins loaded on SP sepharose, lane 9—flow through SP sepharose, lane 10—KpneA eluate (after SP sepharose); J—lane 1 and 6—PageRuler™ Prestained protein ladder, lane 2—crude extract, lane 3—total soluble proteins loaded on SP sepharose, lane 4—flow through SP sepharose, lane 5—KaerA eluate (after SP sepharose), lane 7—proteins loaded on Q sepharose, lane 8—KaerA flow through Q sepharose. L—lane 1 and 7—PageRuler™ Prestained protein ladder, lane 2—crude extract, lane 3—total soluble proteins loaded on Phenyl sepharose, lane 4—flow through Phenyl sepharose, lane 5—Kvarla eluate (after Phenyl sepharose), lane 6—impurities eluate (after Phenyl sepharose), lane 8—proteins loaded on SP sepharose, lane 9—flow through SP sepharose, lane 10—Kvarla eluate (after SP sepharose). The arrows mark recombinant proteins.

Figure 4:
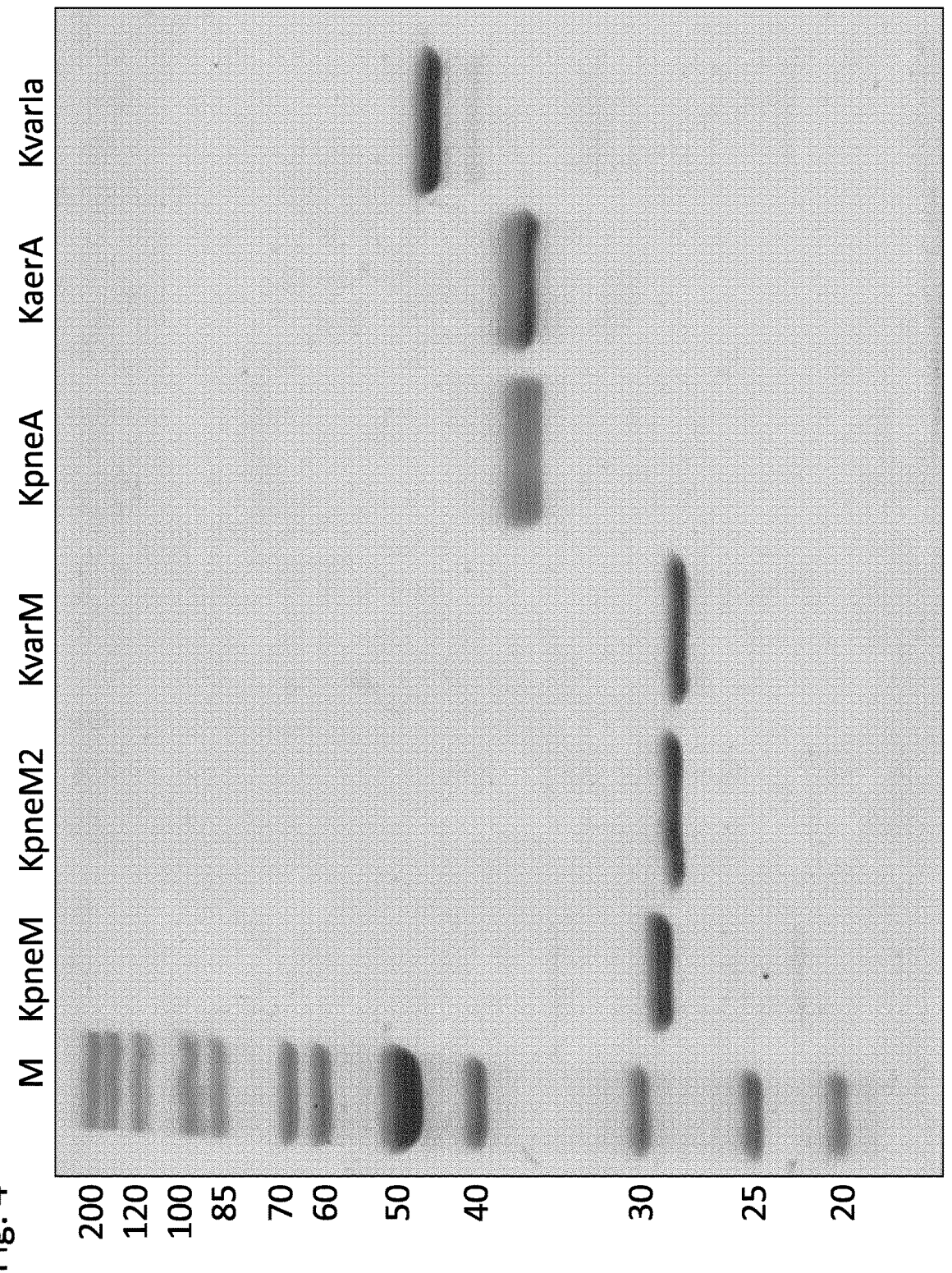

FIG. 4 shows purified klebicins on one gel. 0.5 μg of purified klebicins were resolved in 12% SDS-PAGE gel for Coomassie staining. M—PageRuler Unstained Protein Ladder (ThermoFisher Scientific Baltics).

Figure 5:
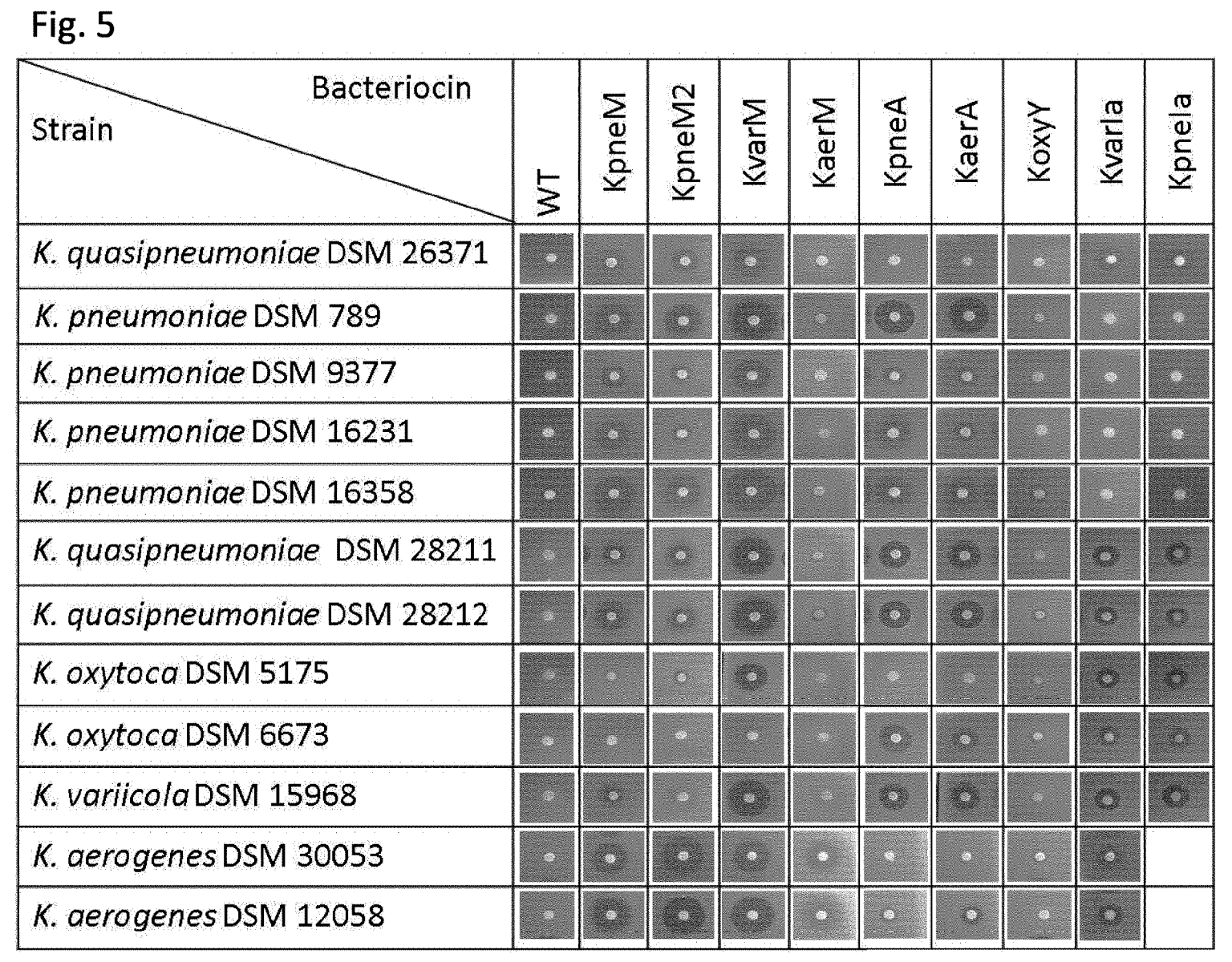

FIG. 5 illustrates an evaluation of klebicins activity against *Klebsiella* strains in soft-agar overlay assay. Overnight cultures of bacterium were grown in CAA medium, equalized till OD595=1.0, diluted 100× with melted top CAA agar and poured on CAA agar plates. 20 μL drops of protein crude extract were spotted on 6 mm Whatman disks and Petri plates were incubated overnight at 30° C. or 37° C.

Figure 6:
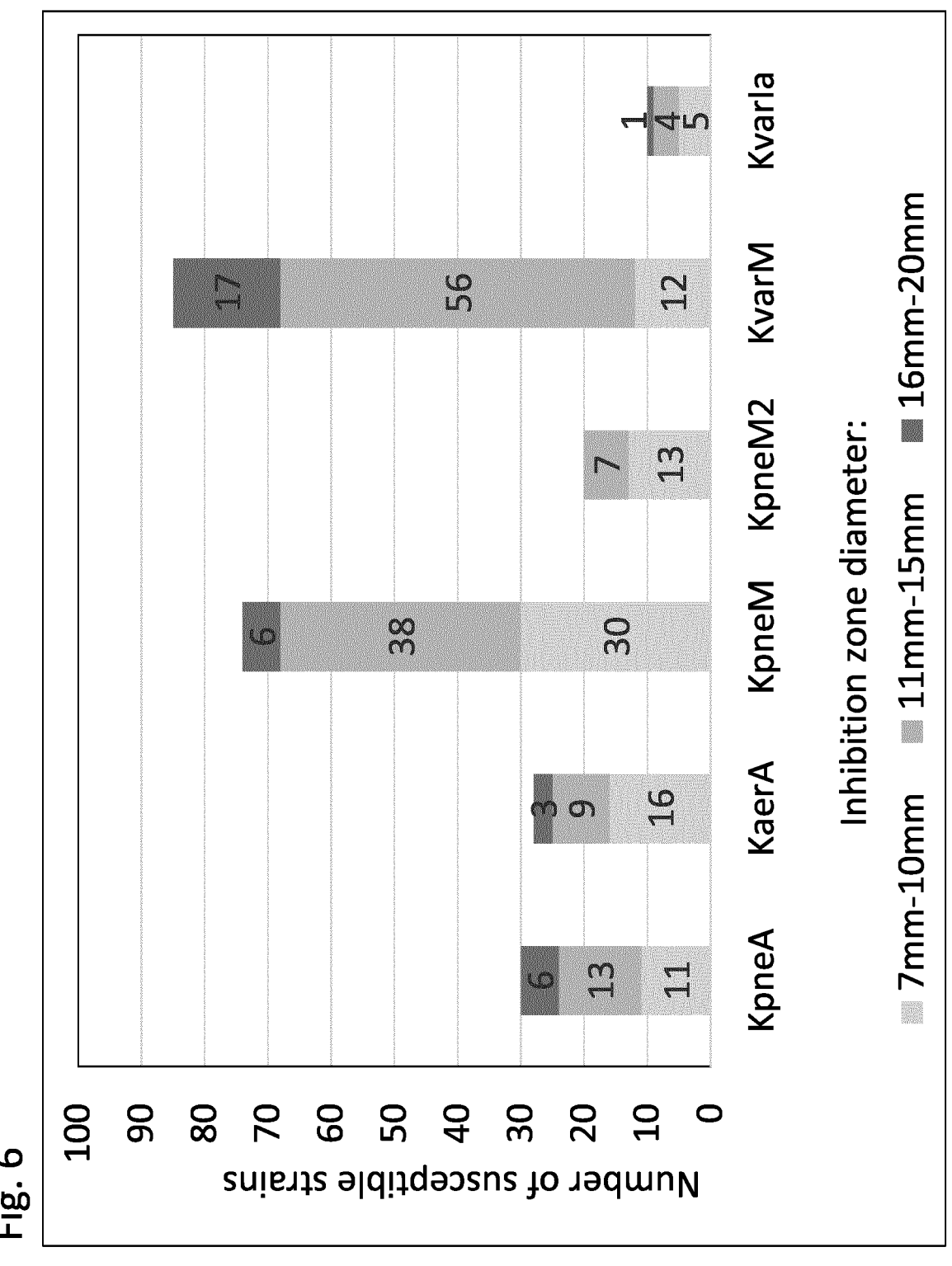

FIG. 6 shows the sensitivity of clinical *Klebsiella* isolates to six plant-expressed klebicins. 100 clinical *Klebsiella* isolates (89 *K. pneumoniae* and 11 *K. oxytoca*) were tested in drop plate assay. The strains susceptible to each klebicin are grouped by the size of the inhibition zone.

16

Figure 7:
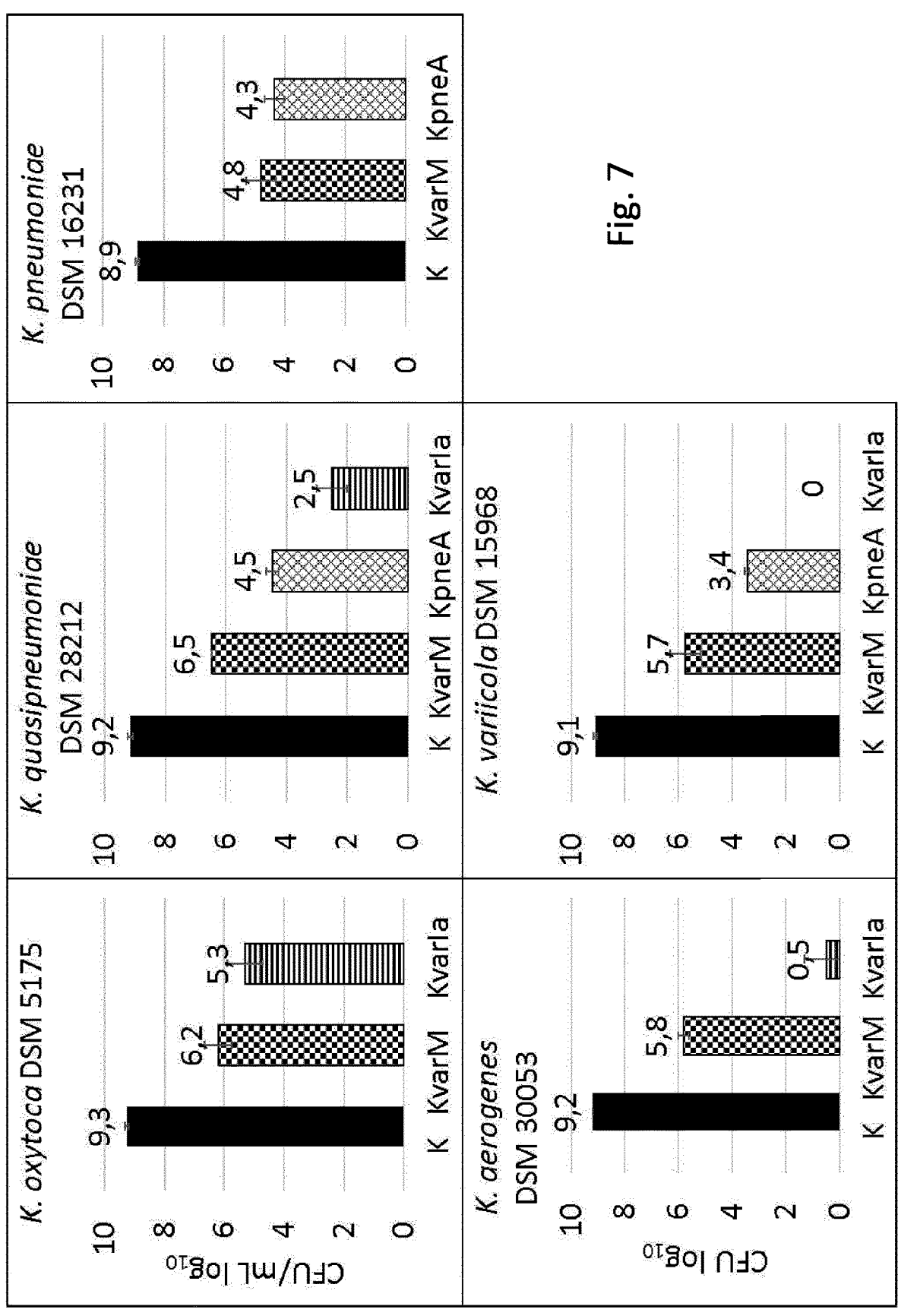

FIG. 7 shows klebicin cytotoxicity assays in the liquid culture. Overnight *Klebsiella* cultures were diluted to OD600=0.3 in CAA medium, treated with 5 μg mL-1 of either of klebicins and bacteria further incubated for 5 h with shaking (200 rpm). The antimicrobial activity of klebicins was evaluated by counting colony forming units in tested culture. Bars represent standard deviation.

Figure 8:
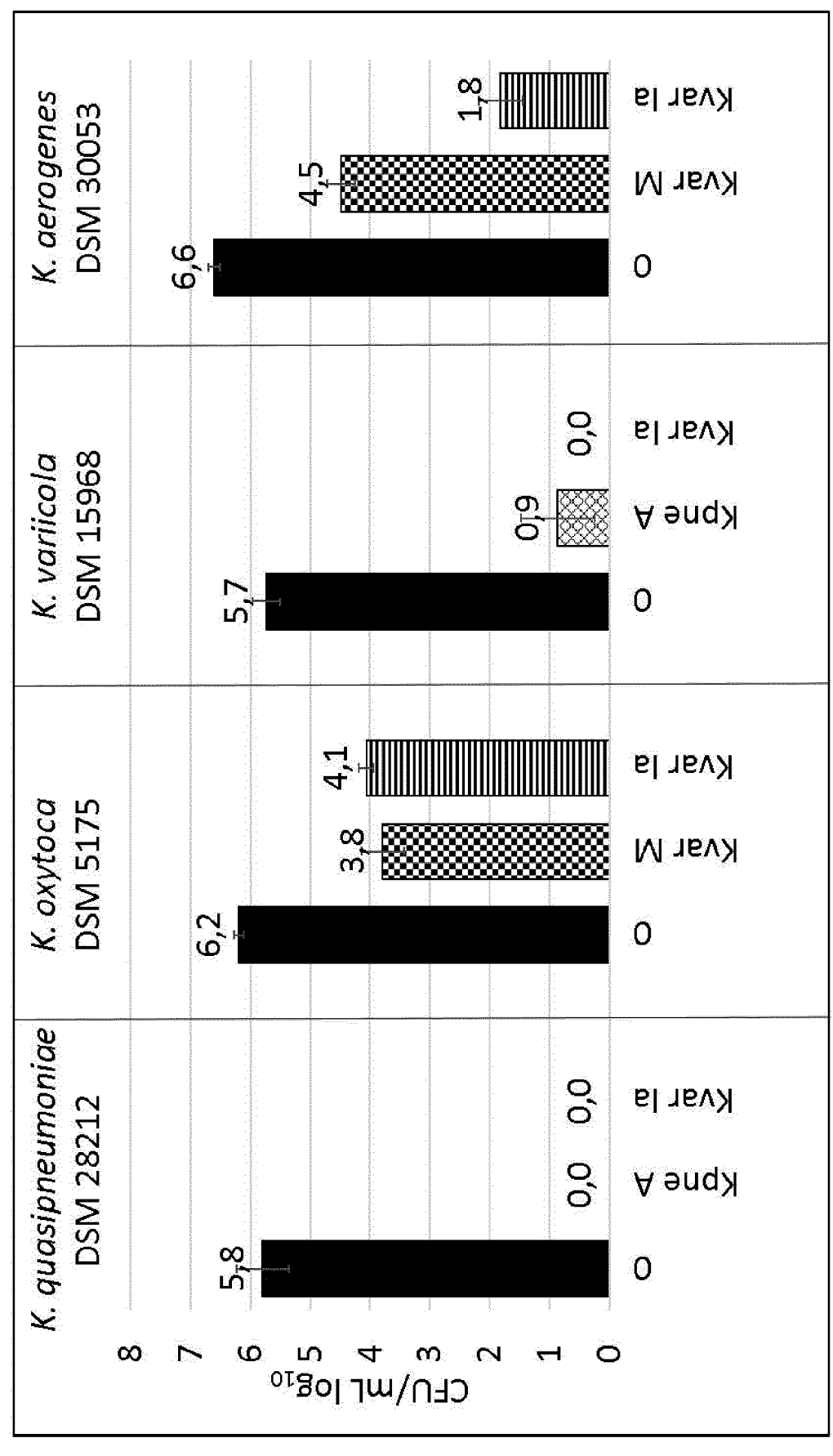

FIG. 8 shows klebicins activity against biofilms. One day-old *K. quasipneumoniae, K. oxytoca, K. variicola, K. aerogenes* biofilms grown in CAA medium were treated with 5 μg mL$^{-1}$ of either of klebicins. The antimicrobial activity of klebicins was evaluated by counting colony forming units in tested culture. Bars represent standard deviation.

Figure 9:
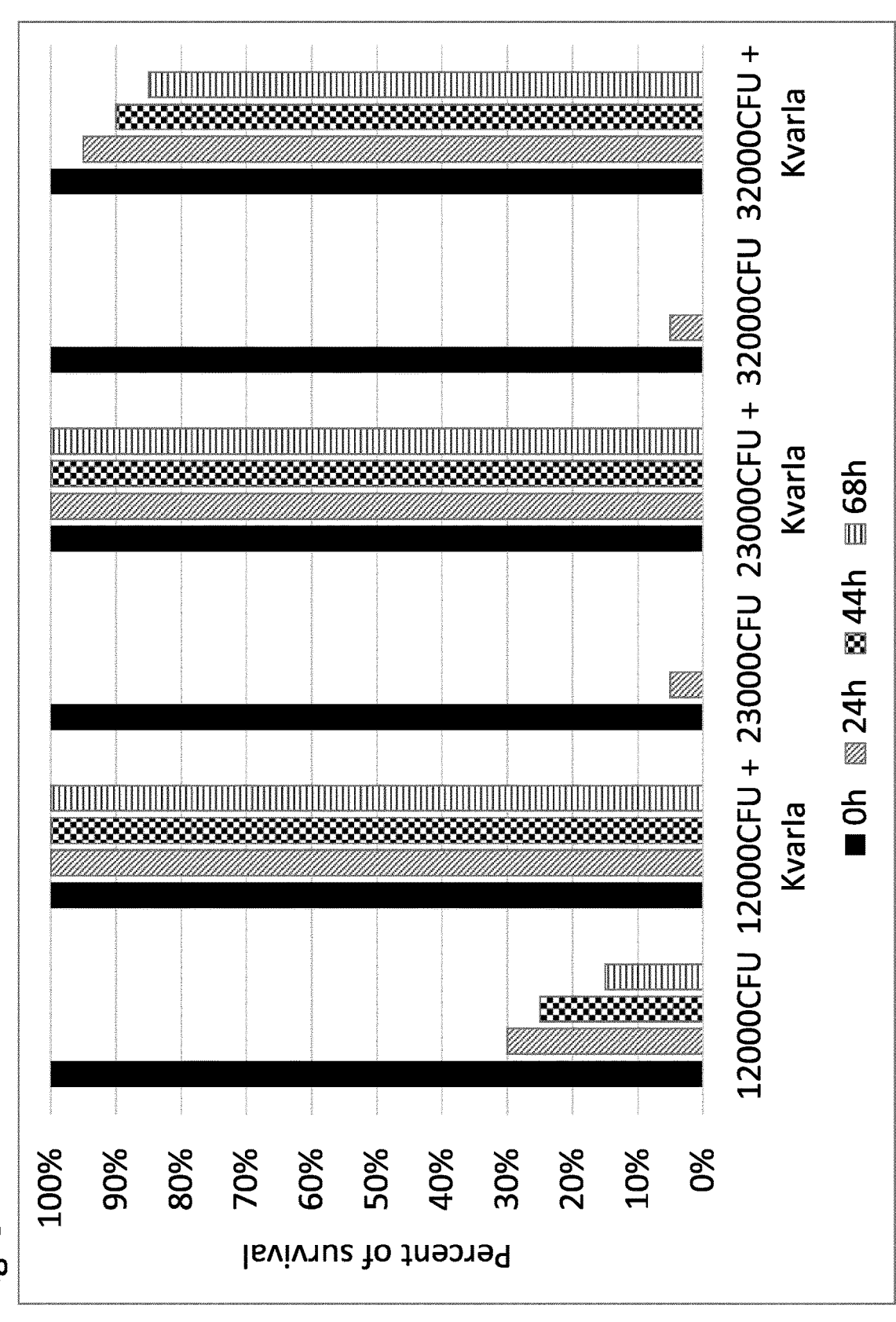

FIG. 9 shows Impact of Kvarla treatment to the survival of *Galleria mellonella* larvae after challenge with *K. quasipneumoniae* DSM 28212. *G. melonella* larvae were infected with 12000-32000 CFU of *K. pneumoniae* DSM 28212 and treated with 10 μg of Kvarla 2 hours after infection. Larvae were incubated in Petri dishes at 37 C.° up to 68 h. 20 larvae were used for each treatment point.

Figure 10A:
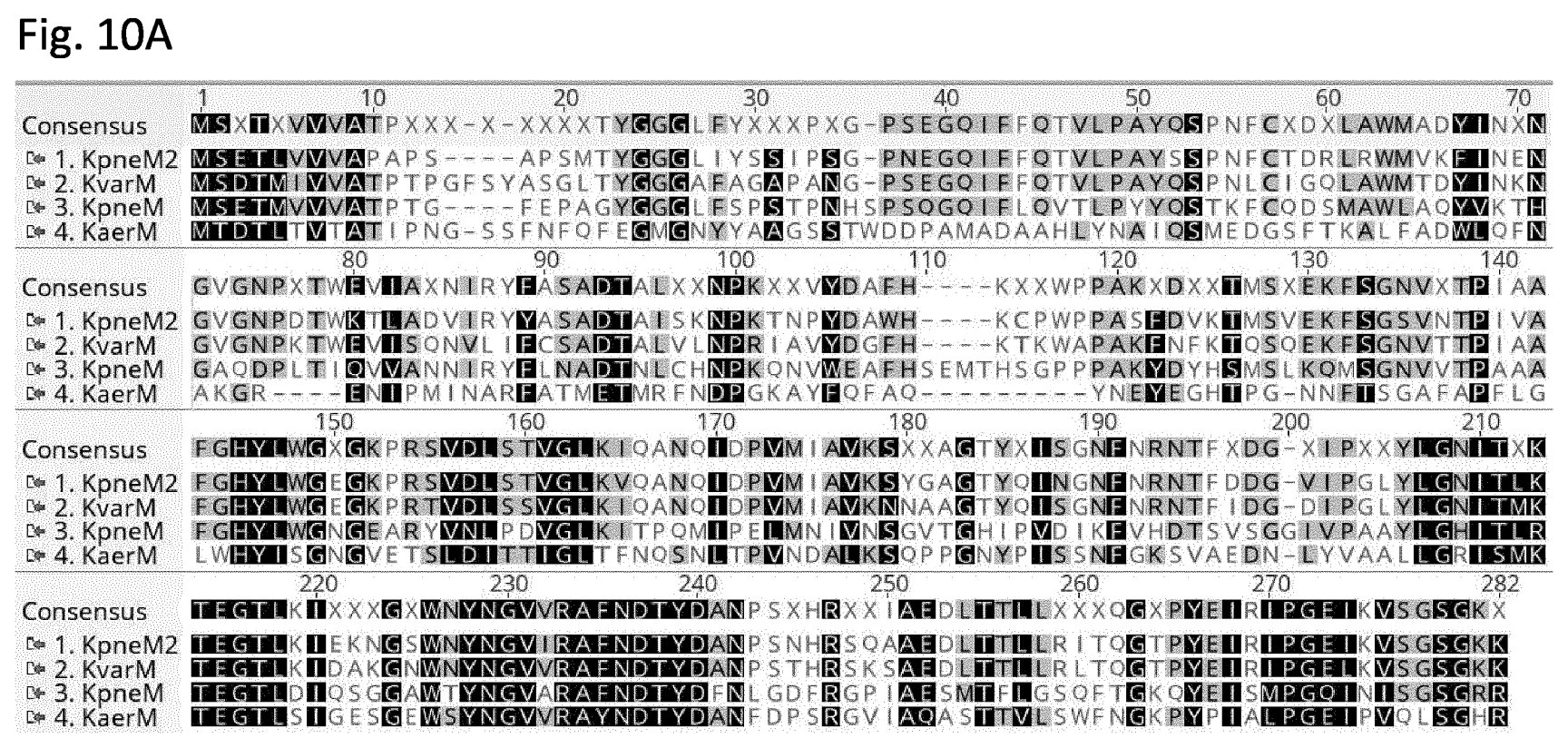
Figure 10B:
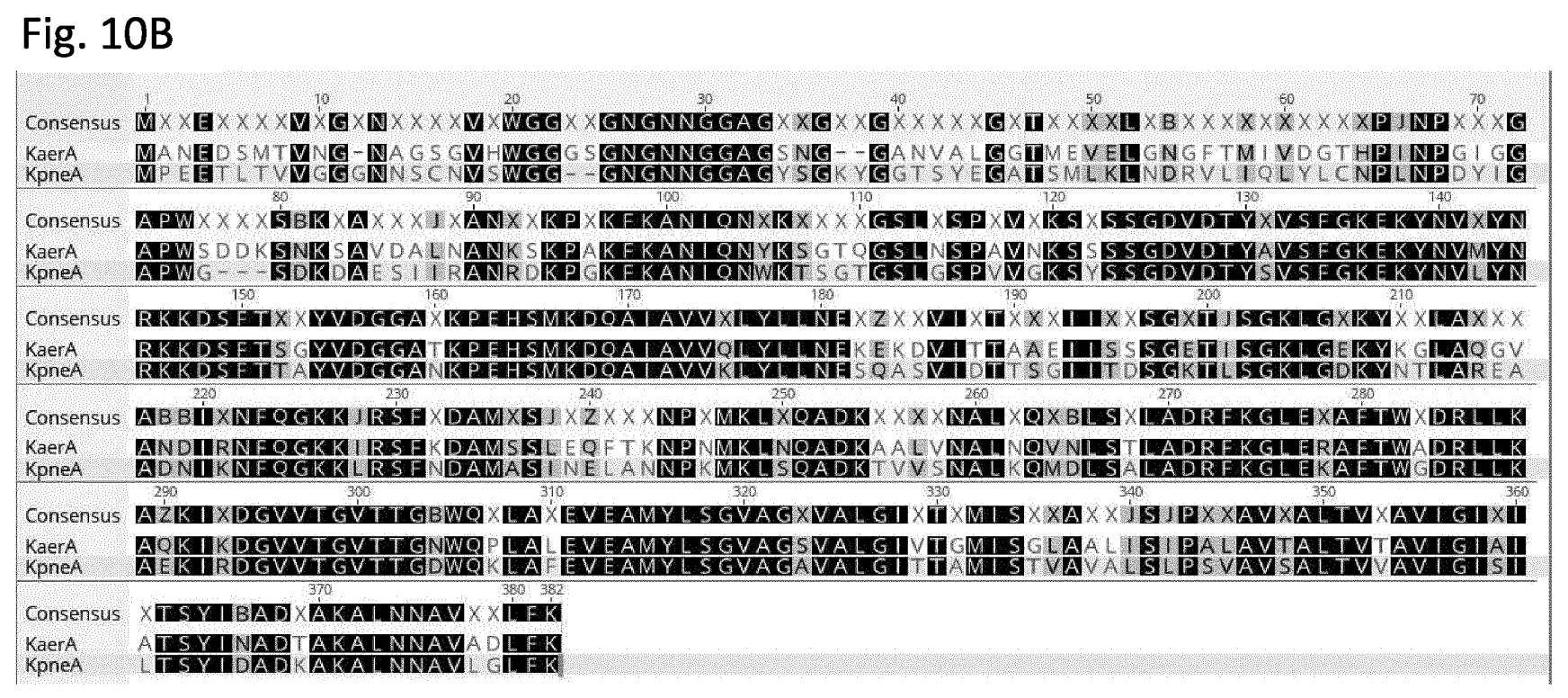

FIG. 10 shows the deduction of the consensus sequence as given in SEQ ID NO: 22-24. The one-letter code refers to the 20 standard amino acids, the "X" stands for insufficient conservation to deduce a consensus amino acid at the respective position and the "–" for omission of an amino acid during deduction of the consensus sequence due to low conservation. J represents either L (leucine) or I (isoleucine). Highly conserved amino acids are highlighted in black, moderately conserved amino acids are highlighted in grey. The software "Geneious Prime Clustal W" in standard settings was used for deduction of the consensus sequences. FIG. 10A shows deduction of SEQ ID NO: 22. FIG. 10B shows deduction of SEQ ID NO: 23. FIG. 10C shows deduction of SEQ ID NO: 24.

FIG. 11 shows the evaluation of the activity of klebicins KpneM, KpneM2, Kvarla, KpneA, KaerA and KvarM and their concentrations upon storage as lyophilized purified proteins. Klebicin activity against susceptible bacterium was evaluated in liquid cultures or by radial diffusion assay. Antimicrobial activity was expressed as CFU/mL Δ log$_{10}$ when activity was evaluated in liquid cultures or as specific activity units (AU) if radial diffusion assay was used for the evaluation. Klebicin concentration was determined by the Bradford assay. Data are the mean±SD of three independent experiments. (A) Activity of klebicins KpneM, KpneM2, Kvarla upon storage at −20° C. (B) Activity of klebicins KpneM, KpneM2, Kvarla upon the storage at 5° C. (C) Activity of klebicins KpneM, KpneM2, Kvarla upon the storage at room temperature. (D) Activity of klebicins KpneA, KaerA and KvarM upon the storage at −20° C. (E) Activity of klebicins KpneA, KaerA and KvarM upon the storage at 5° C. (F) Activity of klebicins KpneA, KaerA and KvarM upon the storage at room temperature. (G) Trendlines of klebicin concentration upon the storage at −20° C. (H) Trendlines of klebicin concentration upon the storage at 5° C. (I) Trendlines of klebicin concentration upon the storage at room temperature.

FIG. 12 shows the residual activity of Kvarla and Eudragit S100-coated Kvarla after in vitro gastric digestion in soft agar overlay assay and assessment of the digestion of the Kvarla by pepsin into fragments by SDS-PAGE. (A) The evaluation of residual activity of Kvarla and Eudragit S100-coated Kvarla in soft agar overlay assay after simulated gastric digestion in vitro. Protein samples were digested by pepsin (pepsin:protein ratio 1:40) for 0.5, 5, 10, 20, 30 and 60 min. Dilutions of all samples by ratio 1:2 were made in distilled water and 5 μL aliquots of diluted samples were dropped on MHA plates with *K. quasipneumoniae* DSM28212 lawn. (B) Tricine SDS page assay of Kvarla digestion. Coomassie staining was used to visualize protein decomposition and estimate the MW of peptide products. The presence and/or absence of pepsin and Kvarla are indicated. Times are indicated in minutes and correspond to those in (A).

Figure 13:
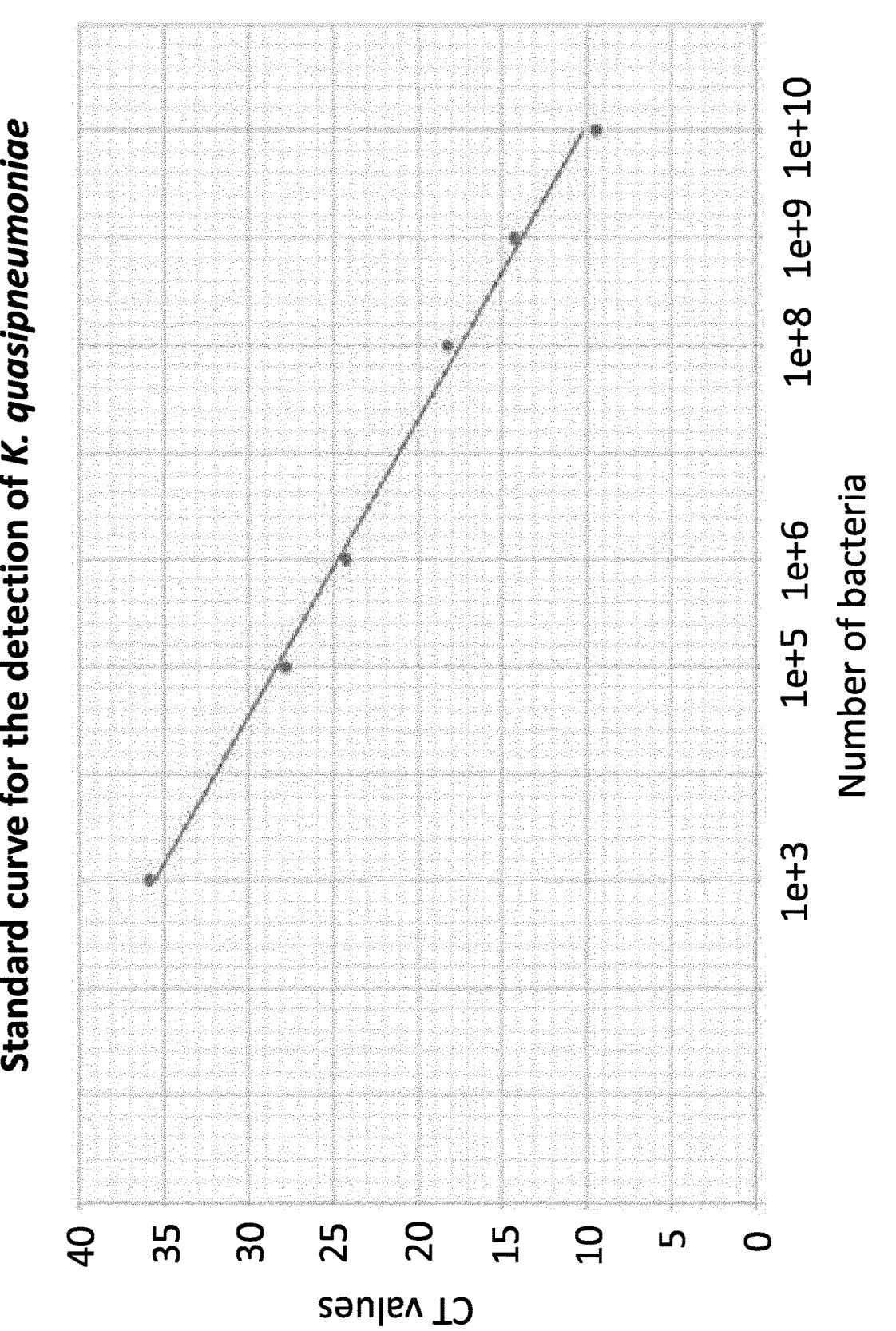

FIG. 13 shows the standard curve for the detection of *K. quasipneumoniae* obtained by real time-PCR, based on khe gene amplification.

Figure 14:
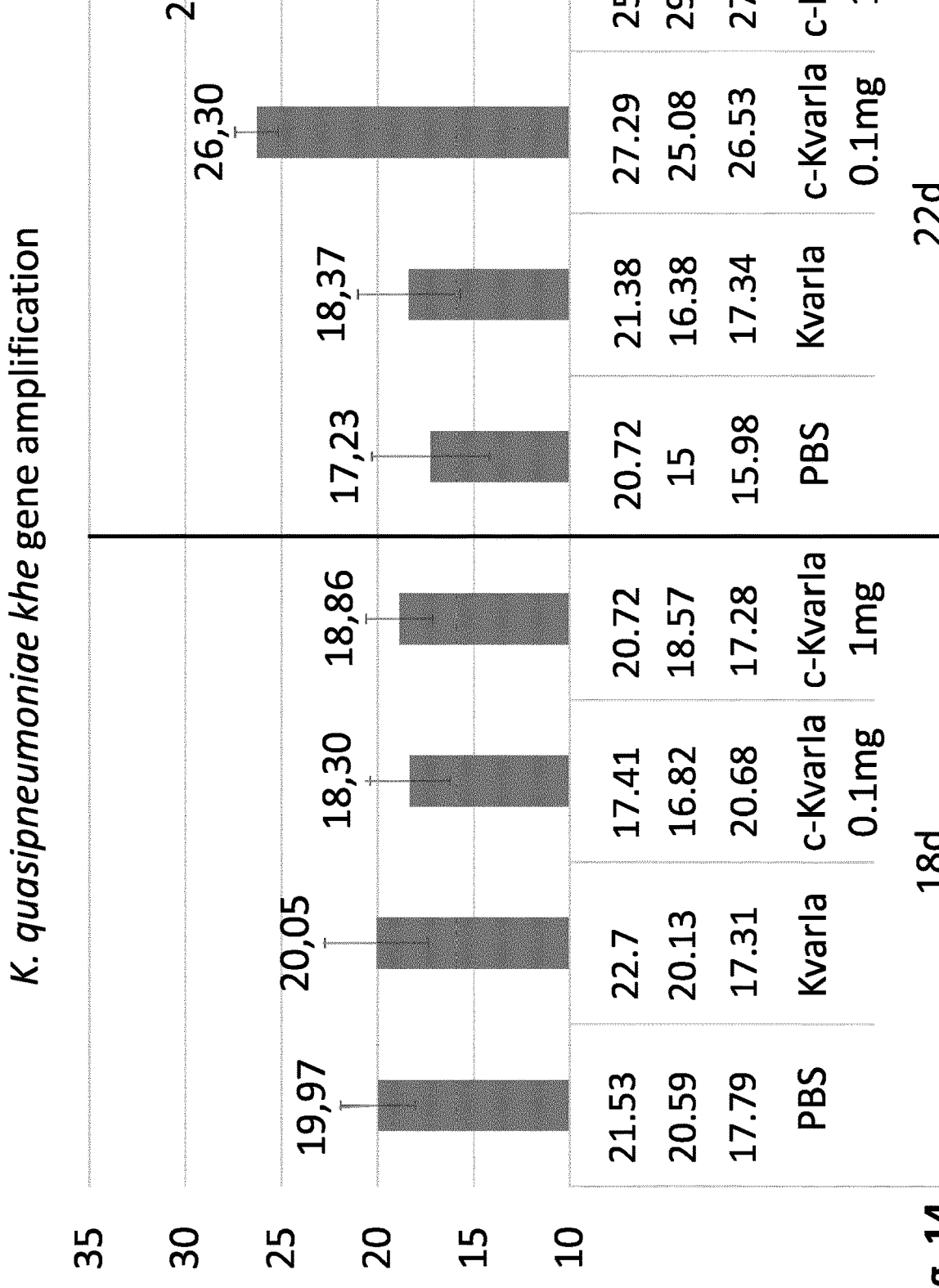

FIG. 14 shows real time-PCR results in *K. quasipneumoniae* colonized mice faecal samples before and after klebicin treatment. Faecal samples of 3 mice were used for each experimental point. 18d: faecal samples collected $18^{th}$ day of experiment, before the start of klebicin treatment; 22d: faecal samples collected $22^{nd}$ day of experiment, next day after last klebicin gavage.

DETAILED DESCRIPTION OF THE INVENTION

The inventors of the present invention have identified proteins having bactericidal or bacteriostatic activity against *Klebsiella*. Such proteins are referred to herein as "klebicins". The protein or klebicin of the invention preferably has a lipid II-cleaving activity or a capability of forming pores in a bacterial cell membrane.

The protein or klebicin of the invention generally comprises at least two amino acid sequence segments (sometimes briefly referred to herein as "segments"). Herein, an amino acid sequence segment refers to a plurality of contiguous amino acid residues in the primary structure of a protein or polypeptide, wherein the protein or polypeptide has a larger number of amino acid residues in its primary structure than the segment. The protein of the invention generally comprises or consists of a first segment and a second segment. The first segment generally provides the protein with the capability of binding to components of *Klebsiella* cells (such as binding to a receptor) and/or it provides the protein with the capability of being introduced into or being taken up by *Klebsiella* cells (cell translocation). The second segment may have lipid II-cleaving activity or a pore-forming capability in a bacterial cell membrane. The second segment therefore provides the protein with its cytotoxic activity. In one embodiment, the first segment is on the N-terminal side in the primary structure of said protein and the second segment is on the C-terminal side or vice versa, wherein the former is preferred. Accordingly, the inventive protein may comprise or consist of an N-terminal first segment and a C-terminal second segment. In another embodiment, the second segment is on the N-terminal side in the primary structure of said protein and the first segment is on the C-terminal side. Accordingly, the inventive protein may comprise or consist of an N-terminal second segment and a C-terminal first segment.

First Segment of the Protein of the Invention

The protein of the invention may comprise a first segment that comprises the amino acid sequence of any one of items (A-i) to (A-ix) defined above. The amino acid sequences of SEQ ID NO: 1 to 9 recited in these items are amino acid sequences of the klebicins identified by the inventors. Preferably, the amino acid sequence of the first segment is the amino acid sequence of items (A-i) to (A-ix) defined above.

However, the invention is not limited to klebicins having first segments of the specific klebicins identified by the inventors. Instead of the amino acid sequences of items (A-i)

to (A-ix), the first segment may comprise an amino acid sequence of any one of items (B-i) to (B-ix), respectively, defined above. The wording "wherein the first segment comprises an amino acid sequence having at least 70% sequence identity to the amino acid sequence from amino acid residue x to y of SEQ ID NO: Z" (wherein x and y stand for the start and end positions indicated and Z stands for the number of the SEQ ID) means that the amino acid sequence of the first segment has preferably at least the same number of amino acid residues as the sequence from amino acid residue x to y of SEQ ID NO: Z and has at least the indicated sequence identity over the entire length from residue x to y of SEQ ID NO: Z. This principle applies to all items (B-i) to (B-ix) and to other sequence identities defined herein. Herein, the determination of sequence identities is done using Clustal Omega (CLUSTAL O 1.2.4) based on standard parameters. Preferably, the amino acid sequence of the first segment is that of any one of items (B-i) to (B-ix). The wording "wherein the amino acid sequence of the first segment has at least 70% sequence identity to the amino acid sequence from amino acid residue x to y of SEQ ID NO: Z" means that the amino acid sequence of the first segment has at least the same number of amino acid residues as the sequence from amino acid residue x to y of SEQ ID NO: Z and has the indicated sequence identity over the entire length from residue x to y of SEQ ID NO: Z. This applies to all items (B-i) to (B-ix) and to corresponding sequence identities defined herein.

In another embodiment, the first segment comprises an amino acid sequence of any one of items (C-i) to (C-ix) as defined above. Preferably, the amino acid sequence of the first segment is as defined in any one of items (C-i) to (C-ix) as defined above. The definitions of items (C-i) to (C-ix) mean that the amino acid sequence is that of the indicated amino acid residue range of the indicated SEQ ID NO except for the indicated number of substitutions, additions, insertions and/or deletions.

Where the protein is defined herein by a number or numerical range of amino acid substitutions, additions, insertions and/or deletions, these amino acid substitutions, additions, insertions or deletions may be combined, but the given number or numerical range refers to the sum of all amino acid substitutions, additions, insertions and deletions. Among amino acid substitutions, additions, insertions and deletions, amino acid substitutions, additions, and deletions are preferred. The term "insertion" relates to insertions within the amino acid sequence of a reference sequence, i.e. excluding additions at the C- or N-terminal end. The term "addition" means additions at the C- or N-terminal end of the amino acid sequence of a reference sequence. A deletion may be a deletion of a terminal or an internal amino acid residue of a reference sequence. The term "reference sequence" is used herein to refer to an amino acid sequence of the sequence listing based on which an amino acid sequence of a protein of the invention is defined. For example, in item (A-i) the reference sequence is SEQ ID NO: 1.

In items (B), any one of the sequence identities may be at least 75%, preferably at least 80%, more preferably at least 85%, even more preferably at least 90%, even more preferably at least 95%, and most preferably at least 97%. In items (C), the number of said amino acid substitutions, additions, insertions and/or deletions is from 1 to 30, preferably from 1 to 20, more preferably from 1 to 10, and most preferably from 1 to 5 compared to any one of said amino acid sequences.

Accordingly, the following items (i) to (ix) of each of items (B) and (C) define preferred embodiment of the first segment of the protein of the invention. The first segment of the protein of the invention preferably comprises any of the following amino acid sequences:

(B-i) having at least 75%, preferably at least 80%, more preferably at least 85%, even more preferably at least 90%, and most preferably at least 95% sequence identity to the amino acid sequence from amino acid residue 1 to 128 of SEQ ID NO: 1, (B-ii) having at least 75%, preferably at least 80%, more preferably at least 85%, even more preferably at least 90%, and most preferably at least 95% sequence identity to the amino acid sequence from amino acid residue 1 to 127 of SEQ ID NO: 2, (B-iii) having at least 75%, preferably at least 80%, more preferably at least 85%, even more preferably at least 90%, and most preferably at least 95% sequence identity to the amino acid sequence from amino acid residue 1 to 123 of SEQ ID NO: 3, (B-iv) having at least 75%, preferably at least 80%, more preferably at least 85%, even more preferably at least 90%, and most preferably at least 95% sequence identity to the amino acid sequence from amino acid residue 1 to 118 of SEQ ID NO: 4, (B-v) having at least 75%, preferably at least 80%, more preferably at least 85%, even more preferably at least 90%, and most preferably at least 95% sequence identity to the amino acid sequence from amino acid residue 1 to 170 of SEQ ID NO: 5, (B-vi) having at least 75%, preferably at least 80%, more preferably at least 85%, even more preferably at least 90%, and most preferably at least 95% sequence identity to the amino acid sequence from amino acid residue 1 to 172 of SEQ ID NO: 6, (B-vii) having at least 75%, preferably at least 80%, more preferably at least 85%, even more preferably at least 90%, and most preferably at least 95% sequence identity to the amino acid sequence from amino acid residue 1 to 255 of SEQ ID NO: 7, (B-viii) having at least 75%, preferably at least 80%, more preferably at least 85%, even more preferably at least 90%, and most preferably at least 95% sequence identity to the amino acid sequence from amino acid residue 1 to 288 of SEQ ID NO: 8, or (B-ix) having at least 75%, preferably at least 80%, more preferably at least 85%, even more preferably at least 90%, and most preferably at least 95% sequence identity to the amino acid sequence from amino acid residue 1 to 236 of SEQ ID NO: 9; or (C-i) having from 1 to 30, preferably from 1 to 20, more preferably from 1 to 10 amino acid substitutions, additions, insertions and/or deletions compared to the amino acid sequence of from amino acid 1 to 128 of SEQ ID NO: 1, (C-ii) having from 1 to 30, preferably from 1 to 20, more preferably from 1 to 10 amino acid substitutions, additions, insertions and/or deletions compared to the amino acid sequence of from amino acid 1 to 127 of SEQ ID NO: 2, (C-iii) having from 1 to 30, preferably from 1 to 20, more preferably from 1 to 10 amino acid substitutions, additions, insertions and/or deletions compared to the amino acid sequence of from amino acid 1 to 123 of SEQ ID NO: 3, (C-iv) having from 1 to 30, preferably from 1 to 20, more preferably from 1 to 10 amino acid substitutions, additions, insertions and/or deletions compared to the amino acid sequence of from amino acid 1 to 118 of SEQ ID NO: 4, (C-v) having from 1 to 30, preferably from 1 to 20, more preferably from 1 to 10 amino acid substitutions, additions, insertions and/or deletions compared to the amino acid sequence of from amino acid 1 to 170 of SEQ ID NO: 5, (C-vi) having from 1 to 30, preferably from 1 to 20, more preferably from 1 to 10 amino acid substitutions, additions, insertions and/or deletions compared to the amino acid sequence of from amino acid 1 to 172 of SEQ ID NO: 6, (C-vii) having from 1 to 30, preferably from 1 to 20, more preferably from 1 to 10 amino acid substitutions, additions, insertions and/or deletions compared to the amino acid sequence of from amino acid 1 to 255 of SEQ ID NO: 7, (C-viii) having from 1 to 30, preferably from 1 to 20, more preferably from 1 to 10 amino acid substitutions, additions, insertions and/or deletions compared to the amino acid sequence of from amino acid 1 to 288 of SEQ ID NO: 8, or (C-ix) having from 1 to 30, preferably from 1 to 20, more preferably from 1 to 10 amino acid substitutions, additions, insertions and/or deletions compared to the amino acid sequence of from amino acid 1 to 236 of SEQ ID NO: 9.

In another embodiment, the amino acid sequence of the first segment of the protein of the invention preferably has:

(B-i) at least 75%, preferably at least 80%, more preferably at least 85%, even more preferably at least 90%, and most preferably at least 95% sequence identity to the amino acid sequence from amino acid residue 1 to 128 of SEQ ID NO: 1, (B-ii) at least 75%, preferably at least 80%, more preferably at least 85%, even more preferably at least 90%, and most preferably at least 95% sequence identity to the amino acid sequence from amino acid residue 1 to 127 of SEQ ID NO: 2, (B-iii) at least 75%, preferably at least 80%, more preferably at least 85%, even more preferably at least 90%, and most preferably at least 95% sequence identity to the amino acid sequence from amino acid residue 1 to 123 of SEQ ID NO: 3, (B-iv) at least 75%, preferably at least 80%, more preferably at least 85%, even more preferably at least 90%, and most preferably at least 95% sequence identity to the amino acid sequence from amino acid residue 1 to 118 of SEQ ID NO: 4, (B-v) at least 75%, preferably at least 80%, more preferably at least 85%, even more preferably at least 90%, and most preferably at least 95% sequence identity to the amino acid sequence from amino acid residue 1 to 170 of SEQ ID NO: 5, (B-vi) at least 75%, preferably at least 80%, more preferably at least 85%, even more preferably at least 90%, and most preferably at least 95% sequence identity to the amino acid sequence from amino acid residue 1 to 172 of SEQ ID NO: 6, (B-vii) at least 75%, preferably at least 80%, more preferably at least 85%, even more preferably at least 90%, and most preferably at least 95% sequence identity to the amino acid sequence from amino acid residue 1 to 255 of SEQ ID NO: 7, (B-viii) at least 75%, preferably at least 80%, more preferably at least 85%, even more preferably at least 90%, and most preferably at least 95% sequence identity to the amino acid sequence from amino acid residue 1 to 288 of SEQ ID NO: 8, or (B-ix) at least 75%, preferably at least 80%, more preferably at least 85%, even more preferably at least 90%, and most preferably at least 95% sequence identity to the amino acid sequence from amino acid residue 1 to 236 of SEQ ID NO: 9;

or (C-i) from 1 to 30, preferably from 1 to 20, more preferably from 1 to 10 amino acid substitutions, additions, insertions and/or deletions compared to the amino acid sequence of from amino acid residue 1 to 128 of SEQ ID NO: 1, (C-ii) from 1 to 30, preferably from 1 to 20, more preferably from 1 to 10 amino acid substitutions, additions, insertions and/or deletions compared to the amino acid sequence of from amino acid residue 1 to 127 of SEQ ID NO: 2, (C-iii) from 1 to 30, preferably from 1 to 20, more preferably from 1 to 10 amino acid substitutions, additions, insertions and/or deletions compared to the amino acid sequence of from amino acid residue 1 to 123 of SEQ ID NO: 3, (C-iv) from 1 to 30, preferably from 1 to 20, more preferably from 1 to 10 amino acid substitutions, additions, insertions and/or deletions compared to the amino acid sequence of from amino acid residue 1 to 118 of SEQ ID NO: 4, (C-v) from 1 to 30, preferably from 1 to 20, more preferably from 1 to 10 amino acid substitutions, additions, insertions and/or deletions compared to the amino acid sequence of from amino acid residue 1 to 170 of SEQ ID NO: 5, (C-vi) from 1 to 30, preferably from 1 to 20, more preferably from 1 to 10 amino acid substitutions, additions, insertions and/or deletions compared to the amino acid sequence of from amino acid residue 1 to 172 of SEQ ID NO: 6, (C-vii) from 1 to 30, preferably from 1 to 20, more preferably from 1 to 10 amino acid substitutions, additions, insertions and/or deletions compared to the amino acid sequence of from amino acid residue 1 to 255 of SEQ ID NO: 7, (C-viii) from 1 to 30, preferably from 1 to 20, more preferably from 1 to 10 amino acid substitutions, additions, insertions and/or deletions compared to the amino acid sequence of from amino acid residue 1 to 288 of SEQ ID NO: 8, or (C-ix) from 1 to 30, preferably from 1 to 20, more preferably from 1 to 10 amino acid substitutions, additions, insertions and/or deletions compared to the amino acid sequence of from amino acid residue 1 to 236 of SEQ ID NO: 9.

Second Segment of the Protein of the Invention

Since the protein (klebicin) of the invention has both a first and a second segment, the protein may be defined by both its first and second segment. Thus, the protein may be defined by a combination of any one of the above first segments with a second segment as defined herein.

The second segment of the protein of the invention provides the protein with its bactericidal or bacteriostatic activity against *Klebsiella*. The second segment preferably has a lipid II-cleaving activity or a pore-forming capability in a bacterial cell membrane. Such activities are known from other bacteriostatic or bactericidal bacterial proteins such as *E. coli* colicins.

The second segment may comprise or consist of the amino acid sequence of any one of items (D-i) to (D-ix) defined above. Preferably, the amino acid sequence of the first segment is the amino acid sequence of items (D-i) to (D-ix) defined above. Where a definition of a first segment is combined with that of a second segment, first and second segments defined based on same SEQ ID NO as reference sequence are preferably combined. For example, a protein may be defined by having a first segment based on item (A-ii) and a second segment based on item (D-ii).

However, the invention is not limited to klebicins having second segments of the specific klebicins identified by the inventors. Instead of the amino acid sequences of items (D-i) to (D-ix), the second segment may comprise or consist of an amino acid sequence of any one of items (E-i) to (E-ix). Preferably, the amino acid sequence of the second segment is that of any one of items (E-i) to (E-ix).

In another embodiment, the second segment comprises or consists of an amino acid sequence of any one of items (F-i) to (F-ix) as defined above. Preferably, the amino acid sequence of the first segment is as defined in any one of items (F-i) to (F-ix) as defined above.

The following items (i) to (ix) of each of items (E) and (F) define preferred second segments. In one embodiment, the second segment of the protein of the invention preferably comprises any of the following amino acid sequences:

(E-i) having at least 75%, preferably at least 80%, more preferably at least 85%, even more preferably at least 90%, and most preferably at least 95% sequence identity to the segment from amino acid residue 129 to 278 of SEQ ID NO: 1, (E-ii) having at least 75%, preferably at least 80%, more preferably at least 85%, even more preferably at least 90%, and most preferably at least 95% sequence identity to the segment from amino acid residue 128 to 276 of SEQ ID NO: 2, (E-iii) having at least 75%, preferably at least 80%, more preferably at least 85%, even more preferably at least 90%, and most preferably at least 95% sequence identity to the segment from amino acid residue 124 to 272 of SEQ ID NO: 3, (E-iv) having at least 75%, preferably at least 80%, more preferably at least 85%, even more preferably at least 90%, and most preferably at least 95% sequence identity to the segment from amino acid residue 119 to 266 of SEQ ID NO: 4, (E-v) having at least 75%, preferably at least 80%, more preferably at least 85%, even more preferably at least 90%, and most preferably at least 95% sequence identity to the segment from amino acid residue 171 to 377 of SEQ ID NO: 5, (E-vi) having at least 75%, preferably at least 80%, more preferably at least 85%, even more preferably at least 90%, and most preferably at least 95% sequence identity to the segment from amino acid residue 173 to 379 of SEQ ID NO: 6, (E-vii) having at least 75%, preferably at least 80%, more preferably at least 85%, even more preferably at least 90%, and most preferably at least 95% sequence identity to the segment from amino acid residue 256 to 452 of SEQ ID NO: 7, (E-viii) having at least 75%, preferably at least 80%, more preferably at least 85%, even more preferably at least 90%, and most preferably at least 95% sequence identity to the segment from amino acid residue 289 to 466 of SEQ ID NO: 8, or (E-ix) having at least 75%, preferably at least 80%, more preferably at least 85%, even more preferably at least 90%, and most preferably at least 95% sequence identity to the segment from amino acid residue 237 to 414 of SEQ ID NO: 9;

or (F-i) having from 1 to 20, preferably from 1 to 15, more preferably from 1 to 10 amino acid substitutions, additions, insertions and/or deletions compared to the amino acid sequence of from amino acid 129 to 278 of SEQ ID NO: 1, (F-ii) having from 1 to 20, preferably from 1 to 15, more preferably from 1 to 10 amino acid substitutions, additions, insertions and/or deletions compared to the amino acid sequence of from amino acid 128 to 276 of SEQ ID NO: 2, (F-iii) having from 1 to 20, preferably from 1 to 15, more preferably from 1 to 10 amino acid substitutions, additions, insertions and/or deletions compared to the amino acid sequence of from amino acid 124 to 272 of SEQ ID NO: 3, (F-iv) having from 1 to 20, preferably from 1 to 15, more preferably from 1 to 10 amino acid substitutions, additions, insertions and/or deletions compared to the amino acid sequence of from amino acid 119 to 266 SEQ ID NO: 4, (F-v) having from 1 to 30, preferably from 1 to 20, more preferably from 1 to 10 amino acid substitutions, additions, insertions and/or deletions compared to the amino acid sequence of from amino acid 171 to 377 of SEQ ID NO: 5, (F-vi) having from 1 to 30, preferably from 1 to 20, more preferably from 1 to 10 amino acid substitutions, additions, insertions and/or deletions compared to the amino acid sequence of from amino acid 173 to 379 SEQ ID NO: 6, (F-vii) having from 1 to 30, preferably from 1 to 20, more preferably from 1 to 10 amino acid substitutions, additions, insertions and/or deletions compared to the amino acid sequence of from amino acid 256 to 452 of SEQ ID NO: 7, (F-viii) having from 1 to 30, preferably from 1 to 20, more preferably from 1 to 10 amino acid substitutions, additions, insertions and/or deletions compared to the amino acid sequence of from amino acid 289 to 466 of SEQ ID NO: 8, or (F-ix) having from 1 to 30, preferably from 1 to 20, more preferably from 1 to 10 amino acid substitutions, additions, insertions and/or deletions compared to the amino acid sequence of from amino acid 237 to 414 of SEQ ID NO: 9.

In another embodiment, the amino acid sequence of the second segment of the protein of the invention preferably has:

(E-i) at least 75%, preferably at least 80%, more preferably at least 85%, even more preferably at least 90%, and most preferably at least 95% sequence identity to the segment from amino acid residue 129 to 278 of SEQ ID NO: 1, (E-ii) at least 75%, preferably at least 80%, more preferably at least 85%, even more preferably at least 90%, and most preferably at least 95% sequence identity to the segment from amino acid residue 128 to 276 of SEQ ID NO: 2, (E-iii) at least 75%, preferably at least 80%, more preferably at least 85%, even more preferably at least 90%, and most preferably at least 95% sequence identity to the segment from amino acid residue 124 to 272 of SEQ ID NO: 3, (E-iv) at least 75%, preferably at least 80%, more preferably at least 85%, even more preferably at least 90%, and most preferably at least 95% sequence identity to the segment from amino acid residue 119 to 266 of SEQ ID NO: 4, (E-v) at least 75%, preferably at least 80%, more preferably at least 85%, even more preferably at least 90%, and most preferably at least 95% sequence identity to the segment from amino acid residue 171 to 377 of SEQ ID NO: 5, (E-vi) at least 75%, preferably at least 80%, more preferably at least 85%, even more preferably at least 90%, and most preferably at least 95% sequence identity to the segment from amino acid residue 173 to 379 of SEQ ID NO: 6, (E-vii) at least 75%, preferably at least 80%, more preferably at least 85%, even more preferably at least 90%, and most preferably at least 95% sequence identity to the segment from amino acid residue 256 to 452 of SEQ ID NO: 7, (E-viii) at least 75%, preferably at least 80%, more preferably at least 85%, even more preferably at least 90%, and most preferably at least 95% sequence identity to the segment from amino acid residue 289 to 466 of SEQ ID NO: 8, (E-ix) at least 75%, preferably at least 80%, more preferably at least 85%, even more preferably at least 90%, and most preferably at least 95% sequence identity to the segment from amino acid residue 237 to 414 of SEQ ID NO: 9;

or (F-i) from 1 to 20, preferably from 1 to 15, more preferably from 1 to 10 amino acid substitutions, additions, insertions and/or deletions compared to the amino acid sequence of from amino acid 129 to 278 of SEQ ID NO: 1, (F-ii) from 1 to 20, preferably from 1 to 15, more preferably from 1 to 10 amino acid substitutions, additions, insertions and/or deletions compared to the amino acid sequence of from amino acid 128 to 276 of SEQ ID NO: 2, (F-iii) from 1 to 20, preferably from 1 to 15, more preferably from 1 to 10 amino acid substitutions, additions, insertions and/or deletions compared to the amino acid sequence of from amino acid 124 to 272 of SEQ ID NO: 3, (F-iv) from 1 to 20, preferably from 1 to 15, more preferably from 1 to 10 amino acid substitutions, additions, insertions and/or deletions compared to the amino acid sequence of from amino acid 119 to 266 SEQ ID NO: 4, (F-v) from 1 to 30, preferably from 1 to 20, more preferably from 1 to 10 amino acid substitutions, additions, insertions and/or deletions compared to the amino acid sequence of from amino acid 171 to 377 of SEQ ID NO: 5, (F-vi) from 1 to 30, preferably from 1 to 20, more preferably from 1 to 10 amino acid substitutions, additions, insertions and/or deletions compared to the amino acid sequence of from amino acid 173 to 379 SEQ ID NO: 6, (F-vii) from 1 to 30, preferably from 1 to 20, more preferably from 1 to 10 amino acid substitutions, additions, insertions and/or deletions compared to the amino acid sequence of from amino acid 256 to 452 of SEQ ID NO: 7, (F-viii) from 1 to 30, preferably from 1 to 20, more preferably from 1 to 10 amino acid substitutions, additions, insertions and/or deletions compared to the amino acid sequence of from amino acid 289 to 466 of SEQ ID NO: 8, (F-ix) from 1 to 30, preferably from 1 to 20, more preferably from 1 to 10 amino acid substitutions, additions, insertions and/or deletions compared to the amino acid sequence of from amino acid 237 to 414 of SEQ ID NO: 9.

In the invention, any first segment mentioned above may be combined with any second segment to a protein of the invention. In one embodiment, the protein of the invention comprises a first segment of any one of items (i)-(iv) and a second segment of any one of items (i)-(iv), irrespective of whether the first segment belongs to item (A), (B) or (C) and whether the second segment belongs to items (D), (E), or (F). However, in one embodiment, the protein of the invention comprises a first segment of any one of items (C-i)-(C-iv) and a second segment of any one of items (F-i)-(F-iv).

In another embodiment, the protein of the invention comprises a first segment of any one of items (v)-(ix) and a second segment of any one of items (v)-(ix), irrespective of whether the first segment belongs to item (A), (B) or (C) and whether the second segment belongs to items (D), (E), or (F). However, in one embodiment, the protein of the invention comprises a first segment of any one of items (C-v)-(C-ix) and a second segment of any one of items (F-v)-(F-ix).

Other Embodiments are as Follows in one embodiment, the protein of the invention may have a first segment that comprises or consists of any of the amino acid sequences of items (A-i) to (A-iv), (B-i) to (B-iv), or (C-i) to (C-iv), in a most generic of preferred embodiments, and a second segment that comprises or consists of any one of the amino acid sequences of items (D-i) to (D-iv), (E-i) to (E-iv), or (F-i) to (F-iv). Preferably, the first segment comprises or consists of any one of the amino acid sequences of items (A-i) to (A-iii), (B-i) to (B-iii), or (C-i) to (C-iii) and the second segment comprises any one of the amino acid sequences of (D-i) to (D-iii), (E-i) to (E-iii), or (F-i) to (F-iii). More preferably, the first segment comprises any one of the amino acid sequences of (A-ii), (B-ii) or (C-ii), and the second segment comprises any one of the amino acid sequence of (D-ii), (E-ii) or (F-ii). Even more preferably, the first segment comprises the amino acid sequence of (A-ii) and the second segment comprises the amino acid sequence of (D-ii).

In another embodiment, the first segment comprises any one of the amino acid sequences of items (A-v) to (A-ix), (B-v) to (B-ix), or (C-v) to (C-ix), and the second segment comprises any one of the amino acid sequences of (D-v) to (D-ix), (E-v) to (E-ix), or (F-v) to (F-ix). In a preferred embodiment, the first segment comprises any one of the amino acid sequences of items (A-v), (A-vi), (B-v), (B-vi), (C-v) and (C-vi), and the second segment comprises any one of the amino acid sequences of items (D-v), (D-vi), (E-v), (E-vi), (F-v) and (F-vi). In a more preferred embodiment, the first segment comprises or consists of the amino acid sequence of item (A-v) or (A-vi) and the second segment comprises or consists of the amino acid sequence of item (D-v) or (D-vi). In another preferred embodiment, the first segment comprises or consists of the amino acid sequence of item (A-vii) and the second segment comprises or consists of the amino acid sequence of item (D-vii).

In a further alternative embodiment, the first segment comprises any one of the amino acid sequences of items (A-viii), (A-ix), (B-viii), (B-ix), (C-viii) or (C-ix), and the second segment comprises any one of the amino acid sequences of items (D-viii), (D-ix), (E-viii), (E-ix), (F-viii) or (F-ix). Preferably, the first segment comprises or consists of the amino acid sequence of item (A-viii) or (A-ix) and the second segment comprises or consists of the amino acid sequence of item (D-viii) or (D-ix).

Further preferred embodiments of the protein of the invention are as defined above in items (a-i) to (a-ix), (b-i) to (b-ix), and (c-i) to (c-ix). In items (b), the wording "amino acid sequence having at least 70% sequence identity to the amino acid sequence of SEQ ID NO: Z" (wherein Z stands for the number of the SEQ ID NO) means that the amino acid sequence has at least the same number of amino acid residues as the sequence of SEQ ID NO: Z and has at least the indicated sequence identity over the entire length of SEQ ID NO: Z. This applies to all items (b-i) to (b-ix) and to corresponding sequence identities defined herein. The definitions of items (c-i) to (c-ix) mean that the amino acid sequence is that of the entire amino sequence of the indicated SEQ ID NO except for the indicated number of substitutions, additions, insertions or deletions.

Alternatively, the amino acid sequence of the inventive protein may be defined as follows:

(b') in one embodiment, the amino acid sequence of the protein of the invention is (b'-i) at least 70%, preferably at least 80%, more preferably at least 90%, and even more preferably at least 95% identical to the amino acid sequence of SEQ ID NO: 1, (b'-ii) at least 70%, preferably at least 80%, more preferably at least 90%, and even more preferably at least 95% identical to the amino acid sequence of SEQ ID NO: 2, (b'-iii) at least 70%, preferably at least 80%, more preferably at least 90%, and even more preferably at least 95% identical to the amino acid sequence of SEQ ID NO: 3, (b'-iv) at least 70%, preferably at least 80%, more preferably at least 90%, and even more preferably at least 95% identical to the amino acid sequence of SEQ ID NO: 4, (b'-v) at least 70%, preferably at least 80%, more preferably at least 90%, and even more preferably at least 95% identical to the amino acid sequence of SEQ ID NO: 5, (b'-vi) at least 70%, preferably at least 80%, more preferably at least 90%, and even more preferably at least 95% identical to the amino acid sequence of SEQ ID NO: 6, (b'-vii) at least 70%, preferably at least 80%, more preferably at least 90%, and even more preferably at least 95% identical to the amino acid sequence of SEQ ID NO: 7, (b'-viii) at least 70%, preferably at least 80%, more preferably at least 90%, and even more preferably at least 95% identical to the amino acid sequence of SEQ ID NO: 8, or (b'-ix) at least 70%, preferably at least 80%, more preferably at least 90%, and even more preferably at least 95% identical to the amino acid sequence of SEQ ID NO: 9;

(b") in another embodiment, the amino acid sequence of the protein of the invention shares (b"-i) at least 70%, preferably at least 80%, more preferably at least 90%, and even more preferably at least 95% sequence identity to the amino acid sequence of SEQ ID NO: 1, (b"-ii) at least 70%, preferably at least 80%, more preferably at least 90%, and even more preferably at least 95% sequence identity to the amino acid sequence of SEQ ID NO: 2, (b"-iii) at least 70%, preferably at least 80%, more preferably at least 90%, and even more preferably at least 95% sequence identity to the amino acid sequence of SEQ ID NO: 3, (b"-iv) at least 70%, preferably at least 80%, more preferably at least 90%, and even more preferably at least 95% sequence identity to the amino acid sequence of SEQ ID NO: 4, (b"-v) at least 70%, preferably at least 80%, more preferably at least 90%, and even more preferably at least 95% sequence identity to the amino acid sequence of SEQ ID NO: 5, (b"-vi) at least 70%, preferably at least 80%, more preferably at least 90%, and even more preferably at least 95% sequence identity to the amino acid sequence of SEQ ID NO: 6, (b"-vii) at least 70%, preferably at least 80%, more preferably at least 90%, and even more preferably at least 95% sequence identity to the amino acid sequence of SEQ ID NO: 7, (b"-viii) at least 70%, preferably at least 80%, more preferably at least 90%, and even more preferably at least 95% sequence identity to the amino acid sequence of SEQ ID NO: 8, or (b"-ix) at least 70%, preferably at least 80%, more preferably at least 90%, and even more preferably at least 95% sequence identity to the amino acid sequence of SEQ ID NO: 9.

Cytotoxic Activity of the Protein of the Invention

The klebicin of the invention is capable of exerting a cytotoxic effect on bacteria of genus *Klebsiella*, such as *K. pneumoniae, K. granulomatis, K. oxytoca, K. aerogenes, K. quasipneumoniae*, and *K. variicola*. Preferably, the klebicin of the invention is active against *K. pneumoniae* and *K. oxytoca*. *K. pneumoniae* is most preferred. The cytotoxic effect may be a bacteriostatic or a bacteriocidal effect. Whether the protein has a cytotoxic effect can be tested experimentally, e.g. using the assay of Example 4. In one embodiment, said *Klebsiella* is antibiotic-resistant such as resistant to carbapenem, and said protein is a protein selected from items (i) to (iv), (vii) and (viii), preferably from (i) to (iv), of any of the embodiments defined above. The proteins selected from items (i) to (iv), (vii) and (viii) are proteins defined using SEQ ID NOs: 1 to 4, 7 or 8 as a reference sequence.

The protein of the invention may have a pore forming activity in cell membranes of *Klebsiella* cells. In the present invention, the proteins of items (a-v) to (a-ix) of SEQ ID NOs: 5 to 9 and the respective derivatives of items (b-v) to (b-ix) and (c-v) to (c-ix) have pore-forming activity. The pore-forming activity is envisaged to be due to the presence of the second amino acid sequence segment of these proteins.

Another class of proteins of the invention are envisaged to have a lipid II-cleaving activity, by analogy to the activity of *E. coli* colicin M. The inventors envisage that the proteins of this class have a peptidoglycanase activity that specifically cleaves the bond between the lipid moiety and the pyrophosphoryl group of the peptidoglycan lipid I and lipid II intermediates, located at the periplasmic side of the inner membrane, as determined for *E. coli* colicin M (Gross and Braun, Mol. Gen. Genet. 251 (1996) 388-396; Barreteau et al., Microbial Drug Resistance 18 (2012), 222-229). The released C55-polyisoprenol no longer translocates MurNAc-pentapeptide-GlcNAc across the cytoplasmic membrane. These klebicins are thus envisaged to exert toxicity against *Klebsiella* cells after they have been taken up across the outer cell wall into the periplasm. This property of the protein of the invention may be assayed according to the standard assay for colicin M activity described by El Ghachi et al., J. Biol. Chem. 281 (2006) 22761-22772 using lipid I as the substrate. In the present invention, the proteins of items (a-i) to (a-iv) of SEQ ID NOs 1 to 4 and the respective derivatives of items (b-i) to (b-iv) and (c-i) to (c-iv) have peptidoglycanase or lipid II-cleaving activity. This activity is envisaged to be due to the presence of the second amino acid sequence segment of these proteins.

The cytotoxic activity of the protein of the invention is preferably such that said protein and a comparative protein of the amino acid sequence of the SEQ ID NO: 1 produces spots free of viable bacteria of sensitive *Klebsiella quasipneumoniae* subsp. *similipneumoniae* SB30 (DSM 28212) at least of the same diameter 16 hours after spotting 20 microliters of each of a solution of said protein and of the comparative protein onto a lawn of the sensitive *Klebsiella* strain on an agar plate and subsequent incubation of the agar plate at 37° C., wherein the concentration of said protein in the solution is at most 5 times that of the solution of the respective comparative protein. The solution is an aqueous solution. This test can be carried out as described in Reference Example 1. Protein concentrations are determined in terms of weight per volume as also described in Reference Example 1.

In one embodiment, the protein of the invention is one of any one of items (b-i) to (b-ix) or (c-i) to (c-ix) above and has a cytotoxic activity such that said protein and a comparative protein of the amino acid sequence of the reference sequence of the SEQ ID NO of said item (b-i) to (b-ix) or (c-i) to (c-ix), respectively, produce spots free of viable bacteria of the sensitive *Klebsiella* strain *quasipneumoniae* subsp. *similipneumoniae* SB30 (DSM 28212) at least of the same diameter 16 hours after spotting 20 microliters of each of a solution of said protein and of the comparative protein onto a lawn of the sensitive *Klebsiella* strain on an agar plate and subsequent incubation of the agar plate at 37° C., wherein the concentration of said protein in the solution is at most 5 times that of the solution of the respective comparative protein. The solution is an aqueous solution. This test can be carried out as described in Reference Example 1. Protein concentrations are determined in terms of weight per volume as also described in Reference Example 1.

Consensus Sequences of Proteins of the Invention

The protein of the invention comprises an amino acid sequence selected from the group consisting of SEQ ID NO: 22 to 24, wherein each X stands for any one of the 20 standard amino acid residues or absence of an amino acid residue and J stands for either L (leucine) or I (isoleucine), preferably X stands for any one of the 20 standard amino acid residues and J for either L (leucine) or I (isoleucine).

The 20 standard amino acid residues are: A (alanine), C (cysteine), D (aspartic acid), E (glutamic acid), F (phenylalanine), G (glycine), H (histidine), I (isoleucine), K (lysine), L (leucine), M (methionine), N (asparagine), P (proline), Q (glutamine), R (arginine), S (serine), T (threonine), V (valine), W (tryptophan) and Y (tyrosine).

In a preferred embodiment, the cytotoxic activity of said protein is such that said protein and a comparative protein of the amino acid sequence of SEQ ID NO: 1 produces spots free of viable bacteria of sensitive *Klebsiella quasipneumoniae* subsp. *similipneumoniae* SB30 (DSM 28212) at least of the same diameter 16 hours after spotting 20 microliters of each of a solution of said protein and of the comparative protein onto a lawn of the sensitive *Klebsiella* strain on an agar plate and subsequent incubation of the agar plate at 37° C., wherein the concentration of the protein in the solution is at most 5 times that of the solution of the comparative protein. The assay on the cytotoxic activity is carried out as described in Reference Example 1.

Proteins of the present invention with a similar mode-of-action against *Klebsiella* have conserved positions and/or amino acid sequence stretches in the amino acid sequence, preferably in the first and second segments. Conserved positions and/or amino acid sequence stretches have an increased likelihood of being relevant for the function of the protein of the invention. In the first amino acid sequence segment, the conserved positions or stretches generally relate to the functions of receptor binding and translocation. In the second amino acid sequence segment, the conserved positions or stretches generally relate to cytotoxicity against *Klebsiella*. The klebicins KpneM2, KvarM, KpneM and KaerM share a consensus sequence of SEQ ID NO: 22. The klebicins KaerA and KpneA share a consensus sequence of SEQ ID NO: 23. The klebicins Kpnela and Kvarla share a consensus sequence of SEQ ID NO: 24. Each X in SEQ ID NO: 22, 23 and 24 stands either for any one of the 20 standard amino acid residues or for no amino acid residue present at this position and J stands for either L (leucine) or I (isoleucine).

In particular, a klebicin with lipid II-cleaving activity (e.g. those defined with reference to SEQ ID NOs: 1-4) preferably has amino acid residues or amino acid sequence stretches corresponding to the following amino acid residues or amino acid sequence stretches: 1M, 2S/T, 3D/E, 4T, 5L/M, 7V, 9A, 22G, 24G, 50S, 91T, 97P, 132P, 138H, 139Y, 142G, 144G, 155G, 156L, 176G, 184F, 199L, 200G, 2021, 203T, 206TEGTL210 (SEQ ID NO: 25), 2121, 216G, 218W, 220YNGV223 (SEQ ID NO: 26), 225RAFNDTYD232 (SEQ ID NO: 27), 234N, 239R, 243A, 247T, 255G, 258Y, 260I, 262P, 262G, 271S, 272G;

wherein the number preceding a one-letter code of an amino acid residue indicates the position in SEQ ID NO: 22, and a number following a one-letter code of an amino acid residue indicates the position in SEQ ID NO: 22 of the preceding amino acid residue in case of a stretch of two or more amino acid residues. Two or more amino acid residues separated by "/" means that any one of the indicated residues is at the position corresponding to the indicated position in SEQ ID NO: 22. The wording "amino acid residues or amino acid sequence stretches corresponding to . . . " means that the position in a given protein may differ from the position of SEQ ID NO: 22. However, the corresponding position can be determined by aligning the amino acid sequence of the protein with those of SEQ ID NOs: 1-4 and 22 (as shown in FIG. 10A) and determining the corresponding position by counting the residues of the amino acid sequence of the protein starting with the N-terminal first amino acid sequence.

A klebicin with pore forming activity defined with reference to SEQ ID NOs: 5 and 6 has preferably amino acid residues or amino acid sequence stretches corresponding to the following amino acid residues or amino acid sequence stretches: 1M, 4E, 9V, 11G, 13N, 18V, 20WGG22, 25GNG-NNGGAG33 (SEQ ID NO: 28), 36G, 39G, 45G, 47T, 52L, 65P, 67N, 68P, 72GAPW75 (SEQ ID NO: 29), 80S, 82K, 84A, 90AN91, 94KP95, 97KFKANIQN104 (SEQ ID NO: 30), 106K, 111GSL113, 115SP116, 188V, 120KS121, 123SSGDVDTY130 (SEQ ID NO: 31), 132VSFGKEKYNV141 (SEQ ID NO: 32), 143YNRKKDSFT151 (SEQ NO ID: 33), 154YVDGGA159 (SEQ ID NO: 34), 161KPEHSMKDQAIAVV174 (SEQ ID NO: 35), 176LYLLNE181 (SEQ ID NO: 36), 186VI187, 189T, 193III194, 197SG198, 200T, 202SGKLG206 (SEQ ID NO: 37), 208KY209, 212LA213, 217A, 220I, 222NFQGKK227 (SEQ ID NO: 38), 229RSF231, 233DAM235, 237S, 244NP245, 247MKL249, 251QADK254 (SEQ ID NO: 39), 259NAL261, 263Q, 266LS267, 269LADRFKGL277 (SEQ ID NO: 40), 279AFTW282 (SEQ ID NO: 41), 284DRLLKA289 (SEQ ID NO: 42), 291KI292, 294DGVVTGVTTG303 (SEQ ID NO: 43), 305WQ306, 308LA309, 311EVEAM-YLSGVAG322 (SEQ ID NO: 44), 324VALGI328 (SEQ ID NO: 45), 330T, 332MIS334, 337A, 341S, 343P, 346AV, 349ALTV352 (SEQ ID NO: 46), 354AVIGI358 (SEQ ID NO: 47), 3601, 362TSYI365 (SEQ ID NO: 48), 367AD368, 370AKALNNAV377 (SEQ ID NO: 49), 380LFK382;

wherein the number preceding a one-letter code of an amino acid residue indicates the position in SEQ ID NO: 23, and a number following a one-letter code of an amino acid residue indicates the position in SEQ ID NO: 23 of the preceding amino acid residue in case of a stretch of two or more amino acid residues. Two or more amino acid residues separated by "/" means that any one of the indicated residues is at the position corresponding to the indicated position in SEQ ID NO: 23. The wording "amino acid residues or amino acid sequence stretches corresponding to . . . " means that the position in a given protein may differ from the position of SEQ ID NO: 23. However, the corresponding position can be determined by aligning the amino acid sequence of the protein with those of SEQ ID NOs: 5-6 and 23 (as shown in FIG. 10B) and determining the corresponding position by counting the residues of the amino acid sequence of the protein starting with the N-terminal first amino acid sequence. SEQ ID NO: 23 is that given at the end of this specification.

A klebicin with pore forming activity defined with reference to SEQ ID NOs: 8 and 9 has preferably amino acid residues or amino acid sequence stretches corresponding to the following amino acid residues or amino acid sequence stretches:

```
                                          (SEQ ID NO: 50)
1MPGFNYGGKGDGTNWSSERGTGPEPGGGSRGNGGDRDNSRGGA

GNRGNWAGSGPLSAALINDSIAEALEKQLPRNTVEATSTPAYKK

MRAAFDALPLDKQPEARAQITKAWQSAHDAMPD120,
121K/R, (SEQ ID NO: 51)
122TTTTENVGGGKNGHNVTRSTPNWLKEKMKGLNQQVNNDLSG
```

-continued
```
ALAQHQKAEADARAKAEAAAKAK185,
238A, 239E/A, (SEQ ID NO: 52)
240AKAKAEAEAKAKAEA254,
255A/E, (SEQ ID NO: 53)
256AKAKAEA262,
263E/A, (SEQ ID NO: 54)
264AKAKAEAEAKAKAEAEAKAKAEADAVKDAVKFTADFYKEVFS

VYGEKAEQLANLLATQAKGKNIRNIDDALKAYEKHKTNINKKINA

QDRAAIAKALESVDVKEAAKNFAKFSKGLGYVGPTMDWDLVLELR

KAIKEDNWR405,
406S/T, (SEQ ID NO: 55)
407FFVKIEAIAISFGATQLAALAFASLLGAPVGLLGYALIMAGI

GALVSDDWDAANKIIGI466;
``` wherein a number preceding a one-letter code of an amino acid residue indicate the position in SEQ ID NO: 24, and a number following a one-letter code of an amino acid residue indicates the position in SEQ ID NO: 24 of the preceding amino acid residue in case of a stretch of two or more amino acid residues. Two or more amino acid residues separated by "/" means that any one of the indicated residues is at the position corresponding to the indicated position in SEQ ID NO: 24. The wording "amino acid residues or amino acid sequence stretches corresponding to . . . " means that the position in a given protein may differ from the position of SEQ ID NO: 24. However, the corresponding position can be determined by aligning the amino acid sequence of the protein with those of SEQ ID NOs: 8-9 and 24 (as shown in FIG. 10C) and determining the corresponding position by counting the residues of the amino acid sequence of the protein starting with the N-terminal first amino acid sequence.

The definitions given above with respect to the consensus sequences can be combined with the definitions given in the claims or the embodiments given in preceding sections.

In more detail, the definition of conserved residues may be combined with any definition of item (B-i) to (B-iv), (C-i) to (C-iv), (E-i) to (E-iv), (F-i) to (F-iv), (b-i) to (b-iv), and/or (c-i) to (c-iv) above to define amino acid residue that should not be changed. Depending on the specific reference sequence used for defining the protein of the invention, the indications of the amino acid positions given above are exchanged by the corresponding positions of the respective reference sequence. Corresponding positions in the reference sequence can e.g. be derived from the alignment shown in FIG. 10A-C.

Klebicin Compositions

The composition of the invention comprises one or more proteins (klebicins) of the invention as described above and optionally further components as the case requires such as a carrier. The composition may comprise one or more different proteins (klebicins) as defined herein, such as two, three or four different proteins (klebicins) as defined herein. "Different" means that the proteins differ in at least one amino acid residue. The composition may comprise two, three or more klebicins of the invention from the same class represented by any one of items (i) to (iv) above or of items (v) to (ix) above. Preferably, the composition contains at least two klebicins of the invention from different classes, such as at least one klebicin of the pore-forming type and at least one klebicin of the lipid II-cleaving type. The composition may further comprise one or more *E. coli* colicin or a derivative thereof e.g. as described in EP 3 097 783 A1, e.g. for concomitantly controlling pathogenic *E. coli* such as EHEC.

The invention also provides a composition comprising one or more proteins of the invention and one or more other bacteriocidal or bacteriostatic proteins. Such other bacteriocidal or bacteriostatic proteins may be *E. coli* colicins or *Salmonella* colicins (salmocins). *E. coli* colicin are known in the art and are described inter alia in EP3097783 A1. Salmocins are known and described in WO2018172065 A1.

As the protein of the invention is preferably produced by expression in plants or cells thereof, the composition may be a plant material or extract thereof, wherein the plant material is a material from a plant having expressed the protein, preferably *Nicotiana* or an edible plant having expressed said protein. An extract of plant material is an aqueous solution containing water-soluble proteins including a protein of the invention that is present or expressed in said plant material, or a dried product of such aqueous solution. The extract preferably has water-insoluble components of the plant material removed e.g. by filtration or centrifugation. The plant material may be a material from a plant selected from the group consisting of spinach, chard, beetroot, carrot, sugar beet, leafy beet, amaranth, *Nicotiana*, and/or said plant material is one or more leaves, roots, tubers, or seeds, or a crushed, milled or comminuted product of said leaves, roots, tubers, or seeds.

The composition or said extract from a plant material may be a solid or liquid composition, such as a solution or a dispersion, containing the klebicin(s) of the invention. The liquid composition may be aqueous, such as an aqueous solution. The concentration of said protein in said aqueous dispersion or solution may be from 0.0001 to 1 mg/ml, preferably from 0.001 to 0.1 mg/ml, more preferably from 0.005 to 0.05 mg/ml. If more than one klebicin capable of exerting a cytotoxic effect on *Klebsiella* is employed, these concentrations relate to the total concentration of all such klebicins.

The aqueous solution may, apart from the one or more protein(s) of the invention, contain a buffer. The buffer may be an inorganic or organic acid or salts thereof. An example of an inorganic acid is phosphoric acid or salts thereof. Examples of the organic acid are HEPES, acetic acid, succinic acid, tartaric acid, malic acid, benzoic acid, cinnamic acid, glycolic acid, lactic acid, citric acid, and ascorbic acid. Preferred organic acids are malic acid, lactic acid, citric acid, and ascorbic acid. The pH of the solution may generally be from 4 to 8, preferably from 5 to 8, more preferably from 6.0 to 7.5. If the object to which the composition is applied to is meat, the pH of the solution may generally be from 4 to 8, preferably from 4.5 to 7, more preferably from 5.0 to 6.5, and even more preferably from 5.0 to 6.0. Further, the solution may contain isotonic agents such as glycerol or a salt. A preferred salt to be used is sodium chloride. The aqueous solution containing the one or more klebicin(s) may be a buffered aqueous solution that may contain further solutes e.g. salts such as from 50 to 400 mM NaCl, preferably from 100 to 200 mM NaCl. The aqueous solution may further contain a sulfhydryl compound such as dithiothreitol (DTT), dithioerythritol, thioethanol or glutathione, preferably DTT. The concentration of the total of sulfhydryl compounds in the aqueous solution may be from 1 to 50 mM, preferably from 2 to 20 mM and more preferably from 4 to 10 mM.

If the composition of the invention is a solid composition, it may be a powder such as a lyophilized solid composition obtained by lyophilization of the extract or solution mentioned above. The powder may contain additional solid components such as those mentioned above for the aqueous solution. Before use, it may be reconstituted with a suitable liquid, such as water or buffer. The solid composition may contain buffer, salts or other components as mentioned above, such that the concentrations given above may be achieved upon reconstitution or dissolution of the solid composition.

Examples of carriers of the composition are solvents such as water or an aqueous buffer (as described above), salts, sugars such as monosaccharides and disaccharides, sugar alcohols, and other carriers such as those known from pharmaceutical compositions. Examples of the latter are starch, cellulose and other proteins such as albumin. Examples of sugars are glucose, fructose, lactose, sucrose, and maltose.

The composition of the invention may contain at least 10, preferably at least 20, more preferably at least 30, even more preferably at least 50, even more preferably at least 75% by weight of one or more klebicin(s) of the invention based on the total weight of protein in the composition. The content of klebicin(s) in the composition may be determined by subjecting the composition to SDS-PAGE and analyzing the obtained gel, after staining, by determining the intensity of bands on the gel, according to Reference Example 1. Thereby, intensity of bands due to klebicins can be determined in relation to the sum of intensities of bands due to all proteins in the composition.

In one embodiment, the composition of the invention is a pharmaceutical composition. The pharmaceutical composition may, apart from one or more proteins of the invention, optionally contain an *E. coli* colicin. It also contains one or more suitable pharmaceutically acceptable carrier and/or excipients, depending on whether it is liquid or solid and depending on the intended use. The excipients or carrier may be those mentioned above.

The composition of the invention such as the pharmaceutical composition may be formulated for oral delivery to the small or large intestine. Thus, the invention also provides an oral formulation comprising the protein of the invention or the composition according to the invention said formulation being capable of protecting the protein from gastric conditions (e.g. acidic pH and/or proteases) and capable of releasing the protein in the intestine. The capability of protecting the protein from gastric conditions and of releasing the protein in the intestine preferably relates to that in a mammal, preferably in a human subject. Enteric delivery of drugs or their active ingredients for avoiding the degradation of the drug or active ingredient by the acidic gastric conditions or gastric proteolytic conditions is known to the skilled person. Solid compositions or formulations such as tablets may be coated with a polymer that is resistant to gastric conditions but dissolves under the more neutral conditions of the intestine. Examples of commercial products suitable for coating are Eudragit™ S100 from Evonik or enTRinsic™ drug-delivery technology from Lonza Company.

In another embodiment, the composition of the invention such as the pharmaceutical composition may be formulated for delivery to the lungs. Thus, the invention also provides a pulmonary formulation comprising the protein of the invention or the composition according to the invention. For an overview over topical lung delivery of protein therapeutics see e.g. Bodier-Montagutelli et al., EXPERT OPINION ON DRUG DELIVERY 2018, VOL. 15, NO. 8, 729-736;

doi.org/10.1080/17425247.2018.1503251. The formulation may be a dry powder for aerosolization or a liquid solution for nebulization.

Other possible embodiments of formulations of the composition are given below in the section on medical applications.

Application to Objects

The invention provides a method of preventing or reducing contamination of an object with *Klebsiella*, comprising contacting said object with one or more proteins (klebicins) as described above or a composition as described above. The object is a non-living object. The object may be a surface of any non-organic object or an organic object such as food. Contamination of an object with *Klebsiella* means adhesion of viable *Klebsiella* cells to the object. Reducing contamination with *Klebsiella* means reducing the number of viable *Klebsiella* cells adhering to the object. Determining contamination of objects with *Klebsiella* is part of the general knowledge. For example, dilution plating of solutions or dispersions of homogenized food as done in the Examples or dilution plating of a rinsing solution of other objects may be used, followed by counting bacterial colonies. Preferably, the object is food or animal feed.

For treating or contacting the object with the protein or composition of the invention, a solution of the protein or a liquid composition as described above is generally contacted with the object. For example, said object is sprayed with an aqueous solution or is immersed into the aqueous solution as a composition of the invention. The object may be immersed for at least 10 seconds, preferably for at least 1 minute, preferably for at least 5 minutes into the aqueous solution. Contacting the object with a liquid composition helps to distribute the composition over the surface of the object. Where sufficiently even distribution can be achieved, it is possible to contact the object with a solid composition according to the invention.

Medical Applications

The invention also provides the protein, composition or pharmaceutical composition of the invention for use in the treatment or prevention of an infection of a subject with *Klebsiella*, notably the *Klebsiella* species mentioned above. The invention also provides a method of treating or preventing infection of a subject with *Klebsiella*, notably the *Klebsiella* species mentioned above, comprising administering to said subject one or more proteins (klebicin(s)) or the composition of the invention. The subject may be a human being or a mammal such as a farm animal. Human subjects are preferred. The infection to be treated may be an infection by *Klebsiella* that is antibiotic-resistant. The resistance may be carbapenem-resistance or a multidrug resistance.

The *Klebsiella* infection to be treated may be any of the *Klebsiella* species described above. Klebicins KpneM (SEQ ID NO:1) and KvarM (SEQ ID NO:2) and proteins defined herein using SEQ ID NO:1 or SEQ ID NO:2 as a reference sequence are preferred proteins for the medical applications due to their wide activity against many different isolates of *Klebsiella* as demonstrated in the Examples below. Therefore, these klebicins are preferably used for treating infection (as well as for preventing or reducing contamination, see above) with any *Klebsiella*, notably of *Klebsiella pneumoniae*.

The infection by *Klebsiella* to be treated may, for example, be an infection of the urinary tract, lower respiratory tract, biliary tract, surgical wounds, or syndromes (clinical syndromes) including pneumonia, bacteremia, thrombophlebitis, cholecystitis, diarrhea, upper respiratory tract infection, osteomyelitis, and meningitis, preferably pneumonia, bacteremia, thrombophlebitis, urinary tract infection (UTI), diarrhea, upper respiratory tract infection, and wound infection.

Generally, a liquid or solid pharmaceutical composition containing the klebicin(s) and optionally further components as described above is prepared for administration to the subject. Liquid compositions may be aqueous solutions as described above. Solid compositions may be powder containing at least one klebicin, e.g. in freeze-dried form, or tablets obtained from such powder or capsules filled with such powder.

The route of administration of the protein or pharmaceutical composition depends on the disease to be treated. For the treatment of diarrhea and upper respiratory tract infections, administration may be oral, e.g. in the form of a tablet or a solution. For the treatment of diarrhea, the pharmaceutical preparation may be one that allows passage through the stomach without being attacked by the acid medium in the stomach. The klebicin(s) should then be released from the pharmaceutical composition in the intestine. Such pharmaceutical preparations are known in the art. Examples are tablets and capsules resistant to the acid medium in the stomach. It is further possible to administer orally a biological material such as *E. coli* or plant material containing expressed klebicin(s) to a patient.

For the treatment of pneumonia, e.g. if the subject has a lung infection with *Klebsiella pneumoniae*, the pharmaceutical preparation may be administered to a subject as an aerosol or powder to the lungs. Methods for formulating a protein for administration to the lungs are known in the art, see e.g. inhaled recombinant DNAseI, or Dornase: Witt D M, Anderson L. Dornase alfa: a new option in the management of cystic fibrosis. Pharmacotherapy. 1996 January-February; 16 (1): 40-8; US20150024050A1: Dry powder formulations of Dnase I). Also see for review Depreter et al. 2013; Bodier-Montagutelli et al. 2018.

For the treatment of wound infection, the protein or pharmaceutical composition may be topically administered, e. g. as an aqueous solution. For urinary tract infection (UTI), the protein or pharmaceutical composition may be administered in the form of an aqueous solution using a catheter. For the treatment of cholecystitis or bile duct infection by *Klebsiella*, the protein or pharmaceutical composition may be administered in the form of an aqueous solution using a catheter.

The klebicin(s) may be administered to a human adult in amounts of 1 mg to 1000 mg per day, preferably of from 10 mg to 250 mg per day to a human patient. Such amounts may also be administered to an animal. In a probiotic approach, a patient may be treated by administering to the patient a genetically-modified microorganism expressing at least one of the klebicin(s). The genetically-modified microorganism may be a genetically-modified non-pathogenic *E. coli* or a lactic acid-producing microorganism as commonly employed in fermentation of milk products. Examples of lactic acid-producing microorganism are bacteria from the genera *Lactobacillus* such as *Lactobacillus lactis* and *Bifidobacterium* such as *Bifidobacterium bifidum* or *Bifidobacterium breve*. Another route of administration is by injection into the blood stream of a patient for preventing infection with *Klebsiella*. For this purpose, the klebicin(s) may be dissolved in a physiological saline and the solution be sterilized.

Production of Proteins of the Invention

A klebicin or protein according to the invention may be produced by known methods of protein expression in a standard expression system. For producing the klebicin, a nucleotide sequence encoding it may be expressed in a suitable host organism. Methods usable for producing and purifying a protein of interest have been described in the prior art and any such methods may be used. An *E. coli* expression system as generally known in the art may, for example, be used. If a eukaryotic expression system is used, one or more introns may be inserted in the coding sequence of the klebicin to prevent toxicity on the bacterial organism used for cloning.

Particularly efficient expression methods are plant expression systems that are also known in the prior art. Plant expression systems usable for expressing a klebicin according to the invention are described in the Examples. A possible way of achieving expression of a nucleotide sequence of interest in plants is the use of self-replicating (viral) replicons containing the nucleotide sequence encoding the klebicin. The coding sequence of the klebicin may be codon optimized for expression in plants or in the particular plant used as expression host. Plant viral expression systems have been described in many publications, such as in WO2012019660, WO2008028661, WO2006003018, WO2005071090, WO2005049839, WO2006012906, WO02101006, WO2007137788 or WO02068664 and many more publications are cited in these documents. Various methods for introducing a nucleic acid molecule, such as a DNA molecule, into a plant or plant part e.g. for transient expression are known. Agrobacteria may be used for transfecting plants with the nucleic acid molecule (vector) or nucleic acid construct e.g. by agroinfiltration or spraying with agrobacterial suspensions. For references, see WO 2012019660, WO 2014187571, or WO 2013149726. The nucleic acid molecule contains a nucleotide sequence encoding a protein of the invention.

In embodiments, wherein strong expression of a klebicin as a protein of interest is desired, a nucleic acid molecule or nucleic acid construct containing a nucleotide sequence encoding the klebicin may encode a viral vector that can replicate in plant cells to form replicons of the viral vector. To replicate, the viral vector and the replicons may contain an origin of replication that can be recognized by a nucleic acid polymerase present in plant cells, such as by the viral polymerase expressed from the replicon. In case of RNA viral vectors (referred to as "RNA replicons"), the replicons may be formed by transcription under the control of a promoter active in plant cells, from the DNA construct after the latter has been introduced into plant cell nuclei. In case of DNA replicons, the replicons may be formed by recombination between two recombination sites flanking the sequence encoding the viral replicon in the DNA construct, e.g. as described in WO00/17365 and WO 99/22003. If the replicon is encoded by the DNA construct, RNA replicons are preferred. Use of DNA and RNA viral vectors (DNA or RNA replicons) has been extensively described in the literature over the years. Some examples are the following patent publications: WO2008028661, WO2007137788, WO 2006003018, WO2005071090, WO2005049839, WO02097080, WO02088369, WO02068664. Examples of DNA viral vectors are those based on geminiviruses. For the present invention, viral vectors or replicons based on plant RNA viruses, notably those based on plus-sense single-stranded RNA viruses may be preferably used. Accordingly, the viral replicon may be a plus-sense single-stranded RNA replicon. Examples of such viral vectors are those based on tobacco mosaic virus (TMV) and potexvirus X (PVX). "Based on" means that the viral vector uses the replication system such as the replicase and/or other proteins involved in replication of these viruses. Potexvirus-based viral vectors and expression systems are described in EP2061890 or WO2008/028661. As is known from the references cited, RNA replicons such as plus-sense single-stranded RNA replicons may express a nucleotide sequence under the control of a subgenomic promoter located upstream of the nucleotide sequence. By the action of the viral replicase that may be encoded on the same RNA replicon, subgenomic RNA may be replicated in plant cells, containing the (RNA) nucleotide sequence, whereby the protein may be translated from the subgenomic RNA.

The klebicin may be expressed in a multi-cellular plant or a part thereof, notably a higher plant or parts thereof. Both monocot and dicot (crop) plants can be used. Common plants usable for expressing the protein of interest include *Nicotiana benthamiana, Nicotiana tabacum*, spinach, *Brassica campestris, B. juncea*, beets (*Beta vulgaris*), cress, arugula, mustard, strawberry, *Chenopodium capitatum*, lettuce, sunflower, cucumber, chinese cabbage, cabbage, carrot, green onion, onion, radish, lettuce, field peas, cauliflower, broccoli, burdock, turnip, tomato, eggplant, squash, watermelon, prince melon, and melon. Preferred plants are spinach, chard, beetroot, carrot, sugar beet, *Nicotiana tabacum*, and *Nicotiana benthamiana*. Expression in edible plants may be used for preventing contamination of the plants or food made therefrom with *Klebsiella*. In one embodiment, plants are used that do not normally enter the human or animal food chain such as *Nicotiana* species such as *N. tabacum* and *N. benthamiana*.

Generally, the klebicin as a protein of interest is expressed in the cytosol of cells of the plants or plant parts. In this case, no signal peptide directing the protein of interest into a particular compartment is added to the protein. Alternatively, the protein of interest can be expressed in or targeted into chloroplasts of the plants; in the latter case, an N-terminal pre-sequence, generally referred to as plastid transit peptide or chloroplast targeting peptide, is added to the N-terminal or C-terminal end, preferably the N-terminal end, of the klebicin as the protein of interest.

The invention provides a nucleic acid molecule containing a nucleotide sequence encoding a protein of the invention. The nucleic acid molecule may comprise a nucleic acid construct that contains (i) a transcription promoter active in plant cells and (ii) a nucleotide sequence encoding a protein of the invention for expressing said nucleotide sequence in plant cells under the control of the promoter.

The invention also provides a nucleic acid molecule or nucleic acid construct encoding the protein of the invention, said nucleic acid molecule or nucleic acid construct comprising (i) a transcription promoter that is preferably active in plant cells and (ii) a nucleotide sequence encoding said protein for expressing said nucleotide sequence in cells, preferably in plant cells, under the control of said promoter.

Further, the invention provides a nucleic acid molecule or nucleic acid construct encoding a protein of the invention, said nucleic acid molecule or nucleic acid construct is or encodes a viral (DNA or RNA) replicon comprising a nucleotide sequence encoding said protein for expressing said nucleotide sequence in cells, preferably in plant cells; said replicon may contain a subgenomic promoter for expressing said nucleotide sequence in plant cells or cells of a plant under the control of said subgenomic promoter.

As the protein of the invention is preferably expressed in a plant or in plant cells, the invention also provides a plant, plant tissue, or plant cell, comprising a protein of the invention. The invention also provides a plant, plant tissue, or plant cell, comprising the nucleotide sequence or the nucleic acid molecule of the invention. The plant may be any one of those mentioned above.

Production of the Composition of the Invention

In the process of producing a composition comprising at least one klebicin, a klebicin is, in the first step, expressed in a plant or cells of a plant, such as an edible plant. In the next step, plant material containing expressed klebicin from a plant having expressed the klebicin is harvested. Plant material may e.g. be leaves, roots, tubers, or seeds, or a crushed, milled or comminuted product of leaves, roots, tubers, or seeds. In step (iii), the klebicin is extracted from the plant material using an aqueous buffer. This may include that the plant material is homogenized, and insoluble material may be removed by centrifugation or filtration. Soluble components including the klebicin will be extracted into the aqueous buffer to produce a klebicin solution in the aqueous buffer. The aqueous buffer may contain an inorganic or organic acid or salts thereof and may have a pH as defined above for the aqueous solution as a composition of the invention. Further, the aqueous buffer may contain salt and/or a sulfhydryl compound as also described above for the aqueous solution as a composition of the invention. If a relatively pure klebicin composition is desired, the klebicin solution in the aqueous buffer may be further purified by removing undesired components according to known methods of protein purification.

Accordingly, the invention provides a process of producing a composition comprising a protein according to the invention, said process comprising the following steps:

(i) expressing said protein in a plant as described above, preferably an edible plant or *Nicotiana,*

(ii) harvesting plant material containing expressed protein from said plant, (iii) extracting said protein from said plant material using an aqueous buffer to obtain a composition containing said protein, optionally removing undesired contaminants from said composition.

If a klebicin is expressed in plants, the plants or tissue thereof having expressed protein is harvested, the tissue may be homogenized, and insoluble material may be removed by centrifugation or filtration. If relatively pure klebicin is desired, the klebicin may be further purified by generally known method of protein purification such as by chromatographic methods which can remove other host-cell proteins and plant metabolites such as alkaloids and polyphenols. Purified klebicin solutions may be concentrated and/or freeze-dried.

If klebicin are expressed in edible plants, crude protein extracts from the edible plants or semi-purified concentrates may be used for preventing or reducing contamination of an object such as food with *Klebsiella.*

EXAMPLES

Reference Example 1

Soft-Agar Overlay Assay for Evaluation of Klebicin Toxicity

Overnight *Klebsiella quasipneumoniae* subsp. *similipneumoniae* SB30 (DSM 28212) culture is equalized to OD595=1.0 in LB medium and diluted 100× in 0.8% top agar preheated in a 55° C. water bath. Mixed overlay components are poured on plates containing solid agar (1.5% LB agar); the plates are kept for a few minutes allowing the agar to harden. Sterile Whatman discs (6 mm diameter) are placed on soft-agar and 20 µl aliquots of klebicin solution containing 10 µg klebicin protein are applied to the disks. The plates are incubated for 16 hours at 37° C. After 16 hours incubation, the diameter of klebicin inhibition zones is measured.

Determination of Klebicin Concentration

The klebicin concentration in liquid sample containing the klebicin is determined by performing SDS-PAGE with Coomassie staining and reading out the intensity of the band due to the klebicin using a commercial reader and by comparing the determined intensity with bands obtained by performing SDS-PAGE with Coomassie staining of serial dilutions of Bovine Serum Albumin (BSA) of known concentrations. A calibration curve may be obtained from the intensities of bands on stained SDS-PAGE gels of BSA. The concentration of BSA is determined using the Bradford protein assay (For example, Bradford reagent, B6916, Sigma-Aldrich, St-Louis, MO, USA).

Example 1: Construction of Klebicin Expression Vectors

Figure 1:
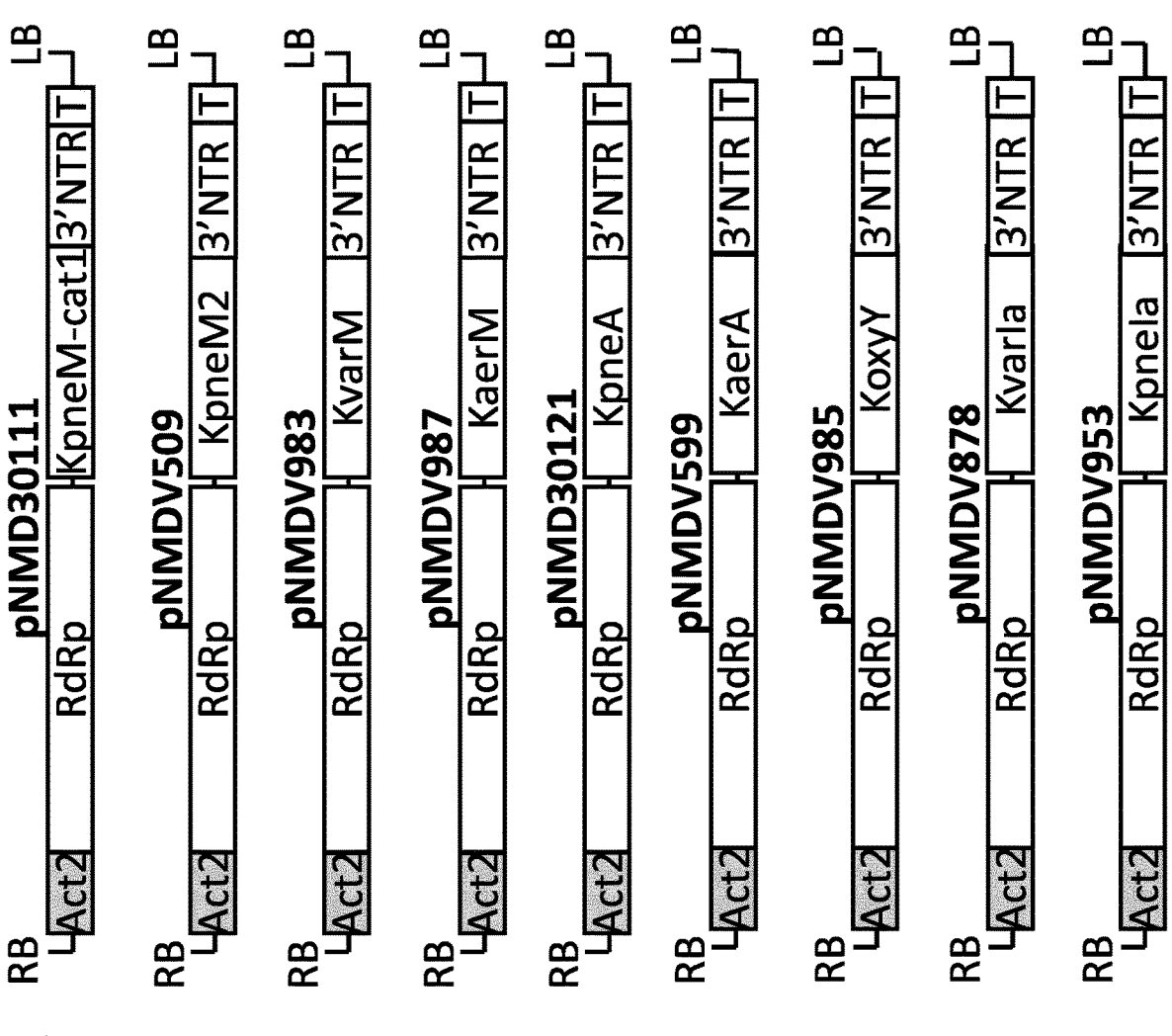
FIG. 1 shows schematically T-DNA regions of TMV-based vectors for the expression of klebicins. RB: right T-DNA border, Act2: *Arabidopsis thaliana* actin promoter; RdRp: RNA-dependent RNA polymerase; 3'NTR: 3' non-translated region; T: nos terminator; LB: left T-DNA border. KpneM-cat1: coding sequence of the klebicin KpneM (*K. pneumoniae* EWD35590.1) with the first intron of catalase gene (cat-1) from *Ricinus communis*; KpneM2: coding sequence of the klebicin KpneM2 (*Klebsiella* sp. WP_047066220); KvarM: coding sequence of the klebicin KvarM (*K. variicola* CTQ17225.1); KaerM: coding sequence of the klebicin KaerM (*K. aerogenes* WP_015367360.1); KpneA: coding sequence of the klebicin KpneA (*K. pneumoniae* SAV78255.1); KaerA: coding sequence of the klebicin KaerA (*K. aerogenes* WP_063414841.1); KoxyY: coding sequence of the klebicin KoxyY (*K. oxytoca* WP_024273778); Kvarla: coding sequence of the klebicin Kvarla (*K. variicola* KDL88409); Kpnela: coding sequence of the klebicin Kpnela (*K. pneumoniae* BAS34675).

The KpneA (*K. pneumoniae* SAV78255.1), KaerA (*K. aerogenes* WP_063414841.1), KoxyY (*K. oxytoca* WP_024273778), Kvarla (*K. variicola* KDL88409), Kpnela (*K. pneumoniae* BAS34675), KpneM (*K. pneumoniae* EWD35590.1), KpneM2 (*Klebsiella* sp. WP_047066220), KvarM (*K. variicola* CTQ17225.1), KaerM (*K. aerogenes* WP_015367360.1) optimized for expression in the host plant *Nicotiana benthamiana* were synthetized by Thermofisher Scientific (USA) and inserted as BsaI-BsaI fragments in pICH29912, assembled TMV-based magnICON® vector (Marillonnet et al., 2005) (FIG. 1). Obtained plasmids were used to transform *A. tumefaciens* GV3101.

Example 2: Expression of Klebicins in Plants

*N. benthamiana* plants were grown in a growth chamber at 25° C. and 50% humidity, with a 16 h light (1500 lux) and 8 h dark photoperiod. Four-to-six-week-old plants were used for transfection with recombinant *A. tumefaciens*.

*A. tumefaciens* were grown overnight at 30° C. in LB medium containing 50 mg L$^{-1}$ rifampicin and 50 mg L$^{-1}$ kanamycin. *Agrobacterium* overnight cultures were sedimented at 3220 g for 5 min and resuspended in tap water at an $OD_{595}$ of 1.5.

Four-to-six-week-old plant leaves were infiltrated into the abaxial side of the leaf using a syringe without a needle with a 1:1000 dilution of *A. tumefaciens* strain containing expression vector. Plant leaves were observed and collected at 4-7 dpi (days post infiltration).

Figure 2:
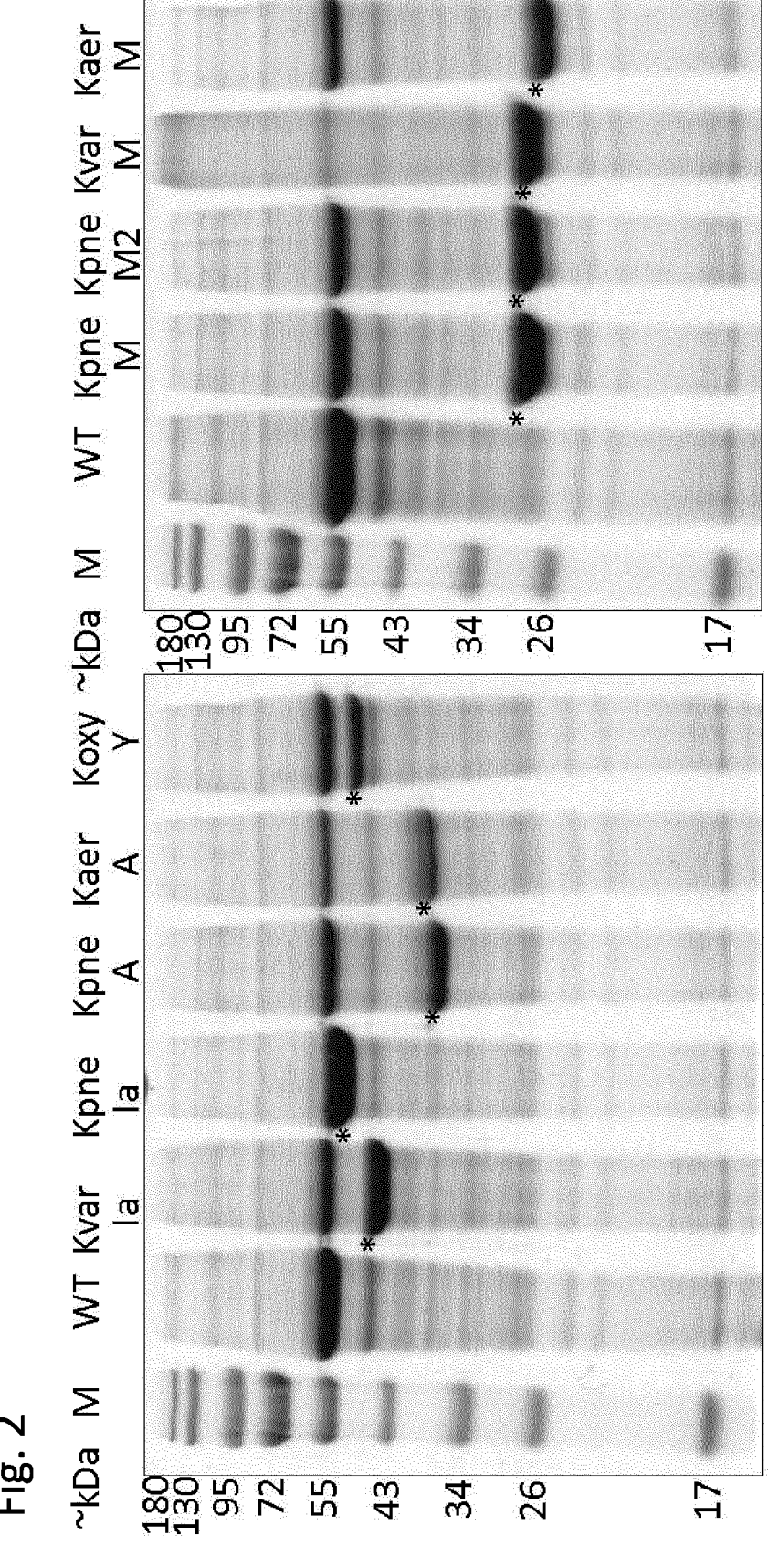
FIG. 2 shows SDS-PAGE analysis of the expression of klebicins in *N. benthamiana* leaves. Plant material (50 mg) was harvested at 5 or 7 days post spraying (dps) (pooled samples of three leaves-klebicin KaerA at 4 dps, all remaining klebicins at 5 dps), ground in liquid nitrogen, extracted with 50 mM Tris-HCl, 300 mM NaCl 15 mM sodium acetate, 3 mM DTT (pH 7.5), and denatured at 98° C. for 10 min. Solutions containing 5 µg of protein were resolved in 12% polyacrylamide gel for Coomassie staining. M—PageRuler Prestained protein ladder (ThermoFisher Scientific Baltics), WT—crude extract of non-sprayed *N. benthamiana* leaves, Kvarla, Kpnela, KpneA, KaerA, KoxyY, KpneM, KpneM2, KvarA, KaerM-extracts of *N. benthamiana* leaves, sprayed with klebicin expression constructs. Bands corresponding to recombinant klebicins are marked by asterisks.

The SDS-PAGE and Coomassie staining analysis of the extracts of soluble proteins of infiltrated plant leaves revealed that all nine klebicins are efficiently expressed in plants and are detected in the gel as very intense supplementary bands (FIG. 2). The weights of polypeptides observed in electrophoresis approximately correspond to the expected theoretical molecular weights (Kvarla—43.4 kDa, Kpnela—48.5 kDa, KpneA—40 kDa, Kaer A—39 kDa, KoxyY—48.7 kDa, KpneM—30.3 kDa, KpneM2—29.7 kDa, KvarM—29.8 kDa and KaerM—29 kDa). The expression level of individual klebicins varies in a range of 2.7-4.4 mg/g FW, the highest expression levels achieved by the two *K. pneumoniae* M-type klebicins KpneM2 and KpneM (Table 1).

Example 3: Purification of Klebicins from Plant Biomass

KpneA, KaerA, Kvarla, KpneM, KpneM2 and KvarM bacteriocins were purified to homogeneity by protein chromatography. Quite pure KpneM, KpneM2 and KvarM proteins were obtained after single step hydrophobic interaction chromatography (HIC), but for best results a second purification step by anion chromatography was included. KpneA and Kvarla were also purified by using as a first step hydrophobic interaction chromatography, but then followed by cation exchange chromatography column. KaerA was purified by two steps of ion exchange chromatography, cation exchange column as a first step and anion exchange column as second step.

Crude protein extract was prepared as follows. A small portion of frozen leaf tissue was ground into fine powder with mortar and pestle using liquid nitrogen. Prepared powder was mixed with cold extraction buffer at a ratio of 1 g of plant material to 5 mL of buffer. The suspension was kept on ice for 15-20 min. Cell debris were removed by centrifugation at 3220 g at 4° C. for 20 min., and the supernatant was filtered through membrane filters (pore sizes 5 µm and 0.22 µm). Obtained solution was taken as total soluble protein and applied for purification by two-step chromatography. Details of purification protocols varied depending on proteins.

Figure 3B:
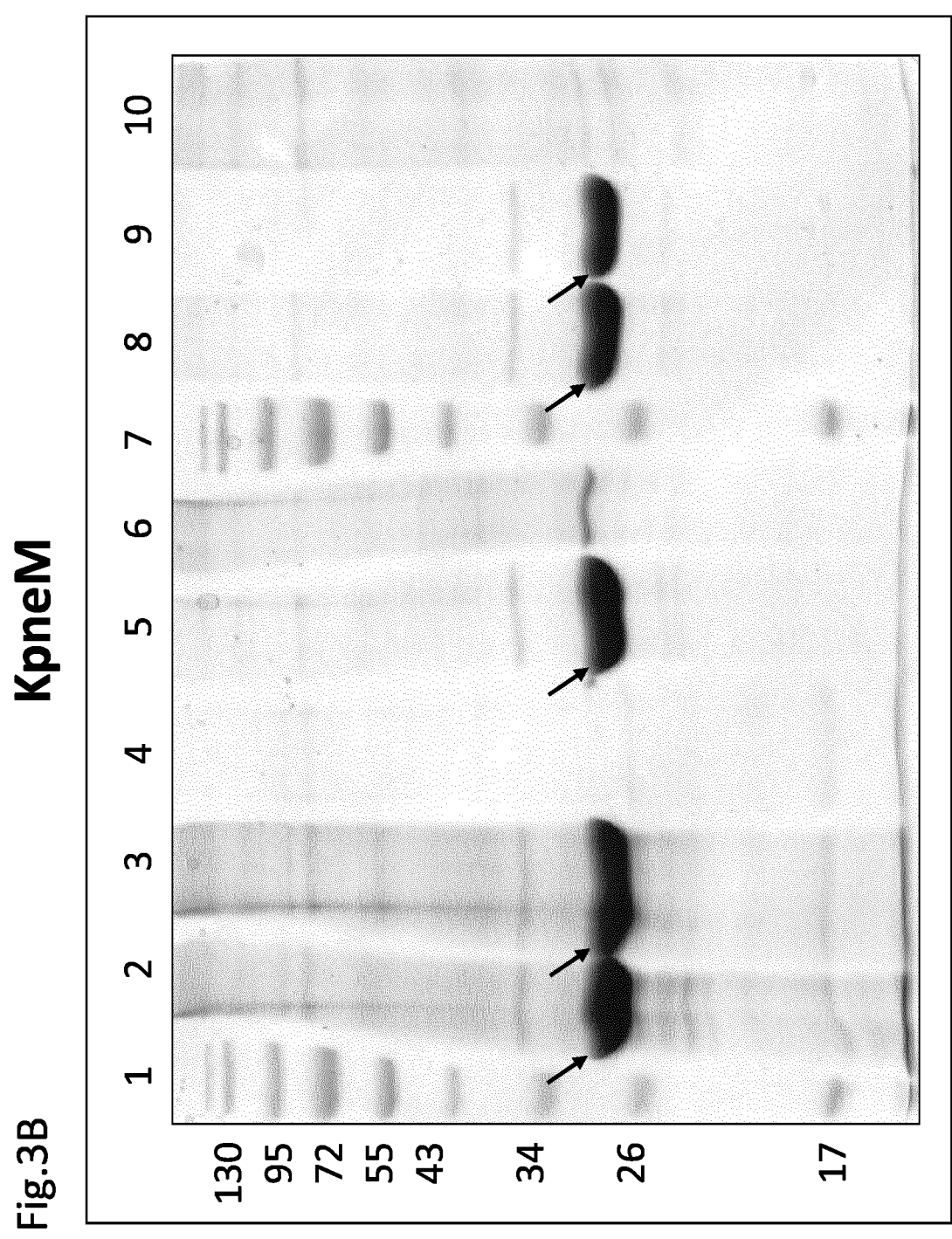
Figure 3D:
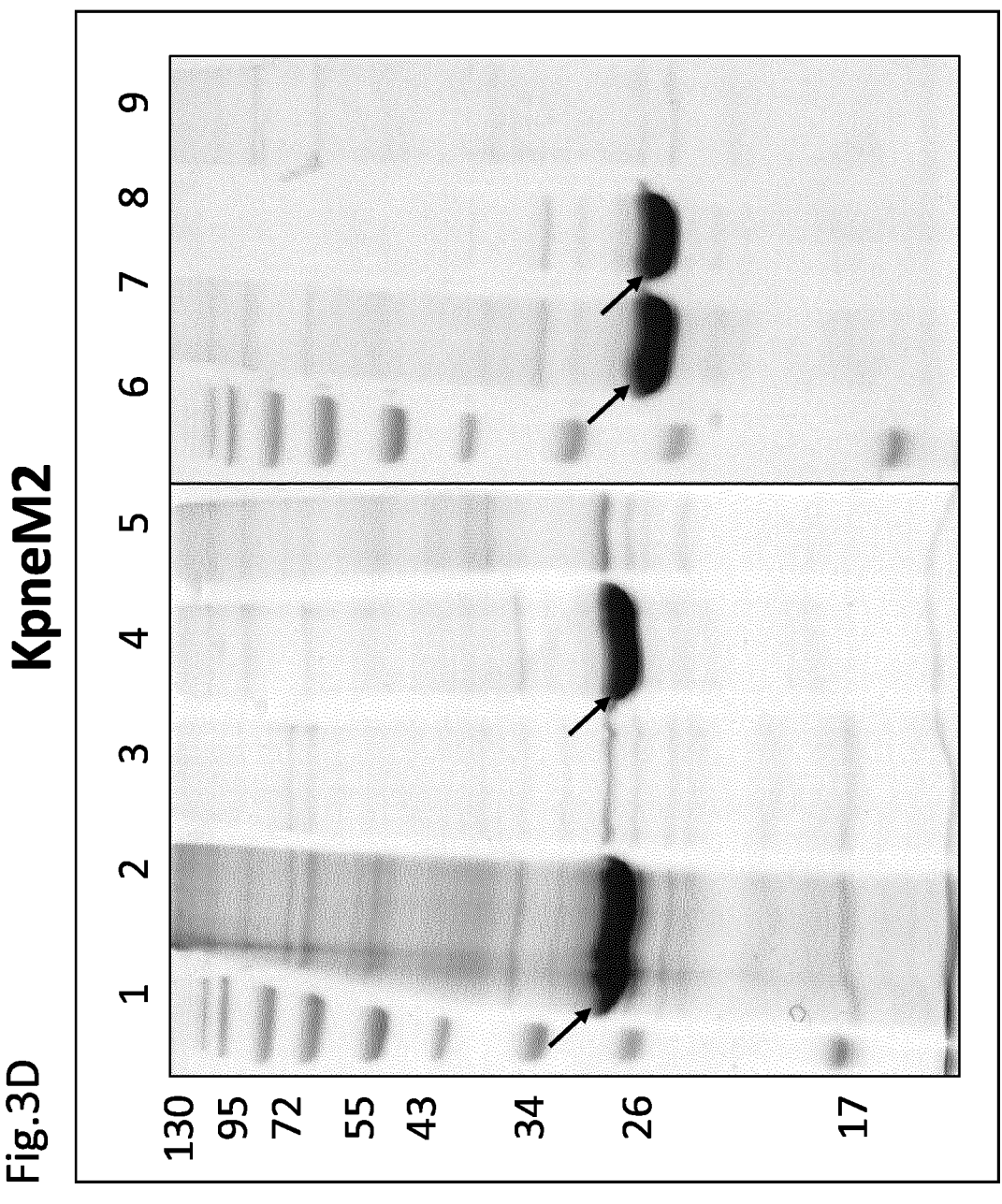
Figure 3F:
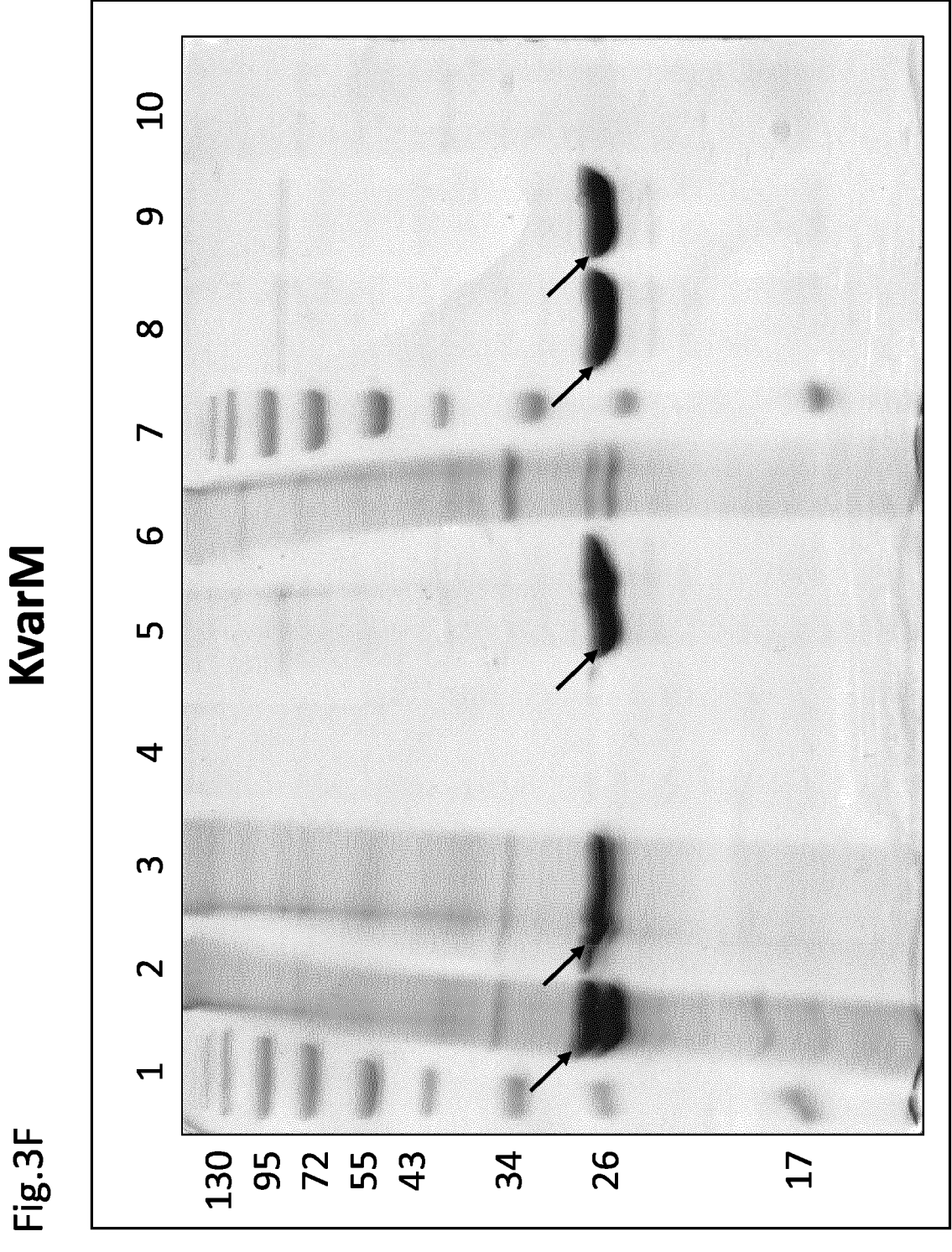
Figure 3H:
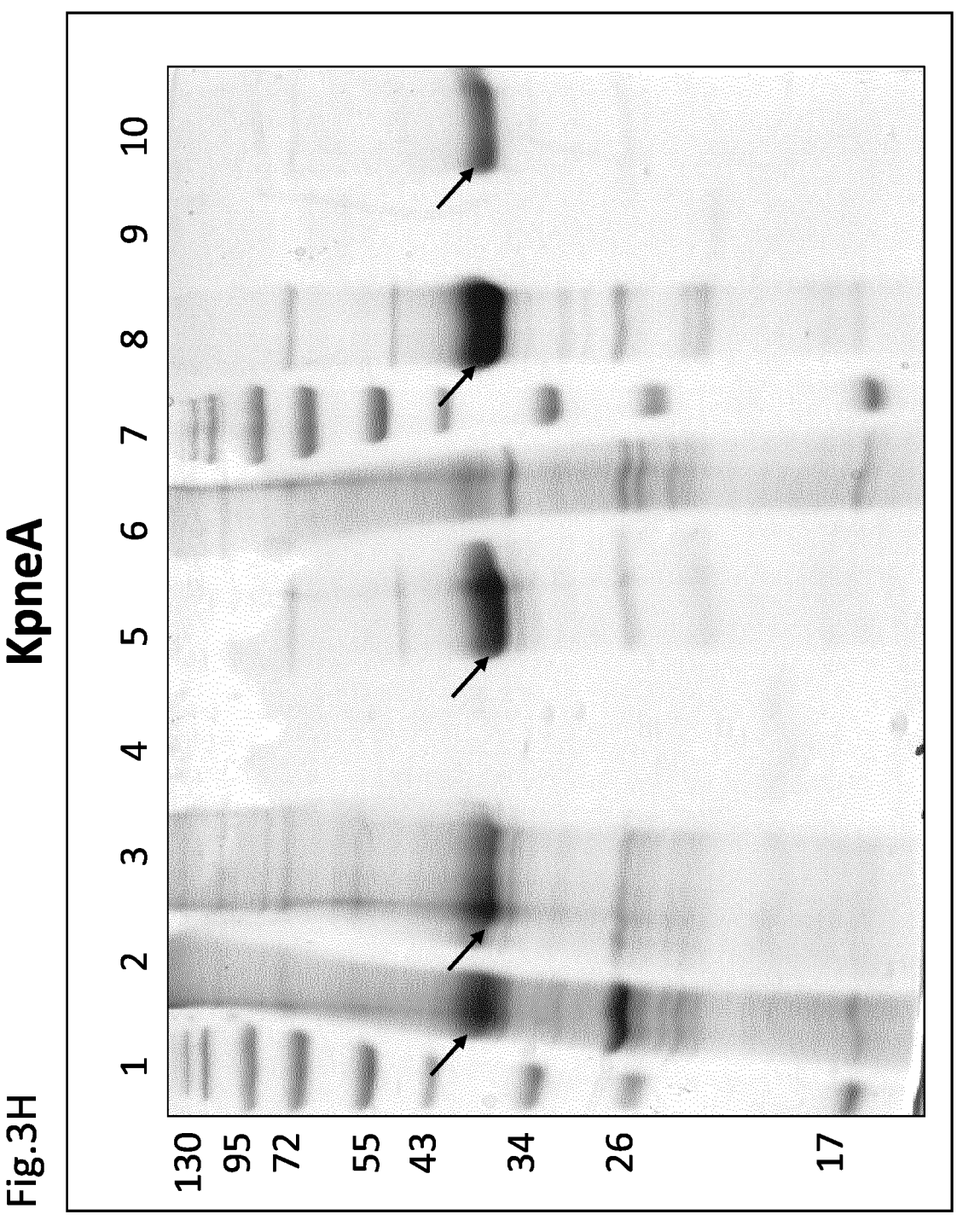
Figure 3J:
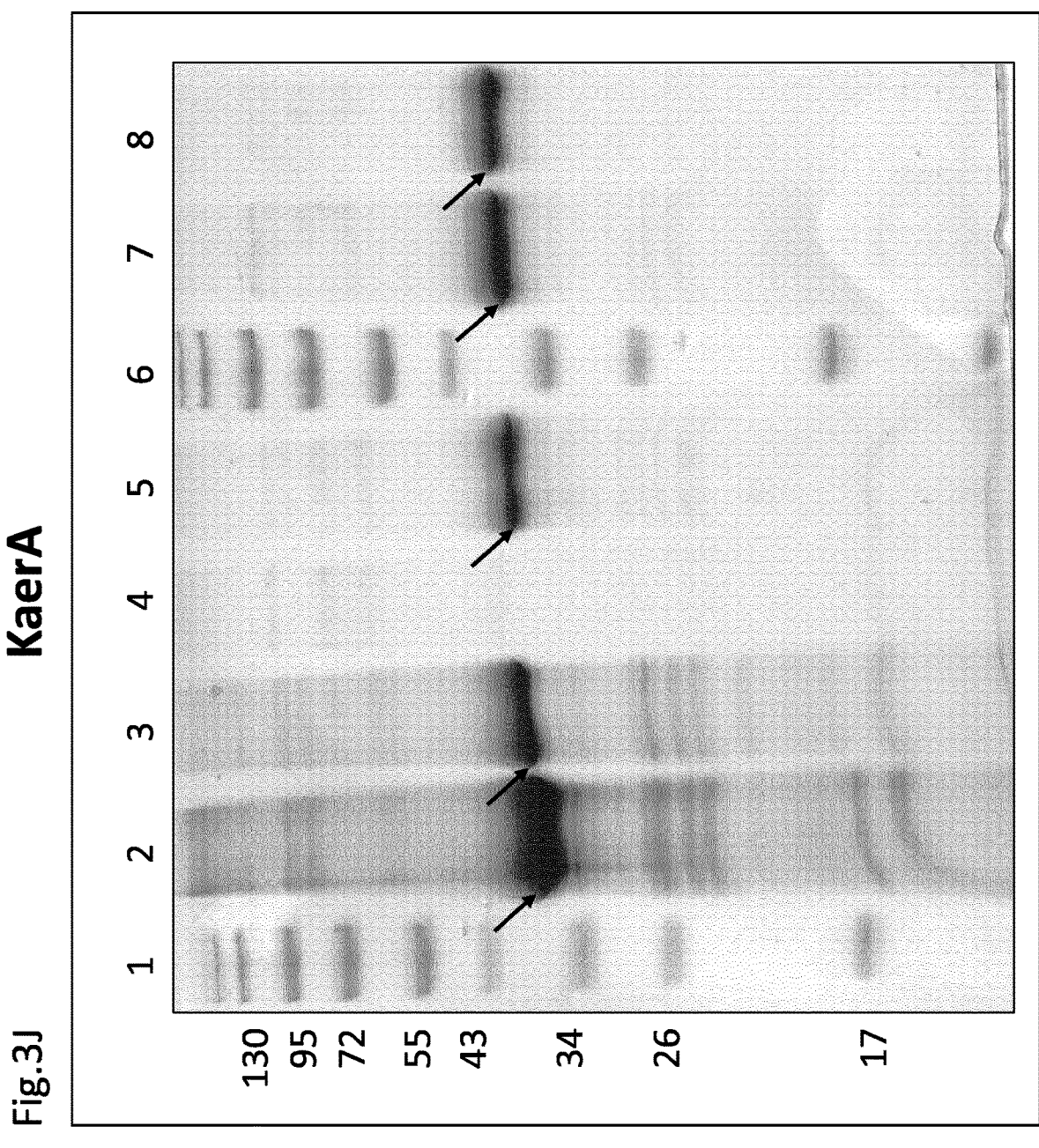
Figure 3L:
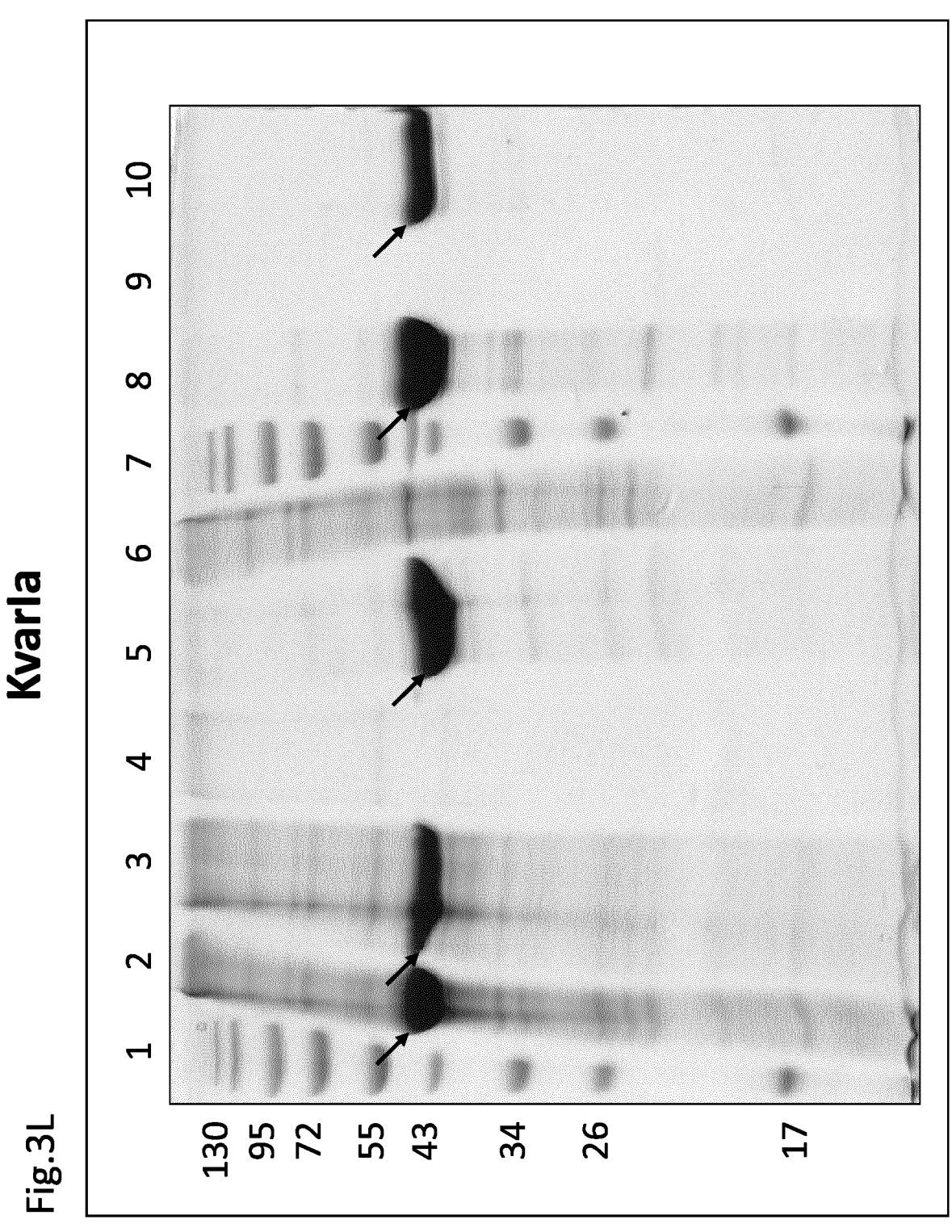

KpneM was purified using the combination of Hydrophobic Interaction Chromatography (HIC) and Anion Exchange Chromatography (AEXC) (FIG. 3A, B).

A small portion of frozen leaf tissue was homogenized with chilled mortar and pestle in liquid nitrogen. Prepared powder was mixed with cold extraction buffer (50 mM $NaH_2PO_4/Na_2HPO_4$, 30 mM NaCl, pH 5.0) at a ratio of 1 g of plant material to 5 ml of buffer. The crude extract kept at 20-25° C. for 10-15 min. Cell debris were removed by centrifugation at 3220 g, at 4° C. for 20 min. Pellets were discarded and the supernatant was filtered by passing solution through membrane filters (pore sizes 5 µm and 0.45 µm). Ammonium sulphate was added up to 0.70 M and pH of solution adjusted to 6. Formed precipitate was removed by centrifugation at 3220 g, at 4° C. for 5 min. The supernatant was taken as total soluble protein and applied for purification in two steps.

At the first purification step the chromatography column was filled with Phenyl sepharose FF resin (GE Healthcare Life Sciences, Uppsala, Sweden) and pre-equilibrated with cold buffer (50 mM $NaH_2PO_4/Na_2HPO_4$, 0.70 M $(NH_4)_2SO_4$, pH 6.0). Protein solution was loaded to column and the Phenyl sepharose bounded protein fraction was eluted by washing with elution buffer (50 mM $NaH_2PO_4/Na_2HPO_4$, 0.28 M $(NH_4)_2SO_4$, pH 6.0). Collected protein fraction replaced to the diafiltrating concentrator (10 kDa) and centrifuged at 3220 g until the volume of protein solution decreased 8-10 folds. Concentrate was diluted up to a primary volume with buffer containing 50 mM $NaH_2PO_4/Na_2HPO_4$ (pH 8.0). Procedure was repeat till conductivity decreased below 10 mS/cm and protein solution subjected to the final purification step using Q sepharose FF resin (GE-Healthcare Life Sciences, Uppsala, Sweden). Chromatography media was pre-equilibrated with cold buffer (50 mM $NaH_2PO_4/Na_2HPO_4$, pH 8.0). Protein solution was loaded to column and Q sepharose unbounded protein was collected in flow through fraction. After KpneM was freeze-dried and applied for analysis.

KpneM2 was purified using the combination of Hydrophobic Interaction Chromatography (HIC) and Anion Exchange Chromatography (AEXC) (FIG. 3C, D).

A small portion of frozen leaf tissue was homogenized with chilled mortar and pestle in liquid nitrogen. Prepared powder was mixed with cold extraction buffer (50 mM $NaH_2PO_4/Na_2HPO_4$, 30 mM NaCl, pH 5.0) at a ratio of 1 g of plant material to 5 ml of buffer. The crude extract kept at 20-25° C. for 10-15 min. Cell debris were removed by centrifugation at 3220 g, at 4° C. for 20 min. Pellets were discarded and the supernatant was filtered by passing solution through membrane filters (pore sizes 5 μm and 0.45 μm). Ammonium sulphate was added up to 0.70 M and pH of solution adjusted to 6. Formed precipitate was removed by centrifugation at 3220 g, at 4° C. for 5 min. The supernatant was taken as total soluble protein and applied for purification in two steps.

At the first purification step the chromatography column was filled with Phenyl sepharose FF resin (GE Healthcare Life Sciences, Uppsala, Sweden) and pre-equilibrated with cold buffer (50 mM $NaH_2PO_4/Na_2HPO_4$, 0.70 M $(NH_4)_2SO_4$, pH 6.0). Protein solution was loaded to column and the Phenyl sepharose bounded protein fraction was eluted by washing with elution buffer (50 mM $NaH_2PO_4/Na_2HPO_4$, 0.42 M $(NH_4)_2SO_4$, pH 6.0). Collected protein fraction replaced to the diafiltrating concentrator (10 kDa) and centrifuged at 3220 g until the volume of protein solution decreased 8-10 folds. Concentrate was diluted up to a primary volume with buffer containing 50 mM $NaH_2PO_4/Na_2HPO_4$ (pH 8.0). Procedure was repeat till conductivity decreased below 10 mS/cm and protein solution subjected to the final purification step using Q sepharose FF resin (GE-Healthcare Life Sciences, Uppsala, Sweden). Chromatography media was pre-equilibrated with cold buffer (50 mM $NaH_2PO_4/Na_2HPO_4$, pH 8.0). Protein solution was loaded to column and Q sepharose unbounded protein was collected in flow through fraction. After KpneM2 was freeze-dried and applied for analysis.

KvarM was purified using the combination of Hydrophobic Interaction Chromatography (HIC) and Anion Exchange Chromatography (AEXC) (FIG. 3E, F).

A small portion of frozen leaf tissue was homogenized with chilled mortar and pestle in liquid nitrogen. Prepared powder was mixed with cold extraction buffer (50 mM $NaH_2PO_4/Na_2HPO_4$, pH 5.0) at a ratio of 1 g of plant material to 5 ml of buffer. The crude extract kept at 20-25° C. for 10-15 min. Cell debris were removed by centrifugation at 3220 g, at 4° C. for 20 min. Pellets were discarded and the supernatant was filtered by passing solution through membrane filters (pore sizes 5 μm and 0.45 μm). Ammonium sulphate was added up to 0.95 M and pH of solution adjusted to 6. Formed precipitate was removed by centrifugation at 3220 g, at 4° C. for 5 min. The supernatant was taken as total soluble protein and applied for purification in two steps.

At the first purification step the chromatography column was filled with Phenyl sepharose FF resin (GE Healthcare Life Sciences, Uppsala, Sweden) and pre-equilibrated with cold buffer (50 mM $NaH_2PO_4/Na_2HPO_4$, 0.95 M $(NH_4)_2SO_4$, pH 6.0). Protein solution was loaded to column and the Phenyl sepharose bounded protein fraction was eluted by washing with elution buffer (50 mM $NaH_2PO_4/Na_2HPO_4$, 0.62 M $(NH_4)_2SO_4$, pH 6.0). Collected protein fraction was placed in the diafiltrating concentrator (10 kDa) and centrifuged at 3220 g until the volume of protein solution decreased 8-10 folds. Concentrate was diluted up to a primary volume with buffer containing 50 mM $NaH_2PO_4/Na_2HPO_4$ (pH 8.0). Procedure was repeated until conductivity decreased below 10 mS/cm and protein solution was subjected to the final purification step using Q sepharose FF resin (GEHealthcare Life Sciences, Uppsala, Sweden). Chromatography media was pre-equilibrated with cold buffer (50 mM $NaH_2PO_4/Na_2HPO_4$, pH 8.0). Protein solution was loaded to column and Q sepharose unbounded protein was collected in flow through fraction. After that, KvarM was freeze-dried and applied for analysis.

KpneA was purified using the combination of Hydrophobic Interaction Chromatography (HIC) and Cation Exchange Chromatography (CEXC) (FIG. 3G, H).

A small portion of frozen leaf tissue was homogenized with chilled mortar and pestle in liquid nitrogen. Prepared powder was mixed with cold extraction buffer (20 mM $NaH_2PO_4/Na_2HPO_4$, 30 mM NaCl, pH 5.0) at a ratio of 1 g of plant material to 5 ml of buffer. The crude extract kept at 20-25° C. for 10-15 min. Cell debris were removed by centrifugation at 3220 g, at 4° C. for 20 min. Pellets were discarded and the supernatant was filtered by passing solution through membrane filters (pore sizes 5 μm and 0.45 μm). Ammonium sulphate was added up to 1.50 M and pH of solution adjusted to 6. Formed precipitate was removed by centrifugation at 3220 g, at 4° C. for 5 min. The supernatant was taken as total soluble protein and applied for purification in two steps.

At the first purification step the chromatography column was filled with Phenyl sepharose FF resin (GE Healthcare Life Sciences, Uppsala, Sweden) and pre-equilibrated with cold buffer (50 mM $NaH_2PO_4/Na_2HPO_4$, 1.50 M $(NH_4)_2SO_4$, pH 6.0). Protein solution was loaded to column and the Phenyl sepharose bounded protein fraction was eluted by washing with elution buffer (50 mM $NaH_2PO_4/Na_2HPO_4$, 0.90 M $(NH_4)_2SO_4$, pH 6.0). Collected protein fraction was placed in the diafiltrating concentrator (10 kDa) and centrifuged at 3220 g until the volume of protein solution decreased 8-10 folds. Concentrate was diluted up to a primary volume with buffer containing 20 mM $NaH_2PO_4/Na_2HPO_4$, 20 mM Sodium citrate (pH 4.5). Procedure was repeated till conductivity decreased below 9 mS/cm and protein solution was subjected to the final purification step using SP sepharose FF resin (GEHealthcare Life Sciences, Uppsala, Sweden). Chromatography media was pre-equilibrated with cold buffer (20 mM $NaH_2PO_4/Na_2HPO_4$, 20 mM Citric acid, pH 4.5). Protein solution was loaded to column and SP sepharose bounded protein fraction was eluted by linear gradient of cold washing buffer additionally containing 500 mM of NaCl. After that, KpneA was freeze-dried and applied for analysis.

KaerA was purified using the combination of Cation Exchange Chromatography (CEXC) and Anion Exchange Chromatography (AEXC) (FIG. 3I, J).

A small portion of frozen leaf tissue was homogenized with chilled mortar and pestle in liquid nitrogen. Prepared powder was mixed with cold extraction buffer (20 mM $NaH_2PO_4/Na_2HPO_4$, 20 mM Citric acid, pH 5.0) at a ratio of 1 g of plant material to 5 ml of buffer. The crude extract kept at 20-25° C. for 10-15 min. Cell debris were removed by centrifugation at 3220 g, at 4° C. for 20 min. Pellets were discarded and the supernatant was filtered by passing solution through membrane filters (pore sizes 5 μm and 0.45 μm). The pH of solution was adjusted to 4.5 and formed precipitate was removed by centrifugation at 3220 g, at 4° C. for 5 min. The supernatant was taken as total soluble protein and applied for purification in two steps.

At the first purification step the chromatography column was filled with SP sepharose FF resin (GE Healthcare Life Sciences, Uppsala, Sweden) and pre-equilibrated with cold buffer (20 mM $NaH_2PO_4/Na_2HPO_4$, 20 mM Citric acid, pH 4.5). Protein solution was loaded to column and SP sepharose bounded protein fraction was eluted by linear gradient of cold washing buffer additionally containing 500 mM of NaCl. Collected protein fraction was placed in the diafiltrating concentrator (10 kDa) and centrifuged at 3220 g until the volume of protein solution decreased 8-10 folds. Concentrate was diluted up to a primary volume with buffer containing 20 mM $NaH_2PO_4/Na_2HPO_4$, (pH 8.0). Procedure was repeated until conductivity decreased below 8 mS/cm and protein solution was subjected to the final purification step using Q sepharose FF resin (GEHealthcare Life Sciences, Uppsala, Sweden). Chromatography media was pre-equilibrated with cold buffer (20 mM $NaH_2PO_4/Na_2HPO_4$, pH 8.0). Protein solution was loaded to column and Q sepharose unbounded protein was collected in flow through fraction. After that, KaerA was freeze-dried and applied for analysis.

Kvarla was purified using the combination of Hydrophobic Interaction Chromatography (HIC) and Cation Exchange Chromatography (CEXC) (FIG. 3K, L).

A small portion of frozen leaf tissue was homogenized with chilled mortar and pestle in liquid nitrogen. Prepared powder was mixed with cold extraction buffer (20 mM $NaH_2PO_4/Na_2HPO_4$, 30 mM NaCl, pH 5.0) at a ratio of 1 g of plant material to 5 ml of buffer. The crude extract kept at 20-25° C. for 10-15 min. Cell debris were removed by centrifugation at 3220 g, at 4° C. for 20 min. Pellets were discarded and the supernatant was filtered by passing solution through membrane filters (pore sizes 5 μm and 0.45 μm). Ammonium sulphate was added up to 1.35 M and pH of solution adjusted to 6. Formed precipitate was removed by centrifugation at 3220 g, at 4° C. for 5 min. The supernatant was taken as total soluble protein and applied for purification in two steps.

At the first purification step the chromatography column was filled with Phenyl sepharose FF resin (GE Healthcare Life Sciences, Uppsala, Sweden) and pre-equilibrated with cold buffer (50 mM $NaH_2PO_4/Na_2HPO_4$, 1.35 M $(NH_4)_2SO_4$, pH 6.0). Protein solution was loaded to column and the Phenyl sepharose bounded protein fraction was eluted by washing with elution buffer (50 mM $NaH_2PO_4/Na_2HPO_4$, 0.81 M $(NH_4)_2SO_4$, pH 6.0). Collected protein fraction was placed in the diafiltrating concentrator (10 kDa) and centrifuged at 3220 g until the volume of protein solution decreased 8-10 folds. Concentrate was diluted up to a primary volume with buffer containing 20 mM $NaH_2PO_4/Na_2HPO_4$, 20 mM Sodium citrate (pH 4.5). Procedure was repeated till conductivity decreased below 8 mS/cm and protein solution subjected to the final purification step using SP sepharose FF resin (GEHealthcare Life Sciences, Uppsala, Sweden). Chromatography media was pre-equilibrated with cold buffer (20 mM $NaH_2PO_4/Na_2HPO_4$, 20 mM Citric acid, pH 4.5). Protein solution was loaded to column and SP sepharose bounded protein fraction was eluted by linear gradient of cold washing buffer additionally containing 500 mM of NaCl. After that, Kvarla was freeze-dried and applied for analysis.

Concentration of purified proteins was evaluated by Bradford assay or by comparison of band intensity with known BSA amount which was run on the same SDS-PAGE gel. The results of klebicin purification are summarized in the Table 1. FIG. 4 shows purified KpneM, KpneM2, KvarM, KpneA, KaerA and Kvarla klebicin proteins loaded on the same gel. All purified klebicins contain only 0.2-3.7% of impurities, as determined by capillary gel electrophoresis. The yields of individual klebicins after purification are in range of 0.34-1.1 mg/g FW. The purification of klebicins with greatest expression levels give biggest final yields and also best quality of purified proteins.

TABLE 1

| Purification method, obtained yields and purity of plant-expressed klebicins. | | | | |
|---|---|---|---|---|
| Klebicin | Purification method | Klebicin amount in crude extract (μg/g FW) | Yield of purified protein (μg/g FW) | Purity % |
| KpneM | Phenyl>DS>Q | 3239 ± 224 | 1134 ± 54 | 99.8 ± 0.3 |
| KpneM2 | Phenyl>DS>Q | 4448 ± 347 | 920 ± 55 | 99.5 ± 0.5 |
| KvarM | Phenyl>DS>Q | 2423 ± 146 | 535 ± 35 | 98.1 ± 1.0 |
| KpneA | Phenyl>DS>SP | 2677 ± 163 | 337 ± 26 | 97.2 ± 1.2 |
| KaerA | SP>DS>Q | 2718 ± 227 | 468 ± 46 | 96.3 ± 0.7 |
| Kvarla | Phenyl>DS>SP | 2697 ± 149 | 629 ± 31 | 98.9 ± 1.0 |

Example 4: Klebicin Activity Tests in Soft-Agar Overlay Assay

We tested the activity of crude bacteriocin-expressing plant extracts in a soft-agar overlay assay with twelve *Klebsiella* strains belonging to different species (*K. pneumoniae, K. quasipneumoniae, K. oxytoca, K. variicola* and *K. aerogenes*). *Klebsiella* strains were purchased from Leibniz Institute DSMZ-German Collection of Microorganisms and Cell Cultures and are described in Table 2.

Overnight *Klebsiella* cultures were equalized to $OD_{595}=1.0$ in LB medium and diluted 100× in 0.8% top agar preheated in a 55° C. water bath. Mixed overlay components were poured on plates containing solid agar (1.5% LB agar); the plates were kept at room temperature for a few minutes allowing the agar to harden. Sterile Whatman discs (6 mm diameter) were placed on soft-agar and respective amounts of klebicins (20 μl of crude extracts or 10 μg of purified klebicins) were applied to the disks. The plates were incubated overnight at 37° C. and the diameter of klebicin inhibition zones was observed. The results of this assay are summarized in FIG. 5.

Two of tested bacteriocins, KoxyY and KaerM demonstrated perceptible but narrow inhibition zones on the lawn of several tested strains, with KaerM forming larger hazy inhibition zones only on *K. aerogenes* lawn. Because of the weaker activity, these two proteins were not included in further experiments.

TABLE 2

| Klebsiella strains used in the study. | | |
|---|---|---|
| Strain | Culture collection number | Growing temperature |
| Klebsiella pneumoniae subsp.pneumoniae | DSM 26371, ATCC 700603 | 28° C. |
| Klebsiella pneumoniae | DSM 789, ATCC 4352 | 37° C. |
| Klebsiella pneumoniae subsp.pneumoniae | DSM 9377, ATCC 13887 | 37° C. |

TABLE 2-continued

| Klebsiella strains used in the study. | | |
|---|---|---|
| Strain | Culture collection number | Growing temperature |
| Klebsiella pneumoniae subsp. rhinoscleromatis | DSM 16231, ATCC 13884 | 37° C. |
| Klebsiella pneumoniae subsp.ozaenae | DSM 16358, ATCC 11296 | 28° C. |
| Klebsiella quasipneumoniae subsp.quasipneumoniae | DSM 28211 | 37° C. |
| Klebsiella quasipneumoniae subsp. similipneumoniae | DSM 28212 | 37° C. |
| Klebsiella oxytoca | DSM 5175, ATCC 13182 | 37° C. |
| Klebsiella oxytoca | DSM 6673, ATCC 43863 | 37° C. |
| Klebsiella variicola | DSM 15968, ATCC BAA-830 | 28° C. |
| Klebsiella aerogenes | DSM 30053 | 30° C. |
| Klebsiella aerogenes | DSM 12058 | 30° C. |

All seven remaining bacteriocins formed large inhibition zones on the lawn of several tested *Klebsiella* species and strains. All twelve tested strains were inhibited by not only one, but by several bacteriocins. The three remaining colM-like proteins demonstrated the largest activity spectrum and a similar activity pattern, targeting eleven out of twelve tested strains. However, KvarM formed significantly larger inhibition zones than both *K. pneumoniae* colM-like bacteriocins (KpneM and KpneM2). The two ColA-like proteins KpneA and KaerA also demonstrated very similar activity pattern, although zone diameter was different for some of the tested strains. And finally, both Colla-like proteins Kvarla and Kpnela demonstrated very similar activity patterns (FIG. 5). All bacteriocins formed inhibition zones on the strains belonging to all five different *Klebsiella* species with exception of Kvarla and Kpnela. The two colla-like proteins had little effect on neither of four tested *K. pneumoniae* strains.

Example 5: Evaluation of Klebicin Activity Against a Panel of Clinical *Klebsiella* Isolates All six purified klebicins were next tested against a larger panel of *Klebsiella* strains: 89 *K. pneumoniae* and 11 *K. oxytoca* strains, in total one hundred clinical *Klebsiella* isolates. Clinical *Klebsiella* strains used for agar overlay assay have been isolated in Lithuanian university of health sciences, Kaunas clinics, and are described in Table 3. Purified lyophilized klebicins were resuspended in deionized water and applied as 10 µl drops (10 µg of protein) on 6 mm Whatman discs placed on LB plates with streaked *Klebsiella*. After overnight incubation inhibition zones were measured.

KvarM demonstrated a surprisingly broad spectrum of activity. 85% of strains were sensitive to this klebicin (FIG. 6, Table 3). KpneM was not far behind, targeting 74% of tested strains, in general with slightly smaller inhibition zones. The specificity of KvarM and KpneM activity spectra were largely overlapping, but KvarM targeted 11 strains more that KpneM, and only one strain immune to KvarM was sensitive to KpneM (FIG. 6, Table 3). In contrast, the third M-type klebicin KpneM2 was much less active, targeting only 20% of strains. Both colA-like klebicins KpneA and KaerA targeted 30% and 28% of strains, respectively, with partially overlapping profiles. 9 strains immune to KaerA were sensitive to KpneA, and 7 strains immune to KpneA were sensitive to KaerA. KpneA also in general formed larger inhibition zones. Kvarla had the narrowest spectrum of activity and targeted only 10% of all strains, 6 *K. oxytoca* and 4 *K. pneumoniae* (FIG. 6, Table 3).

TABLE 3

| Antimicrobial activity of plant-made klebicins against clinical *Klebsiella* isolates. "MDR" means multi-drug-resistant. | | | | | | | | | |
|---|---|---|---|---|---|---|---|---|---|
| No inhibition zone | | Zone 7-10 mm | | Zone 11-15 mm | | | Zone 16-20 mm | | |
| – | | + | | ++ | | | +++ | | |
| No | Species | Isolated from | MDR | KpneA | KaerA | KpneM | KnpeM2 | KvarM | Kvarla |
| 1 | *K. pneumoniae* | urine | MDR | – | – | ++ | + | + | – |
| 2 | *K. pneumoniae* | bronch | MDR | – | – | ++ | + | ++ | – |
| 3 | *K. pneumoniae* | urine | MDR | – | – | +++ | ++ | +++ | – |
| 4 | *K. pneumoniae* | trachea | —— | – | – | ++ | – | ++ | – |
| 5 | *K. pneumoniae* | urine | MDR | – | – | ++ | – | ++ | – |
| 6 | *K. pneumoniae* | blood | MDR | – | – | ++ | + | + | – |
| 7 | *K. pneumoniae* | urine | —— | – | – | ++ | – | – | – |
| 8 | *K. pneumoniae* | urine | MDR | +++ | ++ | +++ | ++ | +++ | – |
| 9 | *K. pneumoniae* | urine | MDR | – | – | – | – | ++ | – |
| 10 | *K. pneumoniae* | gall | MDR | – | + | + | – | ++ | – |
| 11 | *K. pneumoniae* | pleura | MDR | – | – | + | – | + | – |
| 12 | *K. pneumoniae* | bronch | —— | + | – | + | – | ++ | – |
| 13 | *K. pneumoniae* | urine | MDR | – | – | ++ | ++ | ++ | – |
| 14 | *K. pneumoniae* | urine | MDR | – | + | ++ | – | ++ | – |
| 15 | *K. pneumoniae* | urine | MDR | + | – | ++ | + | ++ | – |
| 16 | *K. pneumoniae* | urine | MDR | – | – | + | – | + | – |
| 17 | *K. pneumoniae* | urine | MDR | – | – | + | – | ++ | – |
| 18 | *K. pneumoniae* | urine | MDR | – | – | ++ | + | ++ | – |

TABLE 3-continued

Antimicrobial activity of plant-made klebicins against clinical *Klebsiella* isolates.
"MDR" means multi-drug-resistant.

| | | | | | | | | | |
|---|---|---|---|---|---|---|---|---|---|
| 19 | K. pneumoniae | urine | — | + | + | ++ | + | +++ | − |
| 20 | K. pneumoniae | urine | MDR | ++ | ++ | + | − | ++ | − |
| 21 | K. pneumoniae | urine | MDR | ++ | − | + | + | ++ | − |
| 22 | K. pneumoniae | urine | MDR | − | − | + | − | ++ | − |
| 23 | K. pneumoniae | urine | MDR | − | − | + | − | ++ | − |
| 24 | K. pneumoniae | urine | MDR | − | + | ++ | + | ++ | − |
| 25 | K. pneumoniae | urine | MDR | − | − | + | − | ++ | − |
| 26 | K. pneumoniae | urine | MDR | ++ | − | ++ | + | +++ | − |
| 27 | K. pneumoniae | blood | MDR | − | − | + | − | + | − |
| 28 | K. pneumoniae | urine | MDR | − | − | − | − | + | − |
| 29 | K. pneumoniae | urine | MDR | − | − | +++ | ++ | ++ | − |
| 30 | K. pneumoniae | blood | MDR | ++ | + | +++ | + | +++ | − |
| 31 | K. pneumoniae | bronch | MDR | + | − | + | − | ++ | − |
| 32 | K. pneumoniae | bronch | MDR | − | − | +++ | − | ++ | − |
| 33 | K. pneumoniae | bronch | — | +++ | +++ | − | − | − | ++ |
| 34 | K. pneumoniae | bronch | MDR | − | − | ++ | − | ++ | − |
| 35 | K. pneumoniae | wound | MDR | − | − | + | + | ++ | − |
| 36 | K. pneumoniae | urine | MDR | − | − | − | − | ++ | − |
| 37 | K. pneumoniae | bronch | — | +++ | ++ | +++ | − | +++ | − |
| 38 | K. pneumoniae | urine | MDR | − | − | + | − | ++ | − |
| 39 | K. pneumoniae | pus | MDR | − | − | + | − | + | − |
| 40 | K. pneumoniae | urine | MDR | − | − | − | − | − | − |
| 41 | K. pneumoniae | urine | MDR | − | − | − | − | ++ | − |
| 41 | K. pneumoniae | urine | — | − | − | ++ | − | +++ | − |
| 43 | K. pneumoniae | bronch | MDR | − | − | + | − | ++ | − |
| 44 | K. pneumoniae | urine | MDR | − | − | + | − | ++ | − |
| 45 | K. pneumoniae | urine | MDR | − | − | + | − | ++ | − |
| 46 | K. pneumoniae | urine | MDR | − | − | − | − | + | − |
| 47 | K. pneumoniae | bronch | MDR | + | − | ++ | + | +++ | − |
| 48 | K. pneumoniae | bronch | MDR | − | − | ++ | − | +++ | − |
| 49 | K. pneumoniae | wound | MDR | − | − | + | + | ++ | − |
| 50 | K. pneumoniae | pus | MDR | − | − | − | − | ++ | + |
| 51 | K. pneumoniae | gall | MDR | − | − | ++ | − | ++ | − |
| 52 | K. pneumoniae | gall | — | − | − | ++ | − | ++ | + |
| 53 | K. pneumoniae | gall | MDR | − | − | ++ | ++ | ++ | − |
| 54 | K. pneumoniae | urine | — | ++ | ++ | ++ | − | +++ | − |
| 55 | K. pneumoniae | pus | MDR | − | − | + | − | ++ | − |
| 56 | K. pneumoniae | urine | MDR | − | − | − | − | − | − |
| 57 | K. pneumoniae | joint | — | − | − | ++ | − | ++ | − |
| 58 | K. pneumoniae | phlegm | MDR | − | − | + | − | ++ | − |
| 59 | K. pneumoniae | bronch | — | ++ | + | ++ | − | +++ | − |
| 60 | K. pneumoniae | urine | MDR | − | − | + | − | ++ | − |
| 61 | K. pneumoniae | pus | — | ++ | + | ++ | ++ | +++ | − |
| 62 | K. pneumoniae | abdomen | MDR | − | − | + | − | ++ | − |
| 63 | K. pneumoniae | urine | MDR | − | − | − | − | − | − |
| 64 | K. pneumoniae | urine | MDR | − | − | ++ | − | ++ | − |
| 65 | K. pneumoniae | urine | — | − | − | − | − | − | − |
| 66 | K. pneumoniae | blood | MDR | − | − | ++ | − | ++ | − |
| 67 | K. pneumoniae | pleura | MDR | − | − | + | − | ++ | − |
| 68 | K. pneumoniae | bronch | — | ++ | ++ | ++ | − | +++ | − |
| 69 | K. pneumoniae | urine | MDR | ++ | ++ | ++ | + | +++ | − |
| 70 | K. pneumoniae | blood | — | ++ | + | − | − | +++ | − |
| 71 | K. pneumoniae | bronch | MDR | − | − | + | − | ++ | − |
| 72 | K. pneumoniae | bronch | MDR | − | − | ++ | − | ++ | − |
| 73 | K. pneumoniae | urine | — | +++ | ++ | ++ | − | ++ | − |
| 74 | K. pneumoniae | trachea | — | +++ | +++ | ++ | − | ++ | +++ |
| 75 | K. pneumoniae | gall | — | − | − | ++ | − | ++ | − |
| 76 | K. pneumoniae | urine | MDR | ++ | + | ++ | − | ++ | − |
| 77 | K. pneumoniae | urine | MDR | + | − | ++ | − | ++ | − |
| 78 | K. pneumoniae | urine | — | +++ | +++ | ++ | − | +++ | − |
| 79 | K. pneumoniae | urine | MDR | − | − | + | − | + | − |
| 80 | K. pneumoniae | urine | MDR | − | − | − | − | − | − |
| 81 | K. pneumoniae | bronch | MDR | − | − | + | − | ++ | − |
| 82 | K. pneumoniae | bronch | — | − | − | − | − | − | − |
| 83 | K. pneumoniae | urine | — | + | + | − | − | − | − |
| 84 | K. pneumoniae | urine | MDR | − | − | − | − | − | + |
| 85 | K. pneumoniae | blood | — | ++ | + | ++ | − | ++ | − |
| 86 | K. pneumoniae | urine | MDR | − | − | + | − | ++ | − |
| 87 | K. pneumoniae | urine | MDR | − | − | − | − | − | − |
| 88 | K. pneumoniae | urine | MDR | − | − | + | − | ++ | − |
| 89 | K. pneumoniae | bronch | — | + | + | ++ | − | ++ | − |
| 90 | K. oxytoca | urine | — | + | + | − | − | + | − |
| 91 | K. oxytoca | urine | MDR | − | + | − | − | − | ++ |
| 92 | K. oxytoca | urine | MDR | − | ++ | − | − | − | ++ |
| 93 | K. oxytoca | bronch | — | − | + | ++ | − | + | − |
| 94 | K. oxytoca | urine | — | − | − | − | − | + | − |
| 95 | K. oxytoca | biopsy | — | − | + | − | − | ++ | − |

TABLE 3-continued

Antimicrobial activity of plant-made klebicins against clinical *Klebsiella* isolates.
"MDR" means multi-drug-resistant.

| 96 | *K. oxytoca* | urine | — | – | – | – | – | – | + |
| 97 | *K. oxytoca* | urine | — | + | ++ | – | – | ++ | ++ |
| 98 | *K. oxytoca* | pus | — | + | – | – | – | ++ | – |
| 99 | *K. oxytoca* | urine | — | ++ | – | – | ++ | +++ | + |
| 100 | *K. oxytoca* | bronch | — | – | – | – | – | – | + |

Example 6: Evaluation of Klebicin Activity Against *Klebsiella* Strains in Liquid Cultures and Biofilms We next performed a more detailed analysis of klebicin activity in liquid medium and on young, one day old biofilms with five representatives of different *Klebsiella* species: *K. pneumoniae, K. quasipneumoniae, K. oxytoca, K. variicola* and *K. aerogenes*.

For evaluation of klebicin activities in liquid medium, overnight *Klebsiella* cultures were diluted to $OD_{595}$=0.3 in iron-deficient Casamino Acids (CAA) medium (BD Bioscience) up to 1.2 mL. Lyophilized purified klebicins were resuspended in CAA medium, added to diluted bacterial suspension and incubated for 5.5-6.5 hours at 37° C. with shaking (200 rpm). The antimicrobial activity of klebicins was evaluated by determining cell numbers of bacterial test culture. Serial dilutions of 10, 10-1, 10-2, 10-3, 10-4 and 10-5 were made, plated on LB agar plates, incubated overnight at 37° C. and the CFU calculated.

Biofilms were grown as described by Moskowitz et al. (2004) and Paškevičius et al. (2017) with some modifications. Briefly, *K. quasipneumoniae, K. oxytoca, K. variicola, K. aerogenes* strains were grown overnight in LB and diluted to OD=0.1 with fresh CAA medium. 10 μl of bacteria culture were transferred to the wells of a 96-well microtiter plate (Nalgene Nunc International, Rochester, N.Y.) with 90 μl of CAA medium. Bacterial biofilms were formed by immersing the pegs of a modified polystyrene microtiter lid (Nunc TSP system) into the biofilm growth plate, followed by incubation at 30° C. or 37° C. controlled by a thermostat for 20 h. For the treatment with klebicins, peg lids were rinsed three times in sterile water, placed into microtiter plates containing 5 μg/mL of klebicins diluted in 100 μl CAA per well and incubated for 5 h at 30° C. or 37° C., depending on the strain. After incubation with klebicins, peg lids were again rinsed three times in sterile water, placed into CAA in a sterile microtiter plate and centrifuged at 810 g for 30 min. 6 identically treated wells were pooled each time, serial dilutions were made and bacteria were plated on LB plates for CFU counting.

For the liquid culture assay, one best performing klebicin of each group (colM-like, colA-like and colla-like) from Example 4 at concentration of 5 μg mL-1 was tested. Klebicin KvarM inhibited the growth of all five strains, reducing the CFU number in quite similar extent—by four orders of magnitude for *K. pneumoniae* DSM 16231 and about three orders of magnitude for all remaining Klebsiellae (FIG. 7). Kvarla inhibited four strains and was the most efficient of all three klebicins, reducing CFU number by four to nine orders of magnitude, depending on the strain (FIG. 7) (as it was shown in FIG. 5, *K. pneumoniae* DSM16231 is insensitive to this klebicin). KpneA reduced CFU counts of three strains by 4.6 to 5.7 logs (FIG. 7).

For the biofilm assays, we used the same *Klebsiella* strains as in the liquid culture assays. First, we tested the ability of these five strains to form biofilms. Four of the tested strains formed biofilms in tested conditions, with exception of *K. pneumoniae* DSM 16231, thus this strain was not used for further experiments. The biofilms of all remaining four stains were treated for 20 h each with two klebicins, which showed the best results in liquid culture assays. The results obtained with biofilms quite closely reflected the results obtained in liquid culture assays, with exception of *K. quasipneumoniae*, whose biofilms were completely eradicated by KpneA and Kvarla (FIG. 8). For all remaining strains, klebicins treatment decreased CFU numbers in biofilms in similar extent as in liquid cultures, with only slight variations of Δ logs achieved (FIG. 7, FIG. 8).

Example 7: Evaluation of Klebicin Antimicrobial Activity In Vivo

For the initial demonstration of klebicins activity in vivo, we performed *Klebsiella* challenge assay in a non-mammal animal model, *Galleria mellonella* larvae. *Galleria mellonella*, the greater wax moth or honeycomb moth, is a moth of the family Pyralidae. *Galleria mellonella* have been shown to be a convenient model organism for in vivo toxicology and pathogenicity testing, replacing the use of small mammals in such experiments (Harding et al. 2013; Paškevičius et al. 2017).

We selected Kvarla for this assay as one of the most active klebicins and *K. quasipneumoniae* DSM 28212 as Kvarla-sensitive challenge strain. *G. mellonella* challenge experiments were performed as described in Paškevičius et al. (2017), with some modifications. Overnight *K. quasipneumoniae* DSM 28212 strain culture was grown in CAA medium and diluted in 0.8% NaCl in order to achieve a concentration of 1.2-3.2×10⁶ CFU mL-1 in 10 μL of *K. quasipneumoniae* culture and 10 μL of klebicins solution were injected into hemocoel of fifth instar *G. mellonella* larvae (Livefood UK) in proximity of the left and/or right prolegs. Klebicins were injected two hours post infection with *K. quasipneumoniae*. Injected larvae were incubated at 37° C. in 9 cm Petri dishes without food for up to 3 days. Caterpillars were considered dead when they displayed no movement in response to mechanical stimulus to the head, leading to distinct change in color from cream to dark brown/black. Twenty larvae were used per each treatment point.

First, we determined that minimal lethal dose (MLD) of challenge strain sufficient to kill all the larvae in 68h (the duration of experiment) is $2.3 \times 10^4$ CFU.

We next performed the challenge experiment with MLD and with two additional challenge doses, one inferior and one superior to MLD by factor 1.9 and 1.4, respectively. $1.2 \times 10^4$ CFU were not sufficient to kill all the larvae, as 15% of larvae still survived after 68h. However, 2.3 and $3.2 \times 10^4$ CFU were sufficient to kill all the larvae in 44 h. Injection of Kvarla 2 hours post infection completely rescued all the larvae infected by 1.2 and $2.3 \times 10^4$ CFU. Larvae infected by the highest amount of bacteria ($3.2\times10^4$ CFU) were rescued partially, with 85% of larvae surviving till the end of experiment (FIG. 9).

Summarizing, from the activity assays, one can see that KvarM has exceptionally wide spectrum of activity as it could target *Klebsiella* strains belonging to *K. pneumoniae, K. quasipneumoniae, K. variicola, K. oxytoca*, and *K. aerogenes* species. It was also active against 85% of strains in the panel of antibiotic-resistant clinical *Klebsiella* isolates. In liquid culture assay, this klebicin could reduce the colony forming number count by as much as three to four logs and more than by two logs in biofilm assay. Pore-forming klebicins were in general even more efficient in reducing bacterial numbers in liquid culture or in biofilms than peptidoglycan synthesis inhibitors and were able to achieve four to nine logs of CFU counts reduction in liquid cultures and two to almost six logs of CFU counts reduction in biofilms. Kvarla, which has demonstrated highest efficiency in vitro, was also tested in vivo in *G. mellonella* larvae challenge assays with very good outcome. However, the applicability of this klebicin is currently handicapped by the fact that it is not broadly active against *K. pneumoniae*, although it works well on its close relative *K. quasipneumoniae*.

Example 8: Identification of Klebicin Receptors/Translocators

Universal feature of colicins is their domain organization, and each colicin appears to have receptor binding, translocation and cytotoxic domains, a feature that is conditioned by the necessity of these bacteriocins to cross the outer membrane of gram-negative bacteria (Kleanthous, 2010). Pore-forming klebicins amino acid sequence alignments with their *E. coli* counterparts reveal that their killing domains show significant degree of homology. However, as a rule, pore forming klebicins are smaller than colicins. Their amino-terminal parts, which should contain translocation and receptor binding domains, are much shorter than respective domains of colicins and have little or no sequence similarity. Thus, we anticipated that the translocation mechanism of pore-forming klebicins might be different from their *E. coli* counterparts.

In sharp contrast to some other bacteriocins, which are strictly species-specific (for example, pyocins), klebicin activity is not confined to the single species from which they are isolated, but at least to the genus. In this regard, it was important to inquire the players involved in the reception and translocation mechanisms of klebicins. *K. quasipneumoniae* DSM 28212, a strain with known genome sequence and sensitivity to all the klebicins tested, was subjected to several rounds of transposon mutagenesis and pooled mutants were tested for their sensitivity to different klebicins.

Transposon mutagenesis of *K. quasipneumoniae* DSM 28212 was performed as described in Martínez-García et al. (2011). The suicide delivery of mini-transposons localized in pBAM1 plasmid was performed by triparental mating. The plasmid was mobilized from *E. coli* CC118λpir (pBAM1) donor cells into *K. quasipneumoniae* DSM 28212 cells with the assistance of the helper strain *E. coli* HB101 (pRK600). Obtained kanamycin-resistant clones were confirmed for the loss of the ampicillin resistance and their genomic DNA was used for the PCR amplification of the transposon adjacent regions, followed by sequencing, as described by Martínez-García et al. (2011).

29 independent mutant clones were isolated, and transposon insertions were successfully mapped in 18 klebicin-resistant mutants. To confirm that klebicin sensitivity loss was indeed due to the mapped mutations, we performed complementation assays by ectopic expression of respective wild-type genes.

For complementation assays, *Klebsiella* genome regions, containing ExbB, ExbBD, OmpC, FhuA, TonB and FimB gene ORFs along with 5' non-coding promoter regions, were PCR-amplified from *K. quasipneumoniae* DSM 28212 genomic DNA with help of Phusion DNA polymerase (Thermofisher Scientific Baltics) and ligated in pJET1.2 (Thermofisher Scientific Baltics). After sequencing, cloned fragments were excised with restriction endonucleases pair specific for each fragment, ligated in pACYC184 (NEB) and transformed into respective *K. quasipneumoniae* mutants. The sequences of primers used and cloning strategy are described in Table 4.

TABLE 4

Primers used for amplification of genes used in complementation assays. Restriction endonuclease sites are in italics, primers binding sequences are in bold.

| Gene | Primer | Sequence | pACYC184 cloning |
|---|---|---|---|
| ExbB | ExbB Eco88I fwd | *AAACTCGGG* TTGATGAAC CTGTTTTTA TACGTCT (SEQ ID NO: 10) | Eco88I-Eco81I |
| | ExbB Eco81I rev | *AAACCTGAG* GTCAACCTA CCCGTAATT TCTGCG (SEQ ID NO: 11) | |
| ExbBD | ExbB Eco88I fwd | *AAACTCGGG* TTGATGAAC CTGTTTTTA TACGTCT (SEQ ID NO: 12) | Eco88I-Eco81I |
| | ExbD Eco81I rev | *AAACCTCAG* GTTATTTGG CTTTGACGG TCTC (SEQ ID NO: 13) | |
| FhuA | FhuA Eco81I fwd | *AAACCTCAG* GTTTAAGCC CTAAGACCA GACCC (SEQ ID NO: 14) | Eco81I |
| | FhuA Eco81I rev | *AAACCTGAG* GTTAGAAAC GGAAGGTGG CGGTG (SEQ ID NO: 15) | |
| FimB | FimB Eco88I fwd | *AAACTCGGG* GCTCCCGTA GCAAATAAA AACG (SEQ ID NO: 16) | Eco88I-Eco81I |
| | FimB Eco81I rev | *AAACCTGAG* GTTACTGAA GCAGCGACA GGCG (SEQ ID NO: 17) | |

TABLE 4-continued

Primers used for amplification of genes
used in complementation assays.
Restriction endonuclease sites are in
italics, primers binding sequences
are in bold.

| Gene | Primer | Sequence | pACYC184 cloning |
|------|--------|----------|------------------|
| OmpC | OmpC Eco88I fwd | AAACTCGGG CTTGTGGCT GAACGACTC ATCA (SEQ ID NO: 18) | Eco88I-Eco81I |
| | OmpC Eco81I rev | AAACCTGAG GTTAGAACT GGTAAACCA GGCCC (SEQ ID NO: 19) | |
| TonB | TonB PsyI fwd | AAAGACCGG GTCGGCAAA GCTCCTTAT CAATAAACA (SEQ ID NO: 20) | BseSI-PsyI |
| | TonB BseSI rev | AAAGTGCCC TCAGTTAAT CTCGACGCC GTTG (SEQ ID NO: 21) | |

The summarized results from mutant klebicin sensitivity studies and complementation assays are presented in Table 5.

TABLE 5

Characterization of klebicin resistant mutants
obtained by transposon mutagenesis.

| Mutant No. | Selected by resistance to: | Resistant to klebicins: | Mutation | Comp-lementation |
|------------|---------------------------|------------------------|----------|------------------|
| #1 | KpneM | KpneM2, KvarM, | FhuA | + |
| #2 | KpneM | KpneM2, KvarM | FhuA | NT |
| #3 | KpneM | KpneM2, KvarM | FhuA | NT |
| #4 | KpneM | KpneM2, KvarM, KpneA, KaerA | TonB | + |
| #7 | KpneM2 | KvarM, KpneM KpneM2 (partial res. to KvarM, KpneA, KpneM) | FhuA ExbB | NT +(ExbBD) |
| #8 | KaerA | | | |
| #9 | KaerA | Kvarla, KpneA | OmpC | + |
| #10 | KpneA | KpneM2, KpneM, KvarM, KaerA | ExbB | +(ExbBD) |
| #11 | KpneA | Kvarla, KaerA KpneM, KpneM2 | OmpC | NT |
| #12 | KvarM | KpneM, KpneM2, | FhuA | NT |
| #13 | KvarM | KaerA (partial res. to KpneA) | ExbB | NT |
| #14 | KpneM2 | KvarM, KpneM | FhuA | NT |
| #15 | KpneM2 | KvarM, KpneM | FhuA | NT |
| #16 | KpneM2 | KvarM, KpneM | FhuA | NT |
| #17 | KpneM2 | KvarM, KpneM | FhuA (outside) | NT |
| #18 | KpneM2 | KpneM, KvarM, KaerA (partial res. to KpneA) | ExbB | NT |
| #20 | Kvarla | KpneA, KaerA | FimB | - |

"NT" means "Not Tested", "+" means "Complemented", "-" means "Not Complemented"

Based on the obtained results, all klebicins with exception of Kvarla are similar to group B colicins and use the TonB-dependent translocation pathway. All three M-type klebicins require FhuA, TonB and ExbB for their reception-translocation, as their *E. coli* homologue colicin M. KpneA and KaerA also depend on the TonB translocation pathway and they need in addition the functional OmpC. So far we could not identify any other putative receptor for these two klebicins (Table 6).

TABLE 6

Identified Klebsiella proteins involved in reception
and translocation of klebicins.

| Klebicin | Receptor | Mechanism of translocation | Cytotoxicity |
|----------|----------|---------------------------|--------------|
| KpneM | FhuA | TonB, ExbB | Peptidoglycan synthesis inhibitor |
| KpneM2 | FhuA | TonB, ExbB | Peptidoglycan synthesis inhibitor |
| KvarM | FhuA | TonB, ExbB | Peptidoglycan synthesis inhibitor |
| KpneA | OmpC | TonB, ExbB | Pore forming |
| KaerA | OmpC | TonB, ExbB | Pore forming |
| Kvarla | OmpC | Questionable | Pore forming |

Kvarla-resistant transpositional mutants were very hard to obtain, and only some false-positive clones were isolated. Thus, we could identify only one protein participating in Kvarla reception—translocation, the outer membrane protein C (OmpC). OmpC mutants were selected by their resistance to KpneA and KaerA and it appeared that they are equally resistant to Kvarla.

Summarizing, we thus demonstrated that all three M-type klebicins KpneA, KpneM2 and KvarM are translocated by a mechanism similar to that of colicin M, and they need FhuA receptor and TonB-related translocation pathway to enter the periplasm and exercise their activity.

Two klebicins which we named KpneA and KaerA based on their killing domain similarity to colicin A, appeared also dependent on the TonB translocation pathway. This is in contrast to colicin A, which is translocated by TolA-dependent pathway. Also, while colicin A binds to BtuB, we did not isolate any BtuB mutants resistant to KpneA or KaerA. However, both KpneA and KaerA need functional OmpC, an analog of OmpF, which participates also in colA transloca-tion (Kleanthous 2010). We have so far not identified any other putative receptor for these two klebicins.

Kvarla is different from all remaining klebicins, as it appears to be functional in all TonB and ExbB mutants. Thus, based on our results, Kvarla do not use TonB-depen-dent translocation pathway. Taking into account that all described colicins use either TonB or TolA as translocators, it would be expected that this protein is translocated by a Tol-dependent pathway. However, we did not isolate any single transpositional mutant of Tol-dependent pathway related genes that would be resistant to Kvarla. It certainly could be related to the limits of the method used, as Kvarla-resistant transposon mutants were very hard to obtain and only some false-positive clones were isolated. Mutations with high fitness penalty might not have been obtained in the conditions used for selection. Thus, we could thus far identify only one protein participating in Kvarla reception-translocation, the outer membrane protein C (OmpC). OmpC mutants were selected by their resistance to KpneA and KaerA and it appeared that they are equally resistant to Kvarla.

The further elucidation of klebicin receptors and translo-cators is important also for practical use of these klebicins. Klebicins are most promising for use for fighting antibiotic-resistant strains. However, it has been shown that 97.1% of carbapenem-resistant *Klebsiella* strains do not express or express less OmpC or OmpF (Ye et al., 2018). We did not test carbapenem-resistant strains in our study, but it indicates that carbapenem-resistant *Klebsiella* could be expected to be resistant to KpneA, KaerA and Kvarla, as all these klebicins require functional OmpC for their activity. The next step would be the attempt to change the specificity of klebicins by engineering the proteins, for example by swapping their receptor-translocation and killing domains.

Meanwhile, we can conclude that in the current state of research we have a panel of six highly efficient plant-expressed klebicins, which can together target about 91% of

*Klebsiella aerogenes* DSM 30053 were incubated at 30° C., *Klebsiella quasipneumoniae* subsp. *similipneumoniae* DSM 28212 and *Klebsiella oxytoca* DSM 5175 at 37° C.

MICs were determined by visual examination of bacterial growth in microplate wells. If the difference between two repeats was in one protein dilution, the MIC was determined as a mean of two concentrations.

Table 7 shows MIC values of 6 klebicins against 5 selected sensitive *Klebsiella* strains determined in µg protein/ml solution as well as in nM (µM).

TABLE 7

| | | | | | |
|---|---|---|---|---|---|
| MICs of klebicin bacteriocins against selected Klebsiella strains. | | | | | |
| Strain Klebicin | Klebsiella pneumoniae subsp. ozaenae DSM 16358 | Klebsiella quasipneumoniae subsp. similipneumoniae DSM 28212 | Klebsiella oxytoca DSM 5175 (ATCC 13182) | Klebsiella variicola DSM 15968 (ATCC BAA-830) | Klebsiella aerogenes DSM 30053 |
| KpneA | >50µg/ml >1.3 pM | 0.6 µg/ml 15 nM | NT | 0.2µg/ml 3.8 nM | NT |
| KaerA | >50µg/ml >1.3 pM | 0.2 µg/ml 5.0 nM | NT | 0.1 µg/ml 2.5 nM | NT |
| KpneM | 0.6µg/ml 19.5 nM | 1.9 µg/ml 63 nM | NT | 0.39 µg/ml 13 nM | 1.2 µg/ml 40 nM |
| KpneM2 | 0.8µg/ml 27 nM | >50 µg/ml >1.7 pM | NT | NT | 0.2 µg/ml 6.7 nM |
| KvarM | 0.1µg/ml 3.3 nM | >50 µg/ml >1.7 µM | 37.5µg/ml 1.3 µM | 0.2 µg/ml 6.6 nM | 0.6 µg/ml 20 nM |
| Kvarla | NT | 1.2 µg/ml 27.5 nM | 2.4 µg/ml 54 nM | 0.39 µg/mL 9.0 nM | 0.1 µg/mL 2.3 nM | tested clinical strains. Even without further engineering and improvement, these proteins could be further developed for their potential use in medicine as antimicrobials against antibiotic-resistant *Klebsiella*.

Example 10: MIC Determination for Klebicins KpneA, KaerA, KpneM, KpneM2, KvarM and Kvarla Against Several *Klebsiella* Species The minimum inhibitory concentration (MIC) was calculated as the lowest concentration of bacteriocin, which prevented visible growth of corresponding bacterial strain. For determination of MICs of individual klebicins, purified lyophilized KpneA, KaerA, KpneM, KpneM2 and KvarM proteins were dissolved in sterile distilled water at the concentration of 0.5 µg/µl. For each individual bacteriocin, serial 2-fold dilutions in MHB medium (Müller-Hinton Broth; Mueller & Hinton (1941) Experimental Biology and Medicine. 48 (1): 330-333) were prepared. 10 µl aliquots of each protein dilution were loaded into empty wells of sterile 96 well microplates. Two repeats of every evaluation point were made.

Overnight bacterial cultures grown in MHB medium were diluted to $OD_{595}$=0.5 in 1 ml of MHB, then diluted 1000-fold in 10 ml of the same medium. 90 µl aliquots of diluted bacterial suspensions were loaded using multichannel pipette into each well of 96-well microplate already containing protein dilutions. Additional aliquots of diluted bacterial suspension were plated on MHA medium (Müller-Hinton Agar; MHB containing 1.7% agar) for CFU enumeration in initial bacterial inoculum. For bacterial growth, microplates and agar plates were incubated at 30° C. or 37° C. depending on the optimal growth conditions for *Klebsiella* strains for 20h. *Klebsiella pneumoniae* subsp. *ozaenae* DSM 16358, *Klebsiella variicola* DSM 15968 and In most cases, determined klebicin MIC values were below 1-2 µg/ml. Nguen et al. (Scientific Reports (2018) 8:241) determined MICs of 20 conventional antibiotics against 1497 strains of *Klebsiella*. Typically, MIC values determined in this study were found between 0.5 and 32 µg/ml. Thus, klebicins are comparable or superior to conventional antibiotics in terms of antibacterial activity calculated on the weight basis. Given the difference in molecular weight (most antibiotics have MW of less than 1 kDa), klebicins have significantly higher antibacterial activity calculated on the molar basis.

Example 11: Stability of Klebicins KpneA, KaerA, KpneM, KpneM2, KvarM and Kvarla Upon the Storage For stability evaluation, purified lyophilized klebicin protein samples were stored at −20° C., 5° C. and room temperature (approx. 23° C.). Protein stability was assessed on the basis of antimicrobial activity at following time points: the day 0, 1 week, 2 weeks, 3 weeks, 5 weeks, 3 months, 6 months, 10 months and 12 months of storage. Protein activity against susceptible bacterium was evaluated in liquid cultures or by radial diffusion assay. Klebicins were tested with next strains: KpneM and KpneM2 with *K. pneumoniae* DSM16358, Kvarla with *K. oxytoca* DSM5175, KpneA, KaerA and KvarM with *K. quasipneumoniae* DSM28212.

Lyophilized protein samples were resuspended in distilled water (0.2-0.4 mg/ml). Soluble protein concentration was measured for each sample using Bradford assay. For the stability evaluation in liquid culture, 5 µg of bacteriocin solution were added to 1 ml of the suspension of susceptible bacterial strain of OD600=0.3 in CAA medium ("0" time point). Bacteria mixed with bacteriocin were incubated for 4.5 h at the shaker. *K. oxytoca* DSM5175 and *K. quasip-neumoniae* DSM28212 were incubated at 37° C., *K. pneu-moniae* DSM16358 was incubated at 30° C. Serial dilutions were made in LB medium. Bacteria were plated on LB agar plates and incubated overnight at 30° C. or 37° C., then CFU was calculated. Antimicrobial activity was evaluated as CFU/mL Δ $\log_{10}$ in regard to untreated sample.

For radial diffusion assay, serial 1:2 dilutions of proteins solubilized in PBS buffer were made. 5 μL of protein dilutions (1-1.8 μg of protein before dilution), were spotted on soft agar plates with susceptible bacterial strain. Residual activity of klebicins was evaluated after o/n incubation of plates. Antimicrobial activity was evaluated as specific activity units (AU)—highest dilution giving a difference to non-affected bacterial growth area determined by visual inspection of plates for bacterial growth inhibition by hold-ing the plate in front of a light source. Highest dilution with growth inhibition was recorded as an activity in AU/μg of bacteriocins. All experiments were performed in triplicate.

Figure 11A:
Figure 11B:
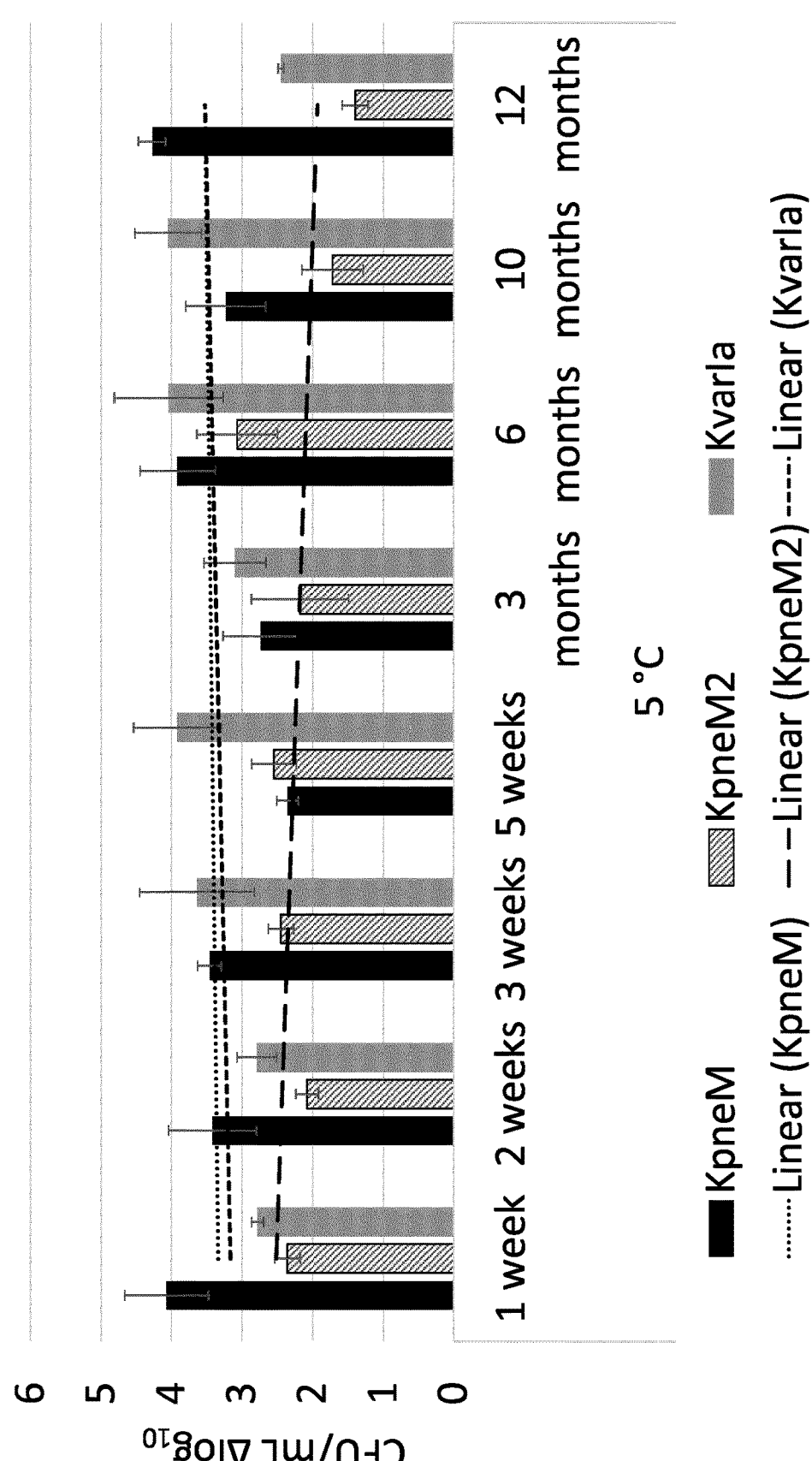
Figure 11C:
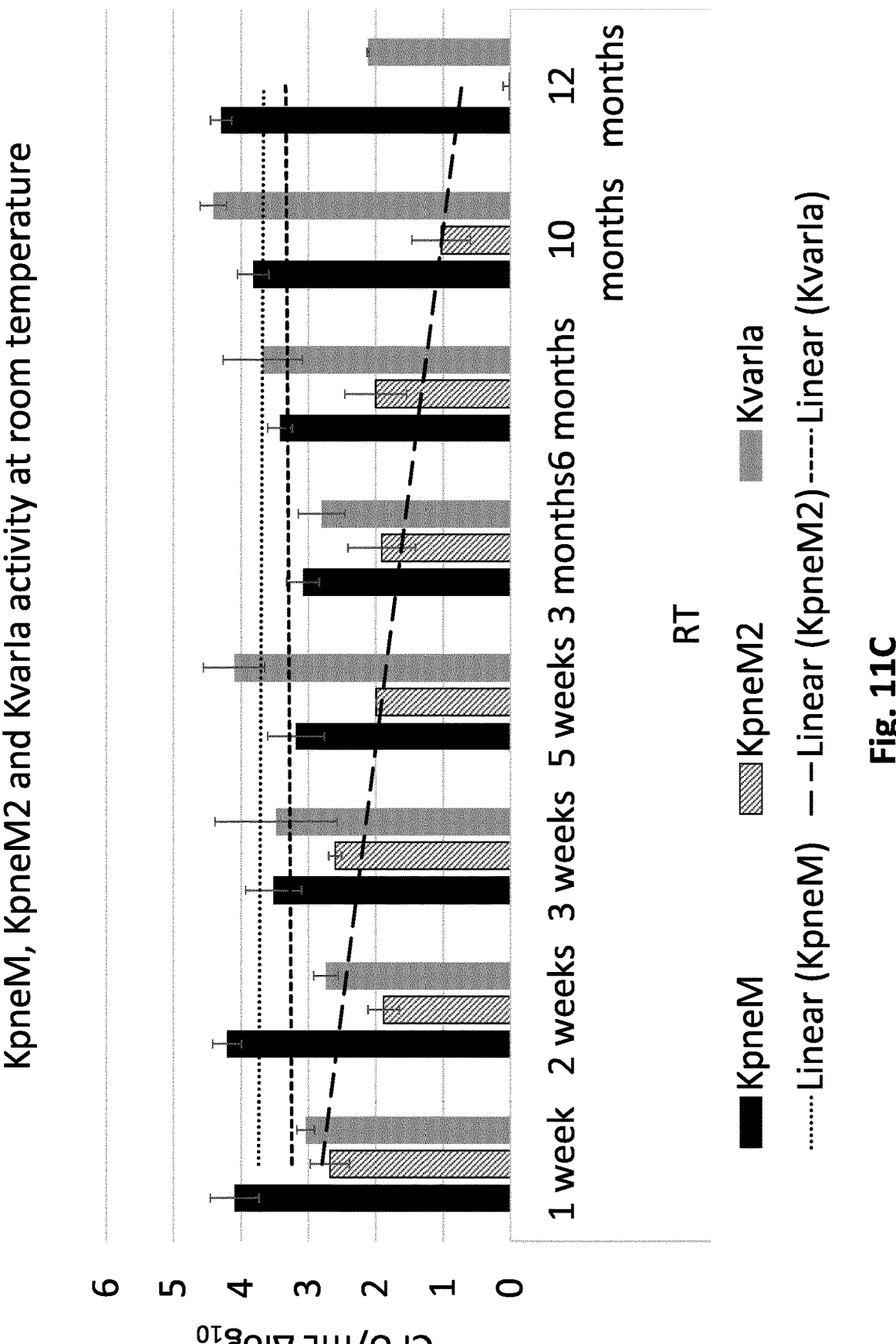
Figure 11D:
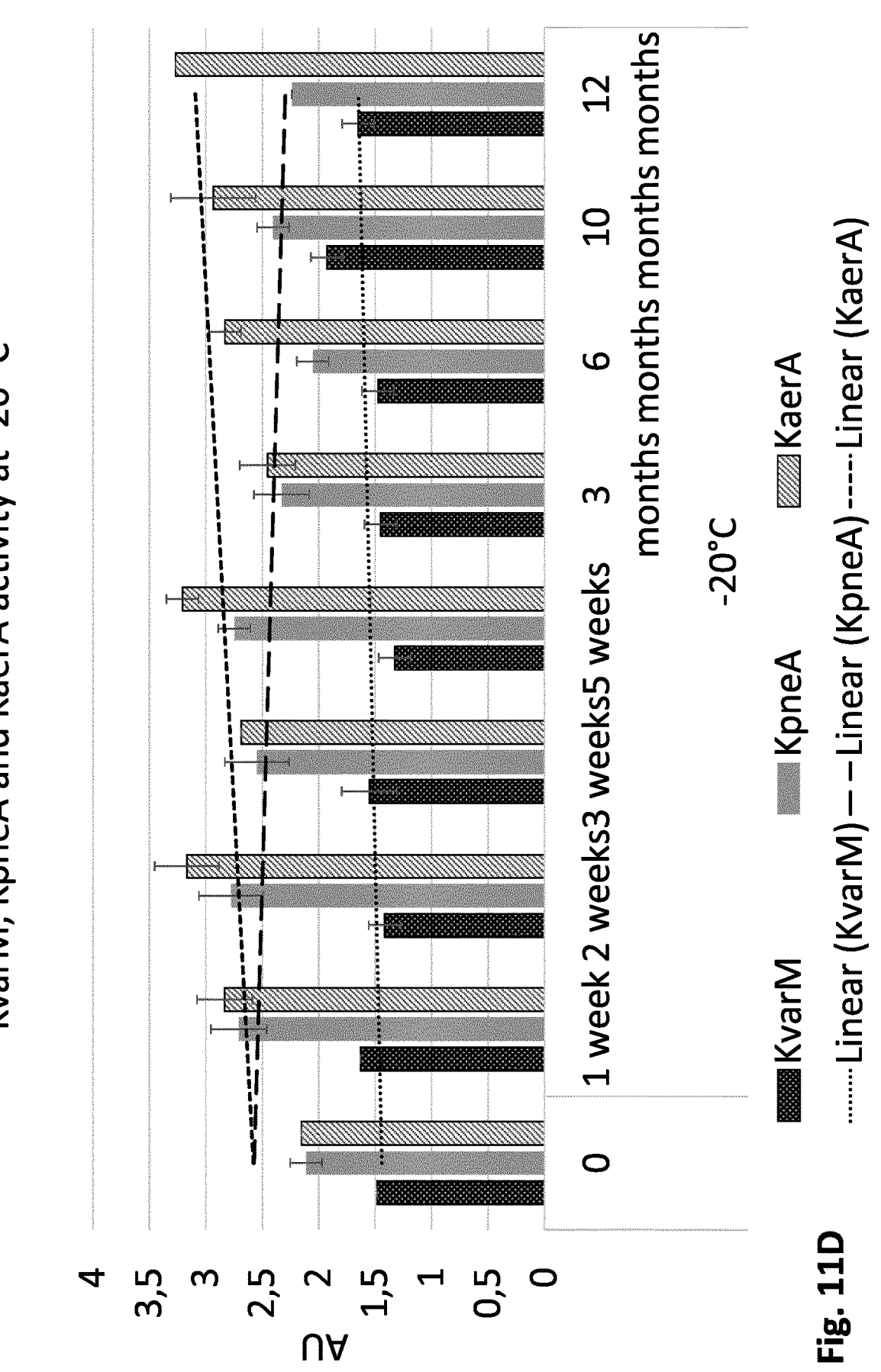
Figure 11E:
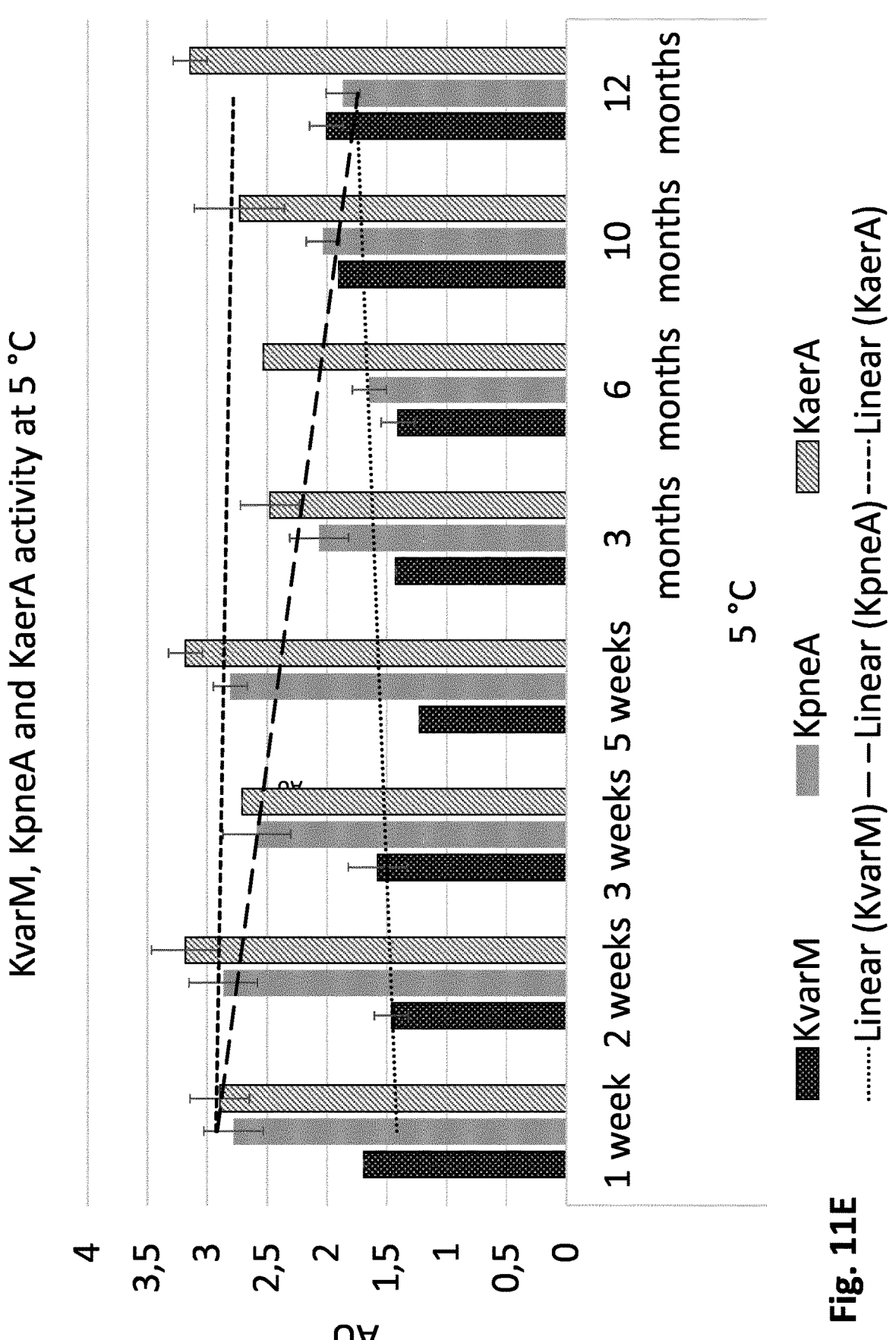
Figure 11F:
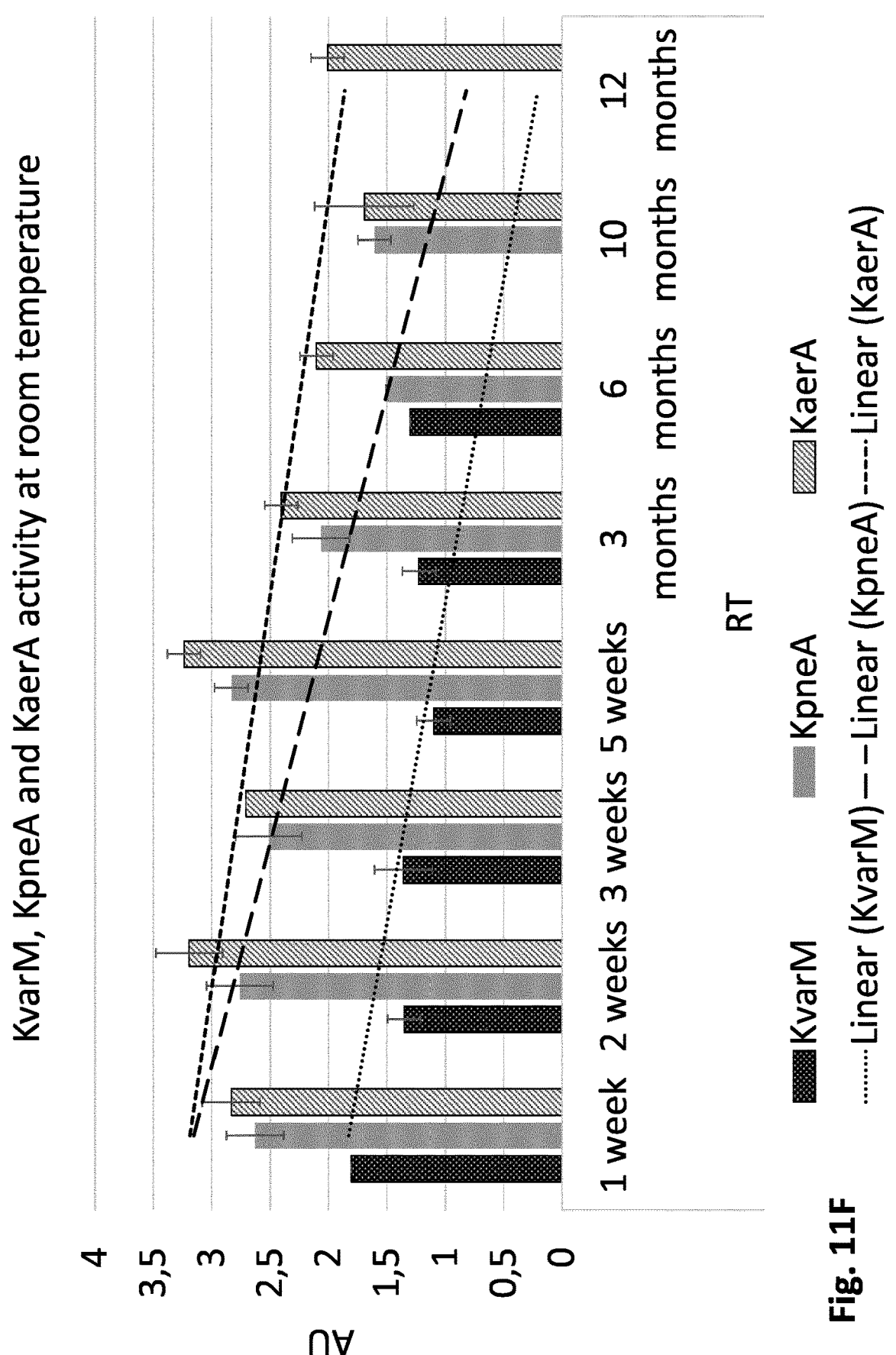
Figure 11G:
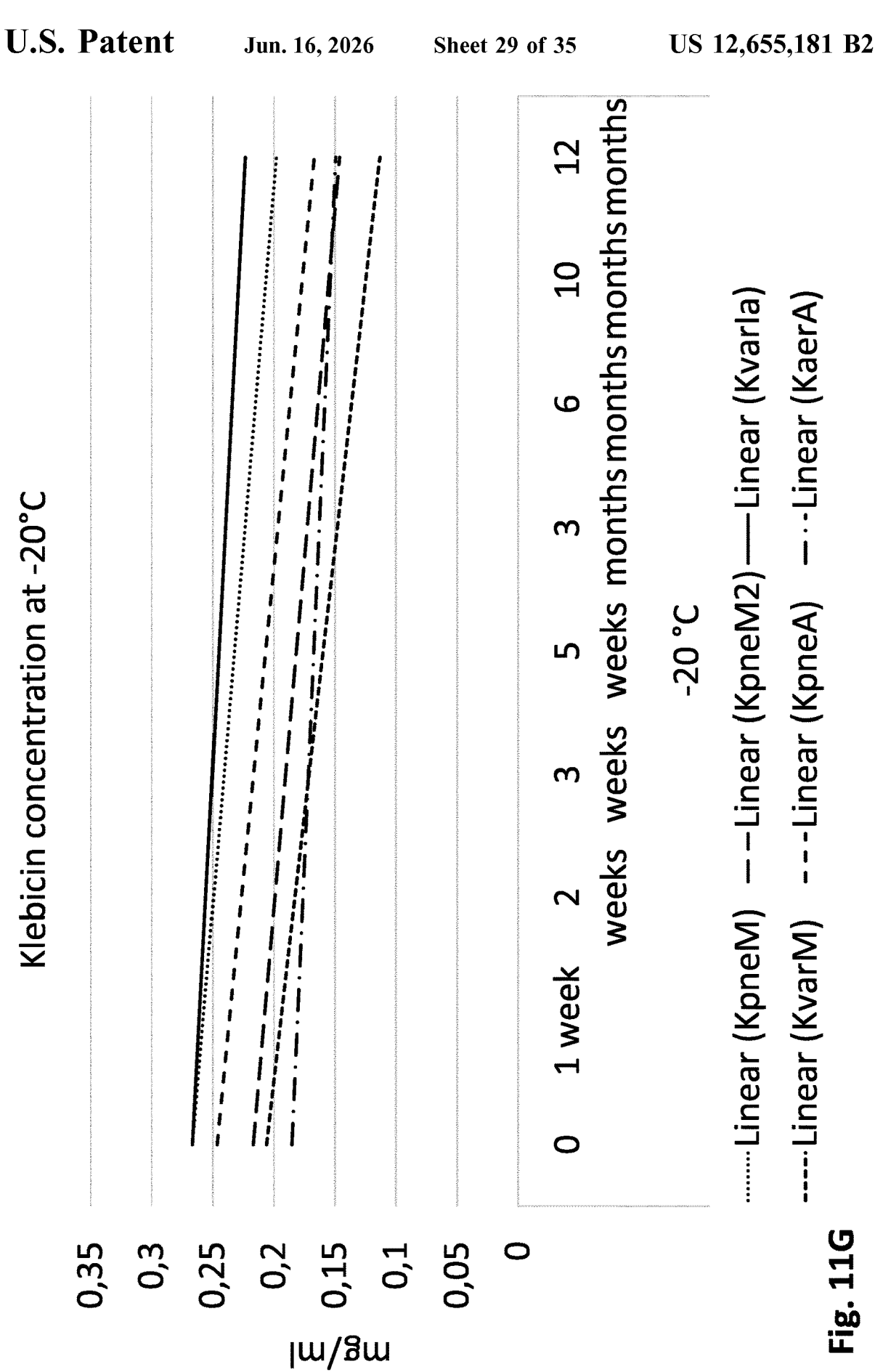

At –20° C., activity of all the klebicins KpneM, KpneM2, KvarM, KpneA, KaerA and Kvarla remained stable through-out the whole year (FIGS. 11A,D), despite the concentra-tions of soluble proteins decreased insignificantly (FIG. 11G).

Figure 11H:
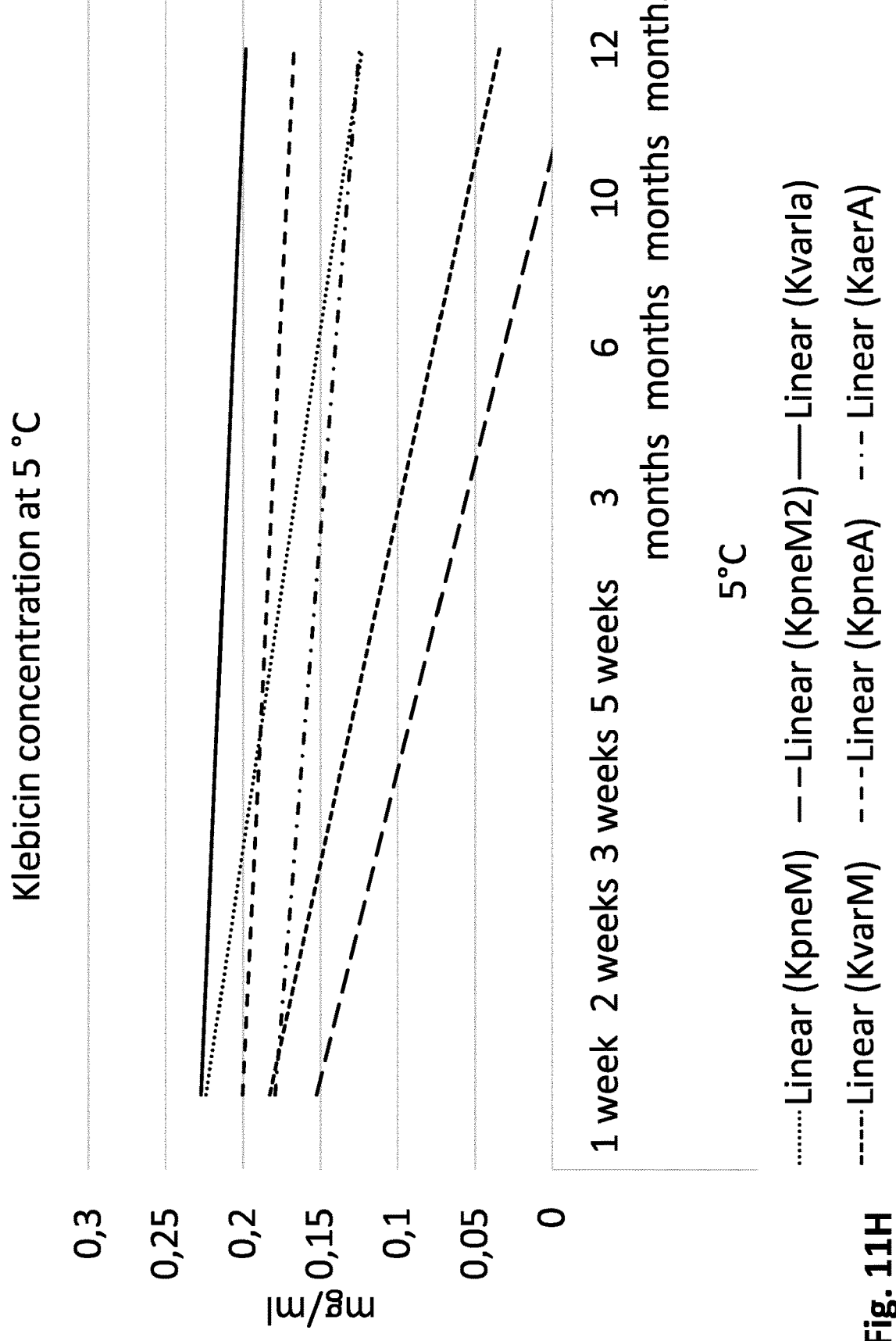

Upon the storage at 5° C., five out of six klebicins remained active for one year; the activity of KpneA decreased (FIG. 11E). Concentrations of KvarM and KpneM2 in solution decreased significantly suggesting cer-tain drop in solubility upon the storage (FIG. 11H).

Figure 11I:

In general, klebicins were less stable during storage at room temperature. Nevertheless, activities of klebicins Kvarla and KpneM remained stable for one year. Activities of KpneA, KvarM and KpneM2 decreased dramatically (FIG. 11C). This reduction in activity correlates with the concentration of protein in solution suggesting decrease in solubility upon the storage (FIG. 11I).

Example 12: Evaluation of Bacteriocin Kvarla Activity Against *Klebsiella quasipneumoniae* in Mice Gastrointestinal Model

*K. pneumoniae* is the normal component of human gut microbiota. Gastrointestinal carriage has been regarded as a major reservoir of *K. pneumoniae* infections, especially in intensive care patients (Gorrie et al., 2017). A prospective study in 1971 indicated that 18.5% patients colonized with multidrug-resistant *K. pneumoniae* after hospital admission had higher risk to develop subsequent infection caused by identical bacteria within 21 days compared to those who did not become intestinal carriers (45% vs. 11%) (Martin and Bachman, 2018).

Orally delivered klebicins could be an efficient tool for the eradication of symptomless multiresistant *K. pneumoniae* from the gut of hospitalized patients. As klebicins are quickly inactivated by gastrointestinal enzymes in case of oral admission, they should be formulated for gastric pro-tection and release in the small and large intestine. In this example, klebicin Kvarla was formulated with Eudragit S100 for ileum and colon delivery (release of klebicin at pH above 7) and administered by oral gavage to mice with *K. quasipneumoniae* colonized gut.

Coating of KvarlA

5% Eudragit S100 solution was prepared by dissolving 0.5 g Eudragit S100 (Evonik) in 10 ml of miliQ $H_2O$ and by sonication in ultrasonic bath for 30 min at 25° C. 250 μg of Kvarla was dissolved in 200 μg of 5% Eudragit S100. Resulting solution was lyophilized at –51° C. for 24 h.

58

Simulated Gastric Digestion, Activity Evaluation by Radial Diffusion Assay.

To find out if Eudragit-S100-coated Kvarla is resistant to pepsin digestion, simulated gastric digestion experiment was performed. Exposures of the proteins to Simulated Gastric Fluid (SGF, commercial acidic pepsin extract) were done using low enzyme-to-substrate ratios. Methods were derived from Moreno et al. (2005), Mandalari et al. (2009) and Eiwegger et al. (2006). Briefly, plant-produced Kvarla and Eudragit-S100-coated Kvarla were mixed with SGF in rec-ommended concentration and incubated for up to 60 min at 37° C. Every few minutes, samples of digestion mix were taken for analysis; the digestion of the protein into fragments was assessed using SDS-PAGE; in parallel, residual antimi-crobial activity was evaluated using radial diffusion assay. Coomassie staining on gels was used to visualize protein decomposition and estimate the MW of peptide products, but this method was only used for uncoated Kvarla, as Eudragit S100 distorted protein migration on the SDS-PAGE gel.

Protein samples were incubated at 37° C., with rotation at 200 rpm for 10 min. Pepsin (0.15 M NaCl, 5 mg/ml) was added to give 80-113 U (pepsin:protein ratio 1:40) of pepsin per mg of protein in the final digestion mix containing 1 mg of protein and 0,025 mg of pepsin. The samples were placed in shaker (200 rpm, 37° C.). Aliquots of reaction (50 μl) was removed at different time points (0.5, 5, 10, 20, 30 and 60 min). Digestions were stopped by raising the pH to 6.5 by addition of 0.5 M ammonium bicarbonate (10 μl of NH $HCO_3$) to inactivate pepsin.

Eudragit-coated Kvarla samples were adjusted to pH 8 to get Eudragit coat dissolved. Then dilutions of all samples by ratio 1:2 were made in distilled water and 5 μL aliquots of diluted samples were dropped on MHA plates with *K. quasipneumoniae* DSM28212 lawn for soft agar overlay assay.

Figure 12A:
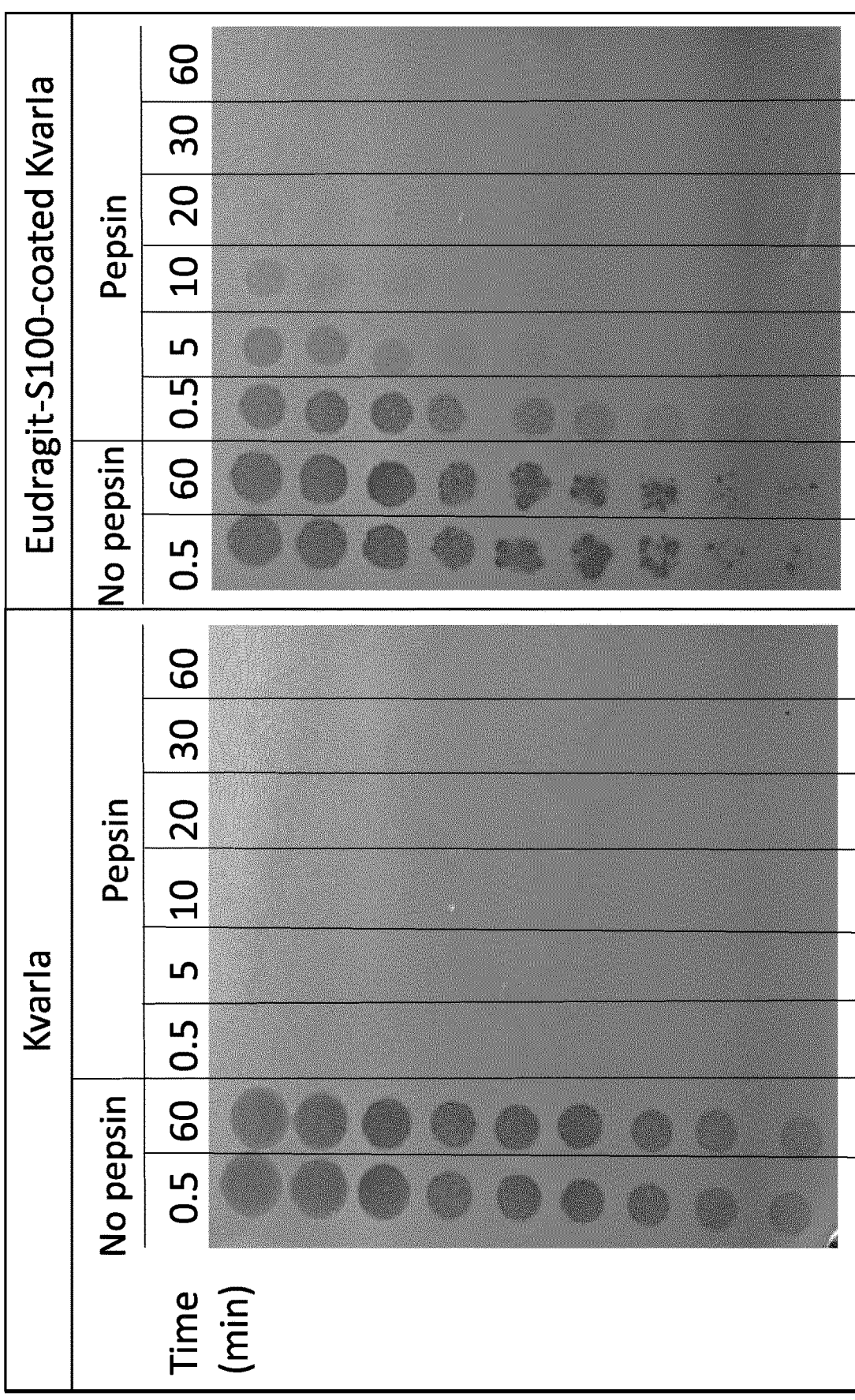
Figure 12B:
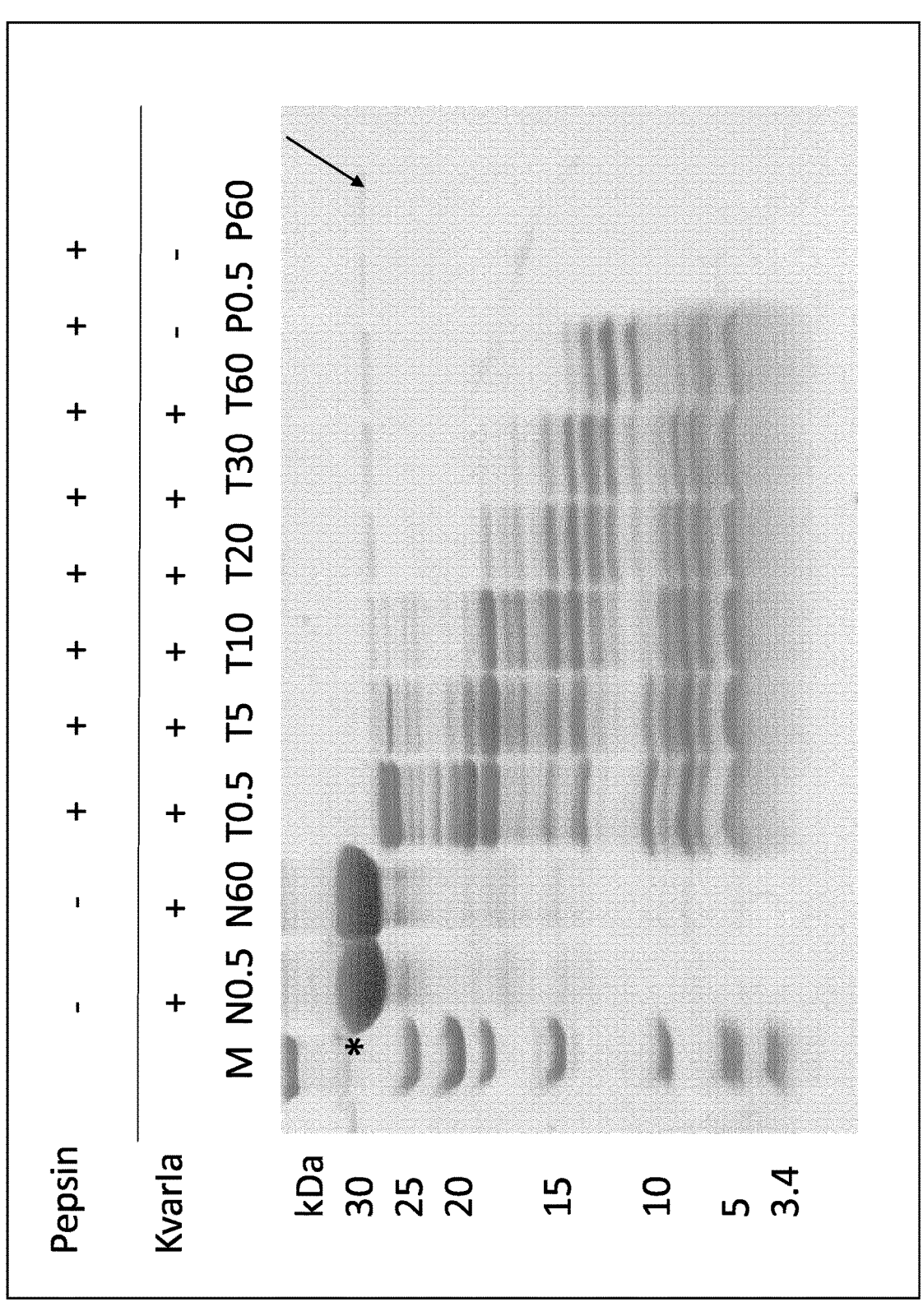

It appears that under the conditions used (pepsin:protein ratio 1:40), protein coating with Eudragit S100 is able to provide temporal resistance to pepsin digestion. Coated Kvarla demonstrated still detectable activity in agar diffu-sion assay after 20 min of in vitro gastric digestion, while non-coated Kvarla was inactivated in simulated gastric juice very quickly, and completely lost its activity already after 0.5 min of digestion (FIG. 12A). From SDS-PAGE profile of uncoated Kvarla digestion products, it is apparent that uncoated Kvarla is digested by pepsin very rapidly, and the full length protein in undetectable on the gel after 5 min of digestion (FIG. 12B).

Colonization of Mice Gut by *K. quasipneumoniae* DSM28212 and Kvarla Treatment

Before the experiment, BALB/c mice (n=12) were accli-mated in individual cages for 3 days. Three consecutive days, mice were given drinking water with ampicillin (2000 U/ml) and streptomycin (2 mg/ml) for eradication of gut microflora. Ampicillin in drinking water was continued till the end of experiment.

At 4th-to-6th and 11th-to-13th days of experiment, the mice were given using gavage 109 cfu of *K. quasipneumo-niae* DSM28212 once daily. Five days after last *K. quasip-neumoniae* gavage (18th day) mice were separated into four groups (n=3): first group was given PBS gavage, second group was given 100 μg of Kvarla, third group was given 100 μg of Eudragit-S100-coated Kvarla, and fourth group was given 1000 μg of Eudragit-S100-coated Kvarla. The gavage was continued $18^{th}$-to-$21^{nd}$ day (four days), once daily. The faecal samples were collected before the inoculation of *K. quasipneumoniae*, then daily from 18th (just before the start of the Kvarla treatment) to 22nd day of experiment.

During therapy, the cages were replaced daily. The mice received normal diet and food and water ad libitum during all the experiment, but 6 hours before the gavage the animals were starved.

Faeces collected at 18th day of experiment (just before the start of Kvarla treatment) and 22nd day of experiment (one day after last Kvarla treatment) were used to quantify the amount of *K. quasipneumoniae* DNA by real time-PCR.

Real Time PCR

DNA was extracted from 50 mg of faeces by use of QIAamp Fast DNA Stool Mini Kit (Qiagen). *Klebsiella* hemolysin gene (khe) marker was used for amplification. khe gene amplification primers used: Forward: 5-GAT-GAAACGACCTGATTGCATTC-3 (SEQ ID NO: 56), Reverse: 5-CCGGGCTGTCGGGATAAG-3 (SEQ ID NO: 57), Probe: 5-6FAM-CGCGAACTGGAAGGGCCCG-TAMRA-3 (SEQ ID NO: 58). "TaqMan Universal Master Mix II with UNG" and "TaqMan probe" (Applied Biosys- Colonization of Mice Gut by *K. quasipneumoniae* DSM28212 Before and After Klebicin Gavage Real time PCR results confirmed that at 18th day of experiment (before the start of klebicin treatment) all mice demonstrated the presence of *K. quasipneumoniae* DNA in faeces. At 18th day of experiment, median CT values of each group of mice were in range of 18.3-20.5 (FIG. 14 and Table 9).

According to real time PCR results, the numbers of *K. quasipneumoniae* kept rising in the faeces of groups of mice treated by PBS and by uncoated Kvarla. At the day 22, the day after last klebicin treatment, median CT value in PBS group decreased from 19.97 to 17.23, and in Kvarla treated group from 20.05 to 18.36.

In contrast to the PBS-treated and uncoated Kvarla-treated mice, the amount of *K. quasipneumoniae* DNA sharply decreased in faeces of mice treated by Eudragit-S100-coated Kvarla (both concentrations). Median CT values increased by 8-8.5 cycles (from 18.5 to 26.3 for Eudragit_S100-Kvarla 100 µg group and from 18.86 to 27.43 for Eudragit_S100-Kvarla 1 mg group) (FIG. 14 and Table 9).

TABLE 9

| CT values of each individual mouse after Klebsiella colonization and after therapy. | | | |
|---|---|---|---|
| Day 18 (before treatment) | | Day 22 (after treatment) | |
| GROUP 1, PBS | CT value | GROUP 1, PBS | CT value |
| Mouse 1 | 17.79 | Mouse 1 | 15.98 |
| Mouse 2 | 20.59 | Mouse 2 | 15.00 |
| Mouse 3 | 21.53 | Mouse 3 | 20.72 |
| Mean | 19.97 | Mean | 17.23 |
| GROUP 2, day 18 | | GROUP 2, day 22 | |
| Uncoated Kvarla 100µg | CT value | Uncoated Kvarla 100 µg | CT value |
| Mouse 1 | 17.31 | Mouse 1 | 17.34 |
| Mouse 2 | 20.13 | Mouse 2 | 16.38 |
| Mouse 3 | 22.70 | Mouse 3 | 21.38 |
| Mean | 20.05 | Mean | 18.36 |
| GROUP 3, day 18 | | GROUP 3, day 22 | |
| Eudragit_S100-Kvarla 100µg | CT value | Eudragit_S100-Kvarla 100µg | CT value |
| Mouse 1 | 20.68 | Mouse 1 | 26.53 |
| Mouse 2 | 16.82 | Mouse 2 | 25.08 |
| Mouse 3 | 17.41 | Mouse 3 | 27.29 |
| Mean | 18.30 | Mean | 26.30 |
| GROUP 4, day 18 | | GROUP 4, day 22 | |
| Eudragit_S100-Kvarla 1 mg | CT value | Eudragit_S100-Kvarla 1 mg | CT value |
| Mouse 1 | 17.28 | Mouse 1 | 27.50 |
| Mouse 2 | 18.57 | Mouse 2 | 29.08 |
| Mouse 3 | 20.72 | Mouse 3 | 25.71 |
| Mean | 18.86 | Mean | 27.43 | tems, JAV) were used. 14 ng of DNA was used for each PCR reaction. Following controls were used for real time PCR: *K. quasipneumoniae* DSM28212 DNA (*Klebsiella* hemolysin gene khe amplification in cycle 13), *E. coli* DNA—no khe amplification and blanc—no khe amplification.

TABLE 8

| Real time-PCR conditions. | | | | |
|---|---|---|---|---|
| | UNG incubation | Activation of polymerase | PCR Denaturation | (40 cycles) Elongation |
| Temperature (C °) | 50 | 95 | 95 | 60 |
| Time | 0:20 | 10:00 | 0:15 | 1:00 |

Real time PCR was validated by setting up a standard curve for detection of *K. quasipneumoniae*. According to this curve, CT 38 correspond to $10^3$ CFU, CT 24 corresponds to $10^6$ CFU and CT 17- to $10^8$ CFU of *K. quasipneumoniae* (FIG. 13).

Thus, according to real time PCR results, Eudragit-S100-coated Kvarla drastically decreased the *K. quasipneumoniae* DNA amount in the faeces of mice. The obtained decrease was similar for both dosages used: 100 µg and 1 mg. By contrast, the *K. quasipneumoniae* DNA amount slightly increased in uncoated Kvarla-treated and PBS-treated mice.

In conclusion, Eudragit-S100-coated Kvarla demonstrated high activity in reducing *K. quasipneumoniae* DNA amount in the gut of mice, which is indicative of the decrease in the population of this bacterium.

```
NUCLEIC ACID AND AMINO ACID SEQUENCES
SEQ ID NO: 1 referred to as KpneM
(K. pneumoniae EWD35590.1)
MSETMVWATPTGFEPAGYGGGLFSPSTPNHSPSQ

GQIFLQVTLPYYQSTKFCQDSMAWLAQYVKTHGAQ

DPLTIQVVANNIRYFLNADTNLCHNPKQNVWEAFH
```

-continued

SEMTHSGPPPAKYDYHSMSLKQMSGNVVTPAAAFG

HYLWGNGEARYVNLPDVGLKITPQMIPELMNIVNS

GVTGHIPVDIKFVHDTSVSGGIVPAAYLGHITLRT

EGTLDIQSGGAWTYNGVARAF

NDTYDFNLGDFRGPIAESMTFLGSQFTGKQYEISM

PGQINISGSGRR

SEQ ID NO: 2 referred to as KvarM
(*K. variicola* CTQ17225.1)
MSDTMIVVATPTPGFSYASGLTYGGGAFAGAPANG

PSEGQIFFQTVLPAYQSPNLCIGQLAWMTDYINKN

GVGNPKTWEVISQNVLIFCSADTALVLNPRIAVYD

GFHKTKWAPAKFNFKTQSQEKFSGNVTTPIAAFGH

YLWGEGKPRTVDLSSVGLKIQANQIDPVMIAVKNN

AAGTYQISGNFNRNTFIDGDIPGLYLGNITMKTEG

TLKIDAKGNWNYNGVVRAFNDTYDANPSTHRSKSA

EDLTTLLRLTQGTPYEIRIPGELKVSGSGKK

SEQ ID NO: 3 referred to as KpneM2
(*Klebsiella* sp. WP_047066220)
MSETLVWAPAPSAPSMTYGGGLIYSSIPSGPNEGQ

IFFQTVLPAYSSPNFCTDRLRWMVKFINENGVGNP

DTWKTLADVIRYYASADTAISKNPKTNPYDAWHKC

PWPPASFDVKTMSVEKFSGSVNTPIVAFGHYL

WGEGKPRSVDLSTVGLKVQANQIDPVMIAVKSYGA

GTYQINGNFNRNTFDDGVIPGLYLGNITLKTEGTL

KIEKNGSWNYNGVIRAFNDTYDANPSN

HRSQAAEDLTTLLRITQGTPYEIRIPGEIKVSGSG

KK

SEQ ID NO: 4 referred to as KaerM
(*K. aerogenes* WP_015367360.1)
MTDTLTVTATIPNGSSFNFQFEGMGNYYAAGSSTW

DDPAMADAAHLYNAIQSMEDGSFTKALFADWLQFN

AKGRENIPMINARFATMETMRFNDPGKAYFQFAQY

NEYEGHTPGNNFTSGAFAPFLGLWHYISGNGVETS

LDITTIGLTFNQSNLTPVNDALKSQPPGNYPISSN

FGKSVAEDNLYVAALLGRISMKTEGTLSIGESGEW

SYNGVVRAYNDTYDAIMFDPSRGVIAQASTTVLSW

FNGKPYPIALPGEIPVQLSGHR

SEQ ID NO: 5 referred to as KpneA
(*K. pneumoniae* SAV78255.1)
MPEETLTWGGGNNSCNVSWGGGNGIMNGGAGYSGK

YGGTSYEGATSMLKLNDRVLIQLYLCNPLNPDYIG

APWGSDKDAESIIRANRDKPGKFKANIQNWKTSGT

GSLGSPVVGKSYSSGDVDTYSVSFGKEKYNVLYNR

KKDSFTTAYVDGGANKPEHSMKDQAIAVVKLYLLN

-continued

ESQASVIDTTSGIITDSGKTLSGKLGDKYNTLARE

AADNIKNFQGKKLRSFNDAMASINELANNPKMKLS

QADKTWSNALKQMDLSALADRFKGLEKAFTWGDRL

LKAEKIRDGVVTGVTTGDWQKLAFEVEAMYLSGVA

GAVALGITTAMISTVAVALSLPSVAVSALTWAVIG

ISILTSYIDADKAKALNNAVLGLFK

SEQ ID NO: 6 referred to as
KaerA (*K. aerogenes* WP_063414841.1)
MANEDSMTVNGNAGSGVHWGGGSGNGNNGGAGSNG

GANVALGGTMEVELGNGFTMIVDGTHPINPGIGGA

PWSDDKSNKSAVDALNANKSKPAKFKANIQNYKSG

TQGSLNSPAVNKSSSSGDVDTYAVSFGKEKYNVMY

NRKKDSFTSGYVDGGATKPEHSMKDQAIAWQLYLL

NEKEKDVITTAAEIISSSGETISGKLGEKYKGLAQ

GVANDIRNFQGKKIRSFKDAMSSLEQFTKNPNMKL

NQADKAALVNALNQVNLSTLADRFKGLERAFTWAD

RLLKAQKIKDGVVTGVTTGNWQPLALEVEAMYLSG

VAGSVALGIVTGMISGLAALISIPALAVTALTVTA

VIGIAIATSYINADTAKALNNAVADLFK

SEQ ID NO: 7 referred to as Koxy
(*K. oxytoca* WP_024273778)
MAGFSYGGFGDGTTWSKERGTGPLPGGGSSGNSGN

HSNTTPAEQKQINAIRADKNVRARLSNLIKAARKL

NPSVKITVHAISPEGTMAISMEGLTATQARQAG

LTGLVMGITVPGYIGSVGDFETGHKYNLKNPEKLN

SIGVGTPLDGFNGGENIDTTPKKYRNWRATDEKSF

YYVGTTVPMRLLHHLTVSRNKETDTYTMYFKAKDI

KALYKIEVKNGDLDNMKLTTLAQGHPLFTAEFAKD

IVRNFASVKNESDKEVLDKTSGVIISGVGDKAGALL

GEKYKALSREVASNIQNFQGKQIRTYDQAMASMNK

LMTNPNMKIKAADKTAVINAWKAFNVEDMGNKFTA

LGRAFKVADYVTKGNNVREKSITGYETGNWGPLMR

EVESWTVSGLTSSVALAVFSATLGAMLVAAGVSTA

VVGIIGIIIAGLIGALIDDKFIDKLNNEIIRPAY

SEQ ID NO: 8 referred to as Kpnela
(*K. pneumoniae* BAS34675)
MPGFNYGGKGDGTNWSSERGTGPEPGGGSRGNGGD

RDNSRGGAGNRGNWAGSGPLSAALINDSIAEALEK

QLPRNTVEATSTPAYKKMRAAFDALPLDKQPEARA

QITKAWQSAHDAMPDKTTTTENVGGGKNGHNVTRS

TPNWLKEKMKGLNQQVNNDLSGALAQHQKAEADAR

AKAEAAAKAKAEAEAKAKAEAEAKAKAKAEAAAKA

KAEAEAKAKAEAEAKAKAEAAAKAKAEAEAKAKAE

AEAKAKAEAAAKAKAEAEAKAKAEAEAKAKAEAEA

-continued

KAKAEADAVKDAVKFTADFYKEVFSVYGEKAEQLA

NLLATQAKGKNIRNIDDALKAYEKHKTNINKKINA

QDRAAIAKALESVDVKEAAKNFAKFSKGLGYVGPT

MDVVDLVLELRKAIKEDNWRSFFVKIEAIAISFGA

TQLAALAFASLLGAPVGLLGYALIMAGIGALVSDD

VVDAANKIIGI

SEQ ID NO: 9 referred to as Kvarla
(*K. variicola* KDL88409)
MPGFNYGGKGDGTNWSSERGTGPEPGGGSRGNGGD

RDNSRGGAGNRGNWAGSGPLSAALINDSIAEALEK

QLPRNTVEATSTPAYKKMRAAFDALPLDKQPEARA

QITKAWQSAHDAMPDRTTTTENVGGGKNGHNVTRS

TPNWLKEKMKGLNQQVNNDLSGALAQHQKAEADAR

AKAEAAAKAKAAAKAKAEAEAKAKAEAEAKAKAEA

AAKAKAEAEAKAKAEAEAKAKAEADAVKDAVKFTA

DFYKEVFSVYGEKAEQLANLLATQAKGKNIR

NIDDALKAYEKHKTNINKKINAQDRAAIAKALESV

DVKEAAKNFAKFSKGLGYVGPTMDVVDLVLELRKA

IKEDNWRTFFVKIEAIAISFGATQLAALAFASLLG

APVGLLGYALIMAGIGALVSDDVVDAANKIIGI

SEQ ID NO: 10: ExbB Eco88I fwd
AAACTCGGGTTGATGAACCTGTTTTTATACGTCT

SEQ ID NO: 11 ExbB Eco81I rev
AAACCTGAGGTCAACCTACCCGTAATTTCTGCG

SEQ ID NO: 12 ExbB Eco88I fwd
AAACTCGGGTTGATGAACCTGTTTTTATACGTCT

SEQ ID NO: 13 ExbD Eco81I rev
AAACCTGAGGTTATTTGGCTTTGACGGTCTC

SEQ ID NO: 14 FhuA Eco81I fwd
AAACCTCAGGTTTAAGCCCTAAGACCAGACCC

SEQ ID NO: 15 FhuA Eco 81I rev
AAACCTGAGGTTAGAAACGGAAGGTGGCGGTG

SEQ ID NO: 16 FimB Eco88I fwd
AAACTCGGGGCTCCCGTAGCAAATAAAAACG

SEQ ID NO: 17 FimB Eco81I rev
AAACCT GAGGTTACT GAAGCAGCGACAGGCG

SEQ ID NO: 18 OmpC Eco88I fwd
AAACTCGGGCTTGTGGCTGAACGACTCATCA

SEQ ID NO: 19 OmpC Eco81I rev
AAACCTGAGGTTAGAACTGGTAAACCAGGCCC

SEQ ID NO: 20 TonB PsyI fwd
AAAGACCGGGTCGGCAAAGCTCCTTATCAATAAACA

SEQ ID NO: 21 TonB BseSI rev
AAAGTGCCCTCAGTTAATCTCGACGCCGTTG

SEQ ID NO: 22
Consensus sequence M (KpneM2, KvarM,
KpneM, KaerM)
MSXTXVWATPXXXXXXXXXTYGGGLFYXXXPXGPSE -continued

GQIFFQTVLPAYQSPNFCXDXLAWMADYINXNGVG

NPXTWEVIAXNIRYFASADTALXXNPKXXVYDAFH

KXXWPPAKXDXXTMSXEKFSGNVXTPIAAFGHYLW

GXGKPRSVDLSTVGLKIQANQIDPVMIAVKSXXAG

TYXISGNFNRNTFXDGXIPXXYLGNITXKTEGTLK

IXXXGXWNYNGWRAFNDTYDANPSXHRXXIAEDLT

TLLXXXQGXPYEIRIPGEIKVSGSGKX

SEQ ID NO: 23
Consensus sequence A (KaerA, KpneA)
MXXEXXXXVXGXNXXXXVXWGGXXGNGNNGGAGXX

GXXGXXXXXGXTXXXXLXBXXXXXXXXXXXPJNPXX

XGAPWXXXXSBKXAXXXJXANXXKPXKFKANIQNX

KXXXXGSLXSPXVXKSXSSGDVDTYXVSFGKEKYN

VXYNRKKDSFTXXWDGGAXKPEHSMKDQAIAWXLY

LLNEXZXXVIXTXXXIIXXSGXTJSGKLGXKYXXL

AXXXABBIXNFQGKKJRSFXDAMXSJXZXXXNPXM

KLXQADKXXXXNALXQXBLSXLADRFKGLEXAFTW

XDRLLKAZKIXDGWTGVTTGBWQXLAXEVEAMYLS

GVAGXVALGIXTXMISXXAXXJSJPXXAVXALTVX

AVIGIXIXTSYIBADXAKALNNAVXXLFK

SEQ ID NO: 24
Consensus sequence 1a (Kpnela, Kvarla)
MPGFNYGGKGDGTNWSSERGTGPEPGGGSRGNGGD

RDNSRGGAGNRGNWAGSGPLSAALINDSIAEALEK

QLPRNTVEATSTPAYKKMRAAFDALPLDKQPEARA

QITKAWQSAHDAMPDXTTTTENVGGGKNGHNVTRS

TPNWLKEKMKGLNQQVNNDLSGALAQHQKAEADAR

AKAEAAAKAKXXXXXXXXXXXXXXXXXXXXXXXXXX

XXXXXXXXXXXXXXXXXXXXXXXXXXXXAXAKAKAE

AEAKAKAEAXAKAKAEAXAKAKAEAEAKAKAEAEA

KAKAEADAVKDAVKFTADFYKEVFSVYGEKAEQLA

NLLATQAKGKNIRNIDDALKAYEKHKTNINKKINA

QDRAAIAKALESVDVKEAAKNFAKFSKGLGYVGPT

MDVVDLVLELRKAIKEDNWRXFFVKIEAIAISFGA

TQLAALAFASLLGAPVGLLGYALIMAGIGALVSDD

VVDAANKIIGI

SEQ ID NO: 25 conserved sequence
stretch in SEQ ID NO: 22
TEGTL

SEQ ID NO: 26 conserved sequence
stretch in SEQ ID NO: 22
YNGV

SEQ ID NO: 27 conserved sequence
stretch in SEQ ID NO: 22
RAFNDTYD

-continued

```
SEQ ID NO: 28 conserved sequence
stretch in SEQ ID NO: 23
GNGNNGGAG

SEQ ID NO: 29 conserved sequence
stretch in SEQ ID NO: 23
GAPW

SEQ ID NO: 30 conserved sequence
stretch in SEQ ID NO: 23
KFKANIQN

SEQ ID NO: 31 conserved sequence
stretch in SEQ ID NO: 23
SSGDVDTY

SEQ ID NO: 32 conserved sequence
stretch in SEQ ID NO: 23
VSFGKEKYNV

SEQ ID NO: 33 conserved sequence
stretch in SEQ ID NO: 23
YNRKKDSFT

SEQ ID NO: 34 conserved sequence
stretch in SEQ ID NO: 23
YVDGGA

SEQ ID NO: 35 conserved sequence
stretch in SEQ ID NO: 23
KPEHSMKDQAIAW

SEQ ID NO: 36 conserved sequence
stretch in SEQ ID NO: 23
LYLLNE

SEQ ID NO: 37 conserved sequence
stretch in SEQ ID NO: 23
SGKLG

SEQ ID NO: 38 conserved sequence
stretch in SEQ ID NO: 23
NFQGKK

SEQ ID NO: 39 conserved sequence
stretch in SEQ ID NO: 23
QADK

SEQ ID NO: 40 conserved sequence
stretch in SEQ ID NO: 23
LADRFKGL

SEQ ID NO: 41 conserved sequence
stretch in SEQ ID NO: 23
AFTW

SEQ ID NO: 42 conserved sequence
stretch in SEQ ID NO: 23
DRLLKA

SEQ ID NO: 43 conserved sequence
stretch in SEQ ID NO: 23
DGWTGVTTG

SEQ ID NO: 44 conserved sequence
stretch in SEQ ID NO: 23
EVEAMYLSGVAG

SEQ ID NO: 45 conserved sequence
stretch in SEQ ID NO: 23
VALGI

SEQ ID NO: 46 conserved sequence
stretch in SEQ ID NO: 23
ALTV

SEQ ID NO: 47 conserved sequence
stretch in SEQ ID NO: 23
AVIGI
```

-continued

```
SEQ ID NO: 48 conserved sequence
stretch in SEQ ID NO: 23
TSYI

SEQ ID NO: 49 conserved sequence
stretch in SEQ ID NO: 23
AKALNNAV

SEQ ID NO: 50 conserved sequence
stretch in SEQ ID NO: 24
MPGFNYGGKGDGTNWSSERGTGPEPGGGSRGNGGD

RDNSRGGAGNRGNWAGSGPLSAALINDSIAEALEK

QLPRNTVEATSTPAYKKMRAAFDALPLDKQPEARA

QITKAWQSAHDAMPD

SEQ ID NO: 51 conserved sequence
stretch in SEQ ID NO: 24
TTTTENVGGGKNGHNVTRSTPNWLKEKMKGLNQQV

NNDLSGALAQHQKAEADARAKAEAAAKAK

SEQ ID NO: 52 conserved sequence
stretch in SEQ ID NO: 24
AKAKAEAEAKAKAEA

SEQ ID NO: 53 conserved sequence
stretch in SEQ ID NO: 24
AKAKAEA

SEQ ID NO: 54 conserved sequence
stretch in SEQ ID NO: 24
AKAKAEAEAKAKAEAEAKAKAEADAVKDAVKFTAD

FYKEVFSVYGEKAEQLANLLATQAKGKNIRNIDDA

LKAYEKHKTNINKKINAQDRAAIAKALESVDVKEA

AKNFAKFSKGLGYVGPTMDWDLVLELRKAIKEDNW

R

SEQ ID NO: 55 conserved sequence
stretch in SEQ ID NO: 24
FFVKIEAIAISFGATQLAALAFASLLGAPVGLLGY

ALIMAGIGALVSDDVVDAANKIIGI

SEQ ID NO: 56 khe gene amplification
forward primer
GATGAAACGACCTGATTGCATTC

SEQ ID NO: 57 khe gene amplification
reverse primer
CCGGGCTGTCGGGATAAG

SEQ ID NO: 58 khe gene amplification
probe sequence, labelled with 6FAM
at the 5'-end and with TAMRA at the
3'-end
CGCGAACTGGAAGGGCCCG
```

REFERENCES

Bodier-Montagutelli E, Mayora A, Vecellioa L, Respauda R, Heuzé-Vourc'h N. Designing inhaled protein therapeutics for topical lung delivery: what are the next steps? Expert Opin Drug Deliv. 2018:15 (8): 729-736

Bulet P, Menin S R L. Anti-microbial peptides: from invertebrates to vertebrates. Immunol Rev 2004; 198:169-84

Chan Y R, Liu J S, Pociask D A, Zheng M, Mietzner T A, Berger T, et al. 2009. Lipocalin 2 is required for pulmonary host defense against *Klebsiella* infection. J Immunol. April 15 182 (8): 4947-56.

Chavan M1, Rafi H, Wertz J, Goldstone C, Riley M A. Phage associated bacteriocins reveal a novel mechanism for bacteriocin diversification in *Klebsiella*. J Mol Evol. 2005 April; 60 (4): 546-56)

Depreter F, Pilcer G, Amighi K. Inhaled proteins: challenges and perspectives. Int J Pharm. 2013: 447 (1-2): 251-80.

Eiwegger T, Rigbyw N, Mondouletz L, Bernardz H, Krauth M. T, Boehm A, Dehlink E, Valent P, Walz J. M, Millsw E. N. C, Szépfalusi Z. Gastro-duodenal digestion products of the major peanut allergen Ara h 1 retain an allergenic potential. 2006 Clinical and Experimental Allergy, 36, 1281-1288.

Ghequire M G, De Mot R. Ribosomally encoded antibacterial proteins and peptides from *Pseudomonas*. FEMS Microbiol Rev. 2014 July; 38 (4): 523-68

Grinter R, Milner J, Walker D. Beware of proteins bearing gifts: protein antibiotics that use iron as a Trojan horse. FEMS Microbiol Lett. 2013 January; 338 (1): 1-9

Gorrie, C. L., Mirceta, M., Wick, R. R., Edwards, D. J., Thomson, N. R., Strugnell, R. A., et al. (2017). Gastrointestinal carriage is a major reservoir of *Klebsiella pneumoniae* infection in intensive care patients. Clin. Infect. Dis. 65, 208-215. cix270

Gu D, Dong N, Zheng Z, Lin D, Huang M, Wang L, Chan E W, Shu L, Yu J, Zhang R, Chen S. A fatal outbreak of ST11 carbapenem-resistant hypervirulent *Klebsiella pneumoniae* in a Chinese hospital: a molecular epidemiological study. Lancet Infect Dis. 2017 Aug. 29. pii: S1473-3099 (17) 30489-9.

Hirche T O, Gaut J P, Heinecke J W. 2005. Myeloperoxidase plays critical roles in killing *Klebsiella pneumoniae* and inactivating neutrophil elastase: effects on host defense. J Immunol. 174 (3): 1557-65.

Harding C R, Schroeder G N, Collins J W, Frankel G (2013) Use of *Galleria mellonella* as a Model Organism to Study *Legionella pneumophila* Infection. J Vis Experiments 81: e50964.

Kleanthous C. (2010) Swimming against the tide: progress and challenges in our understanding of colicin translocation. Nat Rev Microbiol 8 (12): 843-848.

James R1, Schneider J, Cooper P C. Characterization of three group A klebicin plasmids: localization of their E colicin immunity genes. J Gen Microbiol. 1987 August; 133 (8): 2253-62.

Mandalari G, Adel-Patient K, Barkholt V, Baro C, Bennett L, Bublin M, Gaier S, Graser G, Ladics G. S, Mierzejewska D, Vassilopoulou E, Vissers Y. M, Zuidmeer L, Rigby N. M, Salt L. J, Defernez M, Mulholland F, Mackie A. R, Wickham M. S. J, Mills E. N. C. In vitro digestibility of b-casein and b-lactoglobulin under simulated human gastric and duodenal conditions: A multi-laboratory evaluation. Regulatory Toxicology and Pharmacology 55 (2009) 372-381.

Marillonnet S, Thoeringer C, Kandzia R, Klimyuk V, Gleba Y. (2005) Systemic *Agrobacterium tumefaciens* mediated transfection of viral replicons for efficient transient expression in plants. Nat Biotechnol 23:718-723.

Martin, R. M., and Bachman, M. A. (2018). Colonization, infection, and the accessory genome of *Klebsiella pneumoniae*. Front. Cell. Infect. Microbiol. 8:4.

Martínez-García E, Calles B, Arévalo-Rodríguez M, de Lorenzo V. (2011) pBAM1: an all-synthetic genetic tool for analysis and construction of complex bacterial phenotypes. BMC Microbiol 11:38.

Moreno F. J, Mellon F. A, Wickham M. S. J, Bottrill A. R, Mills E. N. C. Stability of the major allergen Brazil nut 2S albumin (Ber e 1) to physiologically relevant in vitro gastrointestinal digestion. FEBS Journal 272 (2005) 341-352.

Moskowitz S M, Foster J M, Emerson J, Burns J L. (2004) Clinically Feasible Biofilm Susceptibility Assay for Isolates of *Pseudomonas aeruginosa* from Patients with Cystic Fibrosis Clinically Feasible Biofilm Susceptibility Assay for Isolates of *Pseudomonas aeruginosa* from Patients with Cystic Fibrosis. J Clin Microbiol 42:1915-1922.

Paškevičius Š, Starkevič U, Misiūnas A, Vitkauskienė A, Gleba Y, Ražanskienė A. (2017) Plant-expressed pyocins for control of *Pseudomonas aeruginosa*. PLOS One 12 (10): e0185782.

Witt, D. M. and Anderson, L. (1996), Dornase Alfa: A New Option in the Management of Cystic Fibrosis. Pharmacotherapy: The Journal of Human Pharmacology and Drug Therapy, 16:40-48.

Ye Y, Xu L, Han Y, Chen Z, Liu C, Ming L. (2018) Mechanism for carbapenem resistance of clinical Enterobacteriaceae isolates. Exp Ther Med 15 (1): 1143-1149.

The content of European patent application No. 19 178 676.3, filed on Jun. 6, 2019 is incorporated herein by reference including description, claims, figures, and sequence listing.

The invention claimed is:

1. A method of treating infection with *Klebsiella* of a subject in need thereof, comprising administering to said subject a protein having cytotoxic activity against *Klebsiella* or a composition comprising said protein, said protein comprising or consisting of an amino acid sequence comprising or consisting of the amino acid sequence of SEQ ID NO: 2 (KvarM), SEQ ID NO: 1 (KpneM), SEQ ID NO: 3 (KpneM2), or SEQ ID NO: 4 (KaerM).

2. A method of reducing infection or contamination of an object infected or contaminated with one or more *Klebsiella* species, comprising determining contamination of the object with *Klebsiella* and contacting said object with a protein having cytotoxic activity against *Klebsiella*, or with a composition comprising said protein, said protein comprising or consisting an amino acid sequence comprising or consisting of the amino acid sequence of SEQ ID NO: 2 (KvarM), SEQ ID NO: 1 (KpneM), SEQ ID NO: 3 (KpneM2), or SEQ ID NO: 4 (KaerM).

3. The method according to claim 1, having cytotoxic activity against *Klebsiella pneumoniae, Klebsiella oxytoca, Klebsiella granulomatis, Klebsiella quasipneumoniae, Klebsiella aerogenes*, and/or *Klebsiella variicola.*

* * * * *